(12) United States Patent
Vrudhula et al.

(10) Patent No.: US 8,969,564 B2
(45) Date of Patent: Mar. 3, 2015

(54) ARYL ETHER-BASE KINASE INHIBITORS

(71) Applicant: Bristol-Myers Squibb Company, Princeton, NJ (US)

(72) Inventors: Vivekananda M. Vrudhula, Killingworth, CT (US); Senliang Pan, Woodbridge, CT (US); Ramkumar Rajamani, Woodbridge, CT (US); John E. Macor, Guilford, CT (US); Joanne J. Bronson, Durham, CT (US); Carolyn Diane Dzierba, Middletown, CT (US); Susheel Jethanand Nara, Bangalore (IN); Maheswaran Sivasamban Karatholuvhu, Chennai (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/188,141

(22) Filed: Feb. 24, 2014

(65) Prior Publication Data

US 2014/0179725 A1 Jun. 26, 2014

Related U.S. Application Data

(62) Division of application No. 13/777,144, filed on Feb. 26, 2013, now Pat. No. 8,703,953.

(60) Provisional application No. 61/608,737, filed on Mar. 9, 2012.

(51) Int. Cl.

| | | |
|---|---|---|
| *A61K 31/44* | (2006.01) | |
| *C07D 491/00* | (2006.01) | |
| *C12N 9/99* | (2006.01) | |
| *C07D 491/052* | (2006.01) | |
| *C07D 491/20* | (2006.01) | |
| *C07D 491/04* | (2006.01) | |

(52) U.S. Cl.
CPC .............. *C12N 9/99* (2013.01); *C07D 491/052* (2013.01); *C07D 491/20* (2013.01); *C07D 491/04* (2013.01)
USPC ........................................... 546/89; 514/278

(58) Field of Classification Search
None
See application file for complete search history.

(56) References Cited

FOREIGN PATENT DOCUMENTS

| | | |
|---|---|---|
| CN | 1733708 | 2/2006 |
| JP | 2007-217408 | 8/2007 |
| WO | WO 94/12461 | 6/1994 |
| WO | WO 96/21464 | 7/1996 |
| WO | WO 03/086325 | 10/2003 |
| WO | WO 2004/056745 | 7/2004 |
| WO | WO 2004/072018 | 8/2004 |
| WO | WO 2005/000309 | 1/2005 |
| WO | WO 2006/012227 | 2/2006 |
| WO | WO 2007/117715 | 10/2007 |
| WO | WO 2008/022154 | 2/2008 |
| WO | WO 2011/044195 | 4/2011 |
| WO | WO 2011/044212 | 4/2011 |

OTHER PUBLICATIONS

Buonanno, A., "The neuregulin signaling pathway and schizophrenia: From genes to synapses and neural circuits", Brain Research Bulletin, vol. 83, pp. 122-131 (2010).
Conner, S.D. et al., "AAK-1 Mediated μ2 Phosphorylation is Stimulated by Assembled Clathrin", Traffic, vol. 4, pp. 885-890 (2003).
Conner, S.D. et al., "Identification of an adaptor-associated kinase, AAK1, as a regulator of clathrin-mediated endocytosis", The Journal of Cell Biology, vol. 156, No. 5, pp. 921-929 (2002).
Greenwood, T.A. et al., "Analysis of 94 Candidate Genes and 12 Endophenotypes for Schizophrenia", Am. J. Psychiatry, vol. 168, No. 9, pp. 930-946 (2011).
Henderson, D.M. et al., "A Novel AAK1 Splice Variant Functions at Multiple Steps of the Endocytic Pathway", Molecular Biology of the Cell, vol. 18, pp. 2698-2706 (2007).
Jaaro-Peled, H. et al., "Review of Pathological Hallmarks of Schizophrenia: Comparison of Genetic Models with Patients and Nongenetic Models", Schizophrenia Bulletin, vol. 36, No. 2, pp. 301-313 (2010).
Jackson, A.P. et al., "Clathrin promotes incorporation of cargo into coated pits by activation of the AP2 adaptor μ2 kinase", The Journal of Cell Biology, vol. 163, No. 2, pp. 231-236 (2003).
Kuai, L. et al., "AAK1 Identified as an Inhibitor of Neuregulin-1/ErbB4-Dependent Neurotrophic Factor Signaling Using Integrative Chemical Genomics and Proteomics", Chemistry & Biology, vol. 18, pp. 891-906 (2011).
Latourelle, J.C. et al., "Genomewide association study for onset age in Parkinson disease", BMC Medical Genetics, 10:98 (2009).
Motley, A.M. et al., Functional Analysis of AP-2 α and μ2 Subunits, Molecular Biology of the Cell, vol. 17, pp. 5298-5308 (2006).
Ricotta, D. et al., "Phosphorylation of the AP2 μ subunit by AAK1 mediates high affinity binding to membrane protein sorting signals", The Journal of Cell Biology, vol. 156, No. 5, pp. 791-795 (2002).
Wen, L. et al., "Neuregulin 1 regulates pyramidal neuron activity via ErbB4 in parvalbumin-positive interneurons", Proc. Natl. Acad. Sci. USA, vol. 107, No. 3, pp. 1211-1216 (2010).
Bi et al., U.S. Appl. No. 13/785,271, filed Mar. 5, 2013.
Bi et al., U.S. Appl. No. 13/785,355, filed Mar. 5, 2013. Lanthorn et al., U.S. Appl. No. 13/786,575, filed Mar. 6, 2013.
CAPLUS 1952:57246.
CAPLUS 1992:426368.

*Primary Examiner* — Heidi Reese
(74) *Attorney, Agent, or Firm* — Pamela A. Mingo

(57) ABSTRACT

The present disclosure is generally directed to compounds which can inhibit AAK1 (adaptor associated kinase 1), compositions comprising such compounds, and methods for inhibiting AAK1.

3 Claims, 1 Drawing Sheet

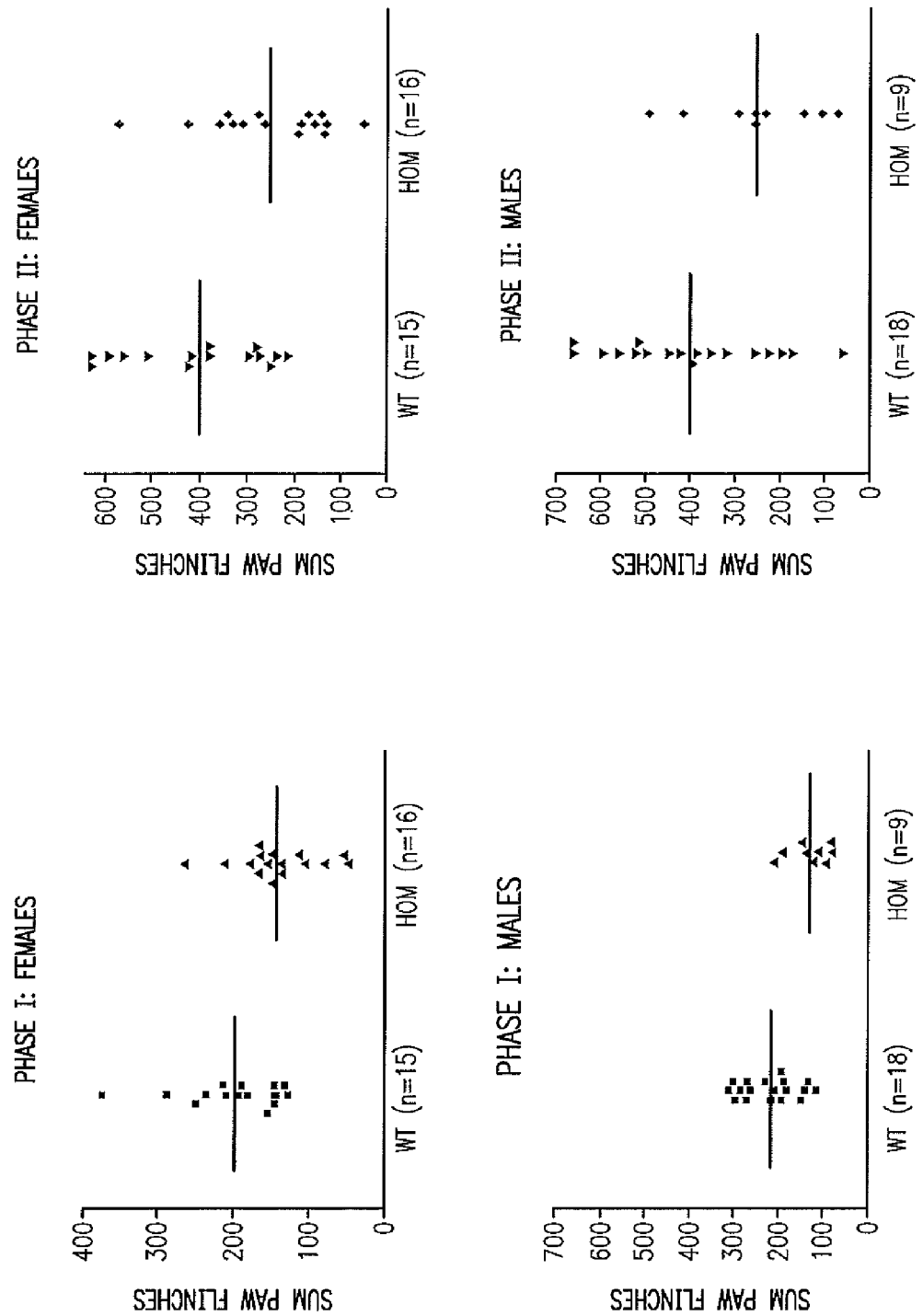

ARYL ETHER-BASE KINASE INHIBITORS

CROSS-REFERENCE TO RELATED APPLICATIONS

This Divisional application claims the benefit of U.S. Ser. No. 13/777,144 filed Feb. 26, 2013, now allowed, which in turn is a Non-Provisional application which claims the benefit of U.S. Ser. No. 61/608,737 filed Mar. 9, 2012.

The present disclosure is generally directed to compounds which can inhibit adaptor associated kinase 1 (AAK1), compositions comprising such compounds, and methods for inhibiting AAK1.

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., Proc. Natl. Acad. Sci. USA. 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, neuropathic pain, bipolar disorder, and Alzheimer's disease.

In a first aspect the present disclosure provides a compound of formula (I):

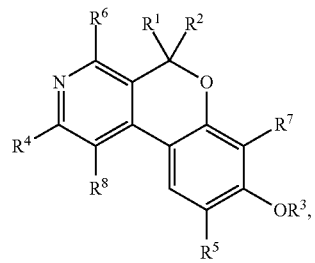

or a pharmaceutically acceptable salt thereof, wherein:

$R^1$ and $R^2$ are independently selected from hydrogen, $C_3$-$C_6$cycloalkyl, and $C_1$-$C_3$alkyl wherein the $C_1$-$C_3$alkyl is optionally substituted with one, two, or three groups independently selected from $C_1$-$C_3$alkoxy, $C_1$-$C_3$alkylamino, amino, cyano, $C_1$-$C_3$dialkylamino, halo, and hydroxy; or $R^1$ and $R^2$ together are oxo; or $R^1$ and $R^2$, together with the carbon atom to which they are attached, form an oxetane ring;

$R^3$ is $C_1$-$C_3$alkyl-Y or $C_2$-$C_8$alkyl, wherein the $C_2$-$C_8$alkyl is optionally substituted with one, two, three, or four groups independently selected from $C_1$-$C_3$alkoxy, $C_1$-$C_3$alkylamino, $C_1$-$C_3$alkoxyC_2$-$C_3$alkylamino, amino, aryl, halo, $C_1$-$C_3$haloalkylamino, $C_1$-$C_3$haloalkylcarbonylamino, hydroxy, —$NR^xR^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxyC_2$-$C_{1-3}$alkylamino, amino, aryl, aryl$C_1$-$C_3$alkyl, halo, $C_1$-$C_3$halo alkyl, $C_1$-$C_3$haloalkylamino and hydroxy;

$R^4$ is selected from hydrogen, $C_1$-$C_3$alkoxy, $C_1$-$C_3$alkoxycarbonylamino, $C_1$-$C_3$alkyl, $C_1$-$C_3$alkylamino, $C_1$-$C_3$alkylcarbonylamino, amino, arylamino, arylcarbonylamino, $C_3$-$C_6$cycloalkylamino, $C_3$-$C_6$cycloalkylcarbonylamino, $C_3$-$C_6$cycloalkyloxy, halo, $C_1$-$C_3$haloalkoxy, $C_2$-$C_3$haloalkylamino, $C_2$-$C_3$haloalkylcarbonylamino, and hydroxy;

$R^5$ is selected from hydrogen, $C_1$-$C_3$alkyl, cyano, $C_3$cycloalkyl, and halo;

$R^6$ is selected from hydrogen, $C_1$-$C_3$alkyl, $C_1$-$C_3$alkylcarbonylamino, amino, $R^7$ is selected from hydrogen, $C_1$-$C_3$alkoxy, $C_1$-$C_3$alkyl, cyano, —$CH_2OH$, —$CH_2OCH_3$, $CH(CH_3)OH$, $C(CH_3)_2OH$, halo, and $C_1$-$C_3$haloalkyl;

$R^8$ is selected from hydrogen, $C_1$-$C_3$alkoxy, cyano, and halo;

$R^x$ and $R^y$, together with the nitrogen atom to which they are attached, form a three- to six-membered ring; and Y is selected from

[chemical structures of Y groups: azetidine, pyrrolidine, piperazine, piperidine, and morpholine rings bearing R⁹, R¹⁰, R¹¹ substituents]

wherein $R^9$ is selected from hydrogen, $C_1$-$C_6$alkyl, $C_3$-$C_6$cycloalkyl, and $C_1$-$C_6$alkylcarbonyl;

n is 0, 1, 2, or 3;

each $R^{10}$ is independently selected from hydrogen, $C_1$-$C_6$alkyl, aryl, aryl$C_1$-$C_3$alkyl, $C_3$-$C_6$cycloalkyl, halo, and $C_1$-$C_3$haloalkyl; and each $R^{11}$ is independently selected from hydrogen, $C_1$-$C_3$alkoxy and hydroxy.

In a first embodiment of the first aspect the present disclosure provides a compound of formula (I), or a pharmaceutically acceptable salt thereof, wherein $R^1$ and $R^2$ are each hydrogen.

In a second embodiment of the first aspect the present disclosure provides a compound of formula (I), or a pharmaceutically acceptable salt thereof, wherein wherein one of $R^1$ and $R^2$ is $C_1$-$C_3$alkyl and the other is selected from hydrogen and $C_1$-$C_3$alkyl.

In a third embodiment of the first aspect the present disclosure provides a compound of formula (I), or a pharmaceutically acceptable salt thereof, wherein one of $R^1$ and $R^2$ is hydrogen and the other is $C_3$-$C_6$cycloalkyl.

In a fourth embodiment of the first aspect the present disclosure provides a compound of formula (I), or a pharmaceutically acceptable salt thereof, wherein wherein $R^1$ and $R^2$ together are oxo; or $R^1$ and $R^2$, together with the carbon atom to which they are attached, form an oxetane ring.

In a second aspect the present disclosure provides a compound of formula (II):

[structure of formula (II): fused bicyclic with N, O, showing R¹, R², R⁴, R⁵, OR³ substituents] (II)

or a pharmaceutically acceptable salt thereof, wherein:

$R^1$ and $R^2$ are independently selected from hydrogen, $C_3$-$C_6$cycloalkyl, and $C_1$-$C_3$alkyl wherein the $C_1$-$C_3$alkyl is optionally substituted with one, two, or three groups independently selected from $C_1$-$C_3$alkoxy, $C_1$-$C_3$alkylamino, amino, cyano, $C_1$-$C_3$dialkylamino, halo, and hydroxy; or $R^1$ and $R^2$ together are oxo;

$R^3$ is $C_1$-$C_3$alkyl-Y or $C_2$-$C_8$alkyl, wherein the $C_2$-$C_8$alkyl is optionally substituted with one, two, or three groups independently selected from $C_1$-$C_3$alkoxy, $C_1$-$C_3$alkylamino, $C_1$-$C_3$alkoxyC$_2$-$C_{1-3}$alkylamino, amino, aryl, halo, $C_1$-$C_3$haloalkylamino, $C_1$-$C_3$haloalkylcarbonylamino, hydroxy, —NR$^x$R$^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxyC$_2$-$C_{1-3}$alkylamino, amino, aryl, aryl$C_1$-$C_3$alkyl, halo, $C_1$-$C_3$haloalkyl, $C_1$-$C_3$haloalkylamino and hydroxy;

$R^4$ is selected from hydrogen, $C_1$-$C_3$alkoxy, $C_1$-$C_3$alkoxycarbonylamino, $C_1$-$C_3$alkyl, $C_1$-$C_3$alkylamino, $C_1$-$C_3$alkylcarbonylamino, amino, arylamino, arylcarbonylamino, $C_3$-$C_6$cycloalkylamino, $C_3$-$C_6$cycloalkylcarbonylamino, $C_3$-$C_6$cycloalkyloxy, halo, $C_1$-$C_3$haloalkoxy, $C_2$-$C_3$haloalkylamino, $C_2$-$C_3$haloalkylcarbonylamino, and hydroxy;

$R^5$ is selected from hydrogen, $C_1$-$C_3$alkyl, cyano, $C_3$cycloalkyl, and halo;

$R^x$ and $R^y$, together with the nitrogen atom to which they are attached, form a three- to six-membered ring; and Y is selected from

[chemical structures of Y groups: azetidine, pyrrolidine, piperazine, piperidine, and morpholine rings bearing R⁶, R⁷, R⁸ substituents]

wherein $R^6$ is selected from hydrogen, $C_1$-$C_6$alkyl, $C_3$-$C_6$cycloalkyl, and $C_1$-$C_6$alkylcarbonyl;

n is 0, 1, 2, or 3;

each $R^7$ is independently selected from hydrogen, $C_1$-$C_6$alkyl, aryl, aryl$C_1$-$C_3$alkyl, $C_3$-$C_6$cycloalkyl, halo, and $C_1$-$C_3$haloalkyl; and each $R^8$ is independently selected from hydrogen, $C_1$-$C_3$alkoxy and hydroxy.

In a third aspect the present disclosure provides composition comprising a pharmaceutically acceptable amount of a compound of formula (I), or a pharmaceutically acceptable salt thereof, and a pharmaceutically acceptable carrier.

In a fourth aspect the present disclosure provides a method of inhibiting adaptor associated kinase 1 (AAK1) activity, comprising contacting AAK1 with a compound of formula (I), or a pharmaceutically acceptable salt thereof.

In a fifth aspect the present disclosure provides a method for treating or managing a disease or a disorder mediated by AAK1 activity, the method comprising administering to a patient in need thereof a therapeutically effective amount of a compound of formula (I), or a pharmaceutically acceptable salt thereof. In a first embodiment of the fifth aspect the disease or disorder is selected from Alzheimer's disease, bipolar disorder, pain, Parkinson's disease, and schizophrenia. In a second embodiment of the fifth aspect the pain is neuropathic pain. In a third embodiment of the fifth aspect the neuropathic pain is fibromyalgia or peripheral neuropathy.

Other aspects of the present disclosure may include suitable combinations of embodiments disclosed herein.

Yet other aspects and embodiments may be found in the description provided herein.

BRIEF DESCRIPTION OF THE FIGURES

Aspects of the disclosure are illustrated in FIG. 1, which shows results obtained from a formalin pain model using AAK1 homozygous (−/−) knockout mice and their wild-type (+/+) littermates. The AAK1 homozygous (−/−) knockout mice show a clear reduction in both acute and tonic pain response as compared to their wild-type (+/+) littermates.

This disclosure is based, in part, on the discovery that AAK1 knockout mice exhibit a high resistance to pain. That discovery prompted research that ultimately led to the discovery of AAK1 inhibitors, compositions comprising them, and methods of their use.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^{10}$ groups may be the same or different.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

In some instances, the number of carbon atoms in any particular group is denoted before the recitation of the group. For example, the term "$C_{1-6}$ alkyl" denotes an alkyl group containing one to six carbon atoms. Where these designations exist they supercede all other definitions contained herein.

Asymmetric centers may exist in the compounds of the present disclosure. It should be understood that the disclosure encompasses all stereochemical isomeric forms, or mixtures thereof, which possess the ability to inhibit AAK1. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

One embodiment of this disclosure encompasses methods of inhibiting adaptor associated kinase 1 (AAK1), both in vitro and in vivo, which comprise contacting AAK1 with a compound of formula I or a pharmaceutically acceptable salt thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. Unless otherwise indicated, a "therapeutically effective amount" of a compound is an amount sufficient to provide a therapeutic benefit in the treatment or management of a disease or condition, or to delay or minimize one or more symptoms associated with the disease or condition. The term "therapeutically effective amount" can encompass an amount that improves overall therapy, reduces or avoids symptoms or causes of a disease or condition, or enhances the therapeutic efficacy of another therapeutic agent.

The term "therapeutically effective amount," as used herein, refers to an amount of a compound or compounds sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Compounds of the disclosure may be administered in combination with one or more additional therapeutic or prophylactic agents. For example, when used for the treatment of pain, possible additional agents include immunosuppressive agents, anti-inflammatory agents, and/or other agents used in the treatment of pain.

Immunosuppressants suitable for use in the methods and compositions of this disclosure include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples of immunosuppressants include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Other immunosuppressants include inosine monophosphate dehydrogenase inhibitors, such as mycophenolate mofetil (CellCept®) and mycophenolic acid (Myfortic®).

Anti-inflammatory drugs suitable for use in the methods and compositions of this disclosure include those known in the art. Examples include glucocorticoids and NSAIDs. Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include, but are not limited to, agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the disclosure may be administered in combination with one or more additional therapeutic or prophylactic agents directed at the underlying disease or condition. For example, when used to treat diabetic neuropathy, compounds of the disclosure may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals. Unless otherwise indicated, the terms "manage," "managing", and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: RT or rt or r.t. for room temperature; $t_R$ for retention time; min or mins for minutes; h or hr or hrs for hours; MeOD for $CD_3OD$; THF for tetrahydrofuran; ACN or MeCN for acetonitrile; DCM for dichloromethane; MeOH for methanol; EtOH for ethanol; t-BuOH for t-butanol, DMSO for dimethylsulfoxide; DMF for N,N-dimethylformamide; EtOAc for ethyl acetate; BOC or Boc for tert-butoxycarbonyl; Me for methyl; Et for ethyl; Cyc-Pr for cyclopropyl; phth for phthaloyl; Ac for acetyl; Ph for phenyl; DPPA for diphenylphosphoryl azide; $Et_3N$ or TEA for triethylamine; n-BuLi for n-butyllithium; TFA for trifluoroacetic acid; NBS for N-bromosuccinimide; NCS for N-chlorosuccinimide; NIS for N-iodosuccinimide; DEA for diethylamine; LDA for lithium diisopropylamide; LAH for lithium aluminum hydride; DBU for 1,8-diazabicycloundec-7-ene; DMAP for N,N-dimethylaminopyridine; DPPF or dppf for 1,1'-bis(diphenylphosphanyl) ferrocene; LDA for lithium diisopropylamide; NBS for N-bromosuccinimide; TMS for trimethylsilyl; TBAF for tetrabutylammonium fluoride; NCS for N-chlorosuccinimide; TFA for trifluoracetic acid; NIS for N-iodosuccinimide; and Ac for acetyl.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being affected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of formula 6, wherein $R^1$ and $R^2$ are H, alkyl, cycloalkyl or alkenyl, are prepared by the methods outlined in Scheme 1. The appropriate sodium phenolate can be alkylated with a suitably substituted propargyl halide at ambient temperature to provide the desired propargyl ether 2. Wittig reaction of the aldehyde function in 2 with appropriate Wittig reagent can result in the formation of the desired olefin as mixture of E, Z mixture with the E-isomer being the major product. The α,β-unsaturated aldehyde isomeric mixture 3 thus obtained can be converted to hydrazone derivative 4 by reaction with 1,1-dimethylhydrazine in a solvent such as dichloromethane in presence of a dehydrating agent such as MgSO$_4$. The crude hydrazone 4 thus obtained can be subjected to an intramolecular [4+2] cycloaddition reaction in presence of a radical scavenger such as 2,6-di-tert-butyl-4-methylphenol in a solvent such as mesitylene (Dolle, R. E. et. al. *Tetrahedron Lett.* 1988, 29, 6349-6352) to provide the cyclization product 5. The bromide in 5 can be replaced by reaction with an alcohol in a palladium catalyzed coupling reaction using reaction conditions familiar to those skilled in the art following procedures such as those described by Gowrisankar, et. al. *J. Am. Chem. Soc.* 2010, 132, 11592-11598. For the purpose of preparing ethers represented by 6 from bromides 5, any other functional groups in $R^3OH$ capable of interfering in Pd coupling reaction can be protected with an appropriate protecting group reagent as described in *Protective Groups in Organic Synthesis* (Greene, Wuts; 3$^{rd}$ ed., 1999, John Wiley & Sons, Inc.). These protecting groups can subsequently be unmasked by the methods described in the same reference above. For example, the amino group can be protected as a phthalimido derivative which after Pd coupling reaction to provide 7 can be unmasked by treatment with hydrazine in ethanol as shown in Scheme 1 to provide 8.

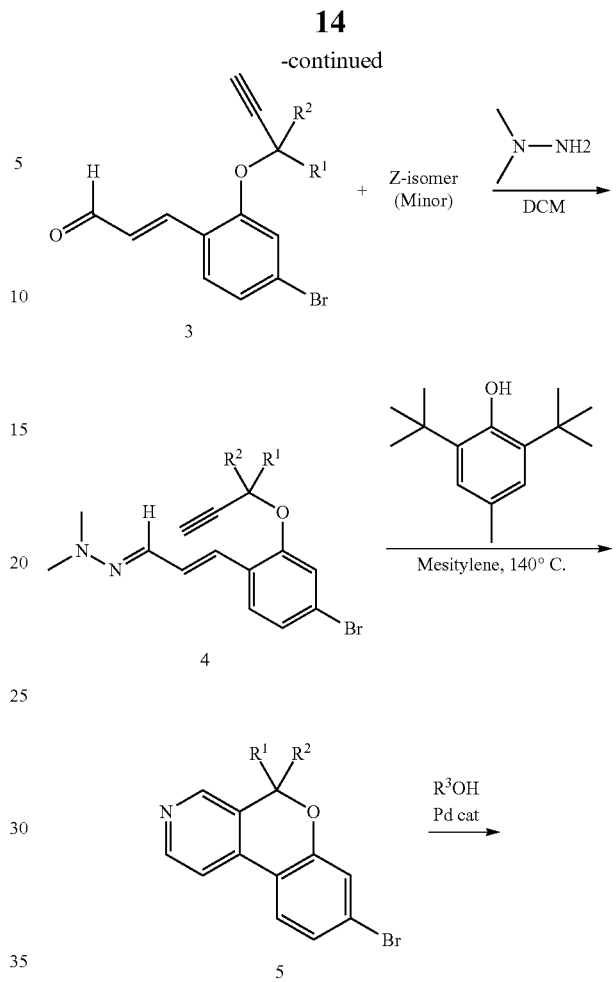

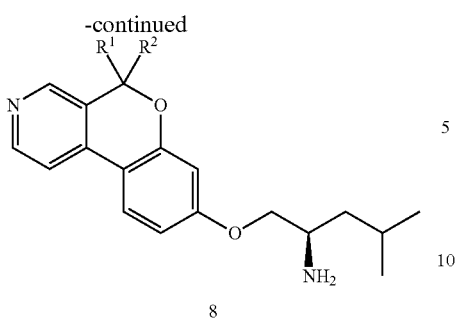

8

Compounds of formula 17, wherein $R^1$ is H, alkyl, alkenyl, $R^5$ is H, halo, CN and $R^3$ is H, alkyl, cycloalkyl, are prepared by the methods outlined in Scheme 2. 4-Bromopyridine or 4-chloropyridine hydrochloride salt can be subjected to base mediated formylation with a base such as lithium diisopropylamide to give the corresponding 3-formyl pyridine as described by Knutsen, L. et. al. (*Bioorganic & Medicinal Chemistry Letters,* 2007, 17, 662-667). The aldehyde 9, so obtained can be subjected to Suzuki cross coupling reaction with an appropriate coupling partner such as fluoroboronic acid 11, under standard Suzuki conditions employing a base such as cesium carbonate and a catalyst such as $Pd(PPh_3)_4$ as described by Zhang, Lei et. al. (*Journal of Medicinal Chemistry,* 2011, 54, 1724-1739). The biaryl aldehyde 10, can then be reduced to the corresponding primary alcohol 12 ($R^1$=H) with a standard reducing agent such as sodium borohydride. To form the secondary alcohols 12 ($R^1$=alkyl, cycloalkyl or alkenyl), the aldehyde 10, can be treated with an appropriate Grignard reagent in a solvent such as anhydrous tetrahydrofuran at low temperature (previously described by Itoh, Toshiyuki et. al. *Chemistry-A European Journal,* 2006, 12, 9228-9237 and Zhang, et. al. *Tetrahedron Lett.,* 2010, 51, 3927-3930). The primary or secondary alcohols 12, upon treatment with a hydride source such as sodium hydride in a solvent such as THF under inert atmosphere can afford the constrained halo-substituted core, 13. Among the compounds represented by formula 13, the alkenyl substituted ($R^1$=vinyl), compound can be hydrogenated using standard hydrogenation conditions such as treatment with palladium on carbon under a hydrogen atmosphere to provide the corresponding alkyl substituted analogues. Compounds of formula 13 can then be subjected to palladium catalyzed ether synthesis including reaction conditions familiar to those skilled in the art following procedures such as those described by Gowrisankar, et. al. (*J. Am. Chem. Soc.* 2010, 132, 11592-11598). The reactions can be performed using appropriately protected, optically pure (S) or (R)-aminoalcohols to afford optically pure ethers 14. Compounds of formula 15 wherein $R^5$ is halo can be prepared by treatment of 14 with a halogenating agent such as N-bromosuccinamide, N-chlorosuccinamide or N-iodosuccinamide as the case may be. Compound of formula 16 wherein $R^5$ is cyano can be prepared from the corresponding halo compound via copper catalyzed coupling reactions, reaction conditions familiar to those skilled in the art (J. E. Callen, *Organic syntheses, CV* 3, 1955, 212). Alternatively, a cyano group can be introduced with zinc cyanide via standard Negishi coupling conditions in the presence of a catalyst such as $Pd(PPh_3)_4$, $Pd_2(dba)_3$, or $PdCl2(PPh_3)_2$, with or without a ligand such as DPPF in a solvent such as toluene, dichloroethane, THF, DMF, methanol, ethanol, water or a combination thereof at temperatures ranging from 20° C. to 150° C. For the purpose of preparing ethers represented by 14 from chlorides 13, or cyanides represented by 16 from haldies 15, any other functional groups in $R^3OH$ capable of interfering in Cu or Pd coupling reactions can be protected with an appropriate protecting group reagent as described in Protective Groups in Organic Synthesis (Greene, Wuts; 3rd ed., 1999, John Wiley & Sons, Inc.). These protecting groups can subsequently be unmasked by the methods described in the same reference above. Diastereomeric mixtures so obtained could be resolved using preparative chiral HPLC or preparative chiral SFC techniques.

Scheme 2

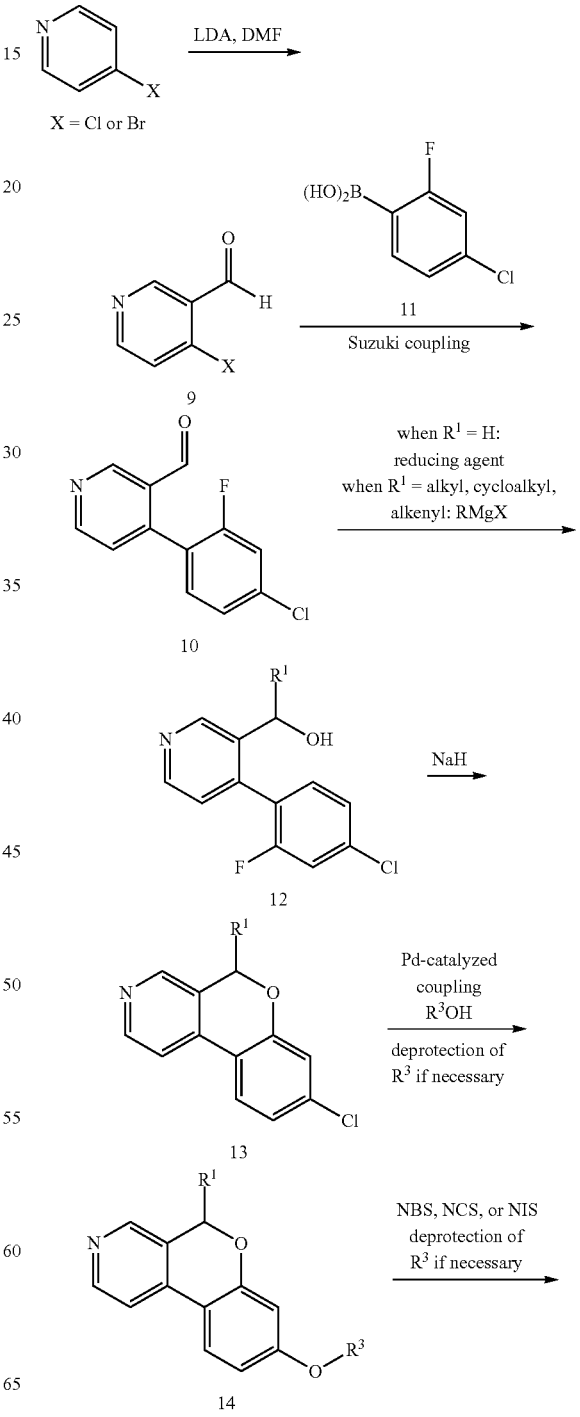

-continued

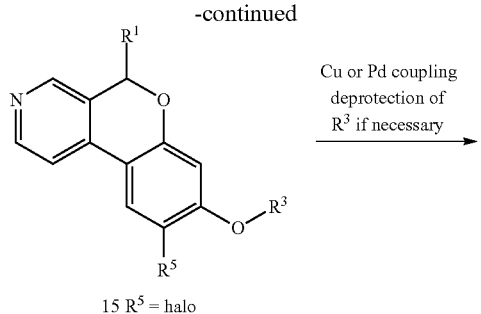

15 R⁵ = halo

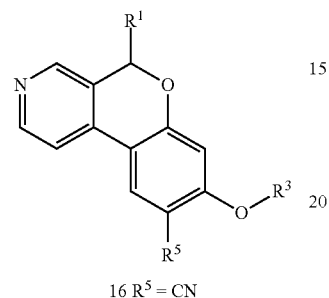

16 R⁵ = CN

Compounds of formula 23 are prepared by the methods outlined in Scheme 3. 4-Chloropyridine pyridine 3-carboxylic acid 17 (where $R^6$=H or alkyl) can be converted to the corresponding ester 18 using methods as described in *Protective Groups in Organic Synthesis* (Greene, Wuts; 3$^{rd}$ ed., 1999, John Wiley & Sons, Inc.). The ester can then be subjected to Suzuki cross coupling reaction with an appropriate coupling partner such as fluoroboronic acid 11, under standard Suzuki conditions employing a base such as cesium carbonate and a catalyst such as Pd(PPh₃)₄ as described by Zhang, Lei et. al. (*Journal of Medicinal Chemistry,* 2011, 54, 1724-1739) for compounds represented by formula 19. The biaryl ester 19 can be subjected to hydrolysis to yield corresponding carboxylic acid 20 under standard saponification conditions using a base such as sodium hydroxide or lithium hydroxide in a solvent such as methanol, water, THF, or a combination thereof. The acid can then be heated under basic conditions to yield lactone 21. The lactone can be subjected to palladium catalyzed ether synthesis using reaction conditions familiar to those skilled in the art following procedures such as those described by Gowrisankar, et. al. (*J. Am. Chem. Soc.* 2010, 132, 11592-11598). The reactions can be performed using appropriately protected, optically pure (S) or (R)-aminoalcohols to afford optically pure ethers. For the purpose of preparing ethers represented by 22 from halides 21, any other functional groups in R³OH capable of interfering in Pd coupling reactions can be protected with an appropriate protecting group reagent as described in Protective Groups in Organic Synthesis (Greene, Wuts; 3rd ed., 1999, John Wiley & Sons, Inc.). Compounds of formula 22 where in R⁵=halo can be prepared by halogenation of the corresponding ether using a halogenating agent such as N-chlorosuccinamide. If necessary, the ether analogues can be subjected to deprotection of the side chain amino group using appropriate conditions as described in Protective *Groups in Organic Synthesis* (Greene, Wuts; 3$^{rd}$ ed., 1999, John Wiley & Sons, Inc.) to yield compounds of formula 23.

Scheme 3

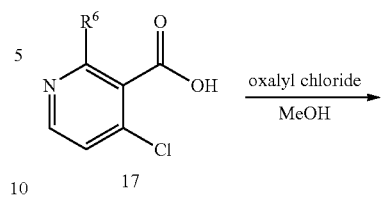

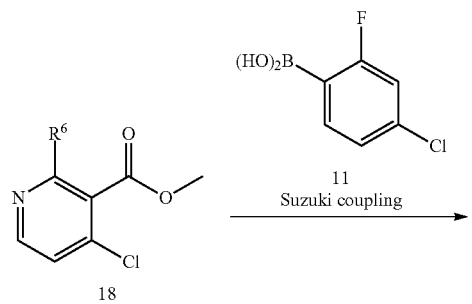

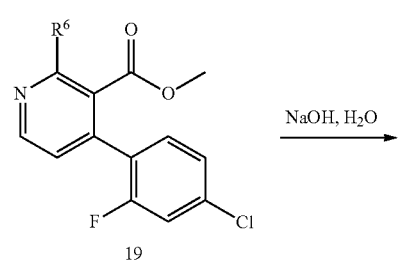

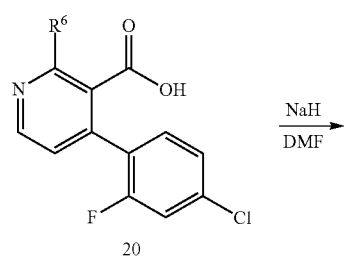

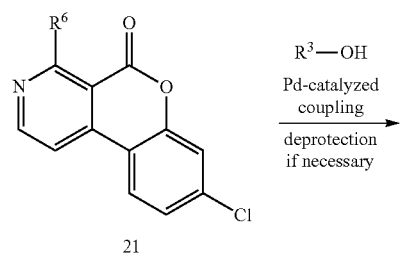

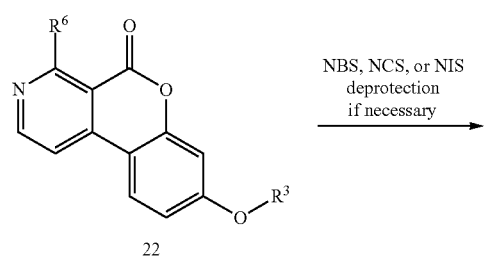

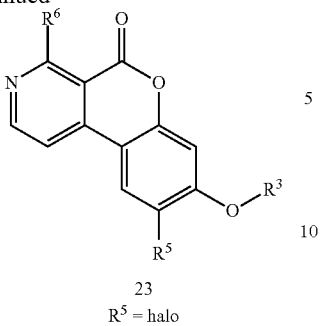

23
R[5] = halo

Compounds of formula 32 and 33, wherein R[6] is NH$_2$ or NHAc, are prepared by the methods outlined in Scheme 4. The synthesis can begin with Curtius rearrangement of 4-chloropyridine-2-carboxylic acid 24 to yield N-Boc-2-amino-4-chloropyridine 25 as described Leslie et. al. (*Australian Journal of Chemistry*, 1982, 35, 2025-2034). Directed ortho-metallation followed by treatment with dimethylformamide can furnish the pyridine aldehyde derivative 26 using methods such as those described by Charles et. al. (*J. Med. Chem.*, 2010, 53, 3330-3348). The aldehyde can then be subjected to Suzuki cross coupling reaction with an appropriate coupling partner such as fluoroboronic acid 11, under standard Suzuki conditions employing a base such as cesium carbonate and a catalyst such as Pd(PPh$_3$)$_4$ as described by Zhang, Lei et. al. (*Journal of Medicinal Chemistry*, 2011, 54, 1724-1739) to give 27. Removal of the protecting group on the amine using appropriate conditions as described in Protective *Groups in Organic Synthesis* (Greene, Wuts; 3rd ed., 1999, John Wiley & Sons, Inc.) followed by reduction of the aldehyde 28 mediated by an agent such as sodium borohydride (Eisai R&D Management Co., Ltd. Patent: EP1782811 A1, 2007) can provide alcohol 29. To form the secondary alcohols 29 (R[1]=alkyl), the aldehyde 28, can be treated with an appropriate Grignard reagent in a solvent such as anhydrous tetrahydrofuran at low temperature (previously described by Itoh, Toshiyuki et. al. *Chemistry-A European Journal*, 2006, 12, 9228-9237 and Zhang, et. al. *Tetrahedron Lett.*, 2010, 51, 3927-3930). Cyclization mediated by a base such as sodium hydride can lead to intermediate 30. The base catalyzed acetylation with acetyl chloride in a solvent such as dichloromethane with a base such as pyridine can provide 31. The aryl chloride 31 can then be subjected to a palladium catalyzed ether synthesis using reaction conditions familiar to those skilled in the art following procedures such as those described by Gowrisankar, et al. (*J. Am. Chem. Soc.* 2010, 132, 11592-11598) to provide the corresponding aryl ether. For the purpose of preparing ethers represented by 32 from halides 31, any other functional groups in R[3]OH capable of interfering in Pd coupling reactions can be protected with an appropriate protecting group reagent as described in Protective Groups in Organic Synthesis (Greene, Wuts; 3rd ed., 1999, John Wiley & Sons, Inc.). Removal of the protecting group can be achieved using appropriate conditions as described in the same reference to afford compounds of formula 32 wherein R[6] is NHAc. The N-acetyl group can be removed by hydrolysis using a base such as potassium hydroxide to provide compounds of formula 33 wherein R[6] is NH$_2$.

Scheme 4

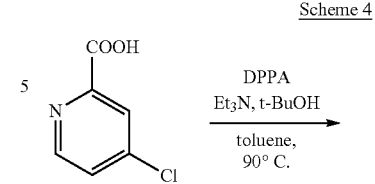

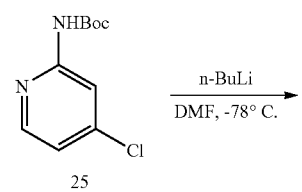

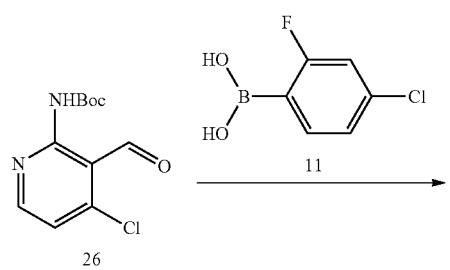

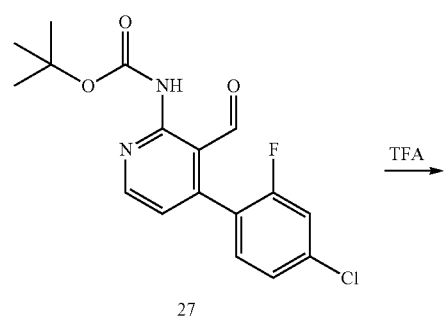

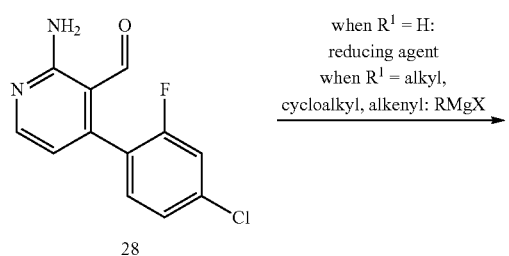

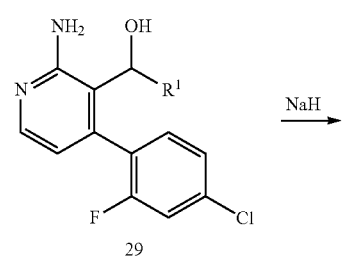

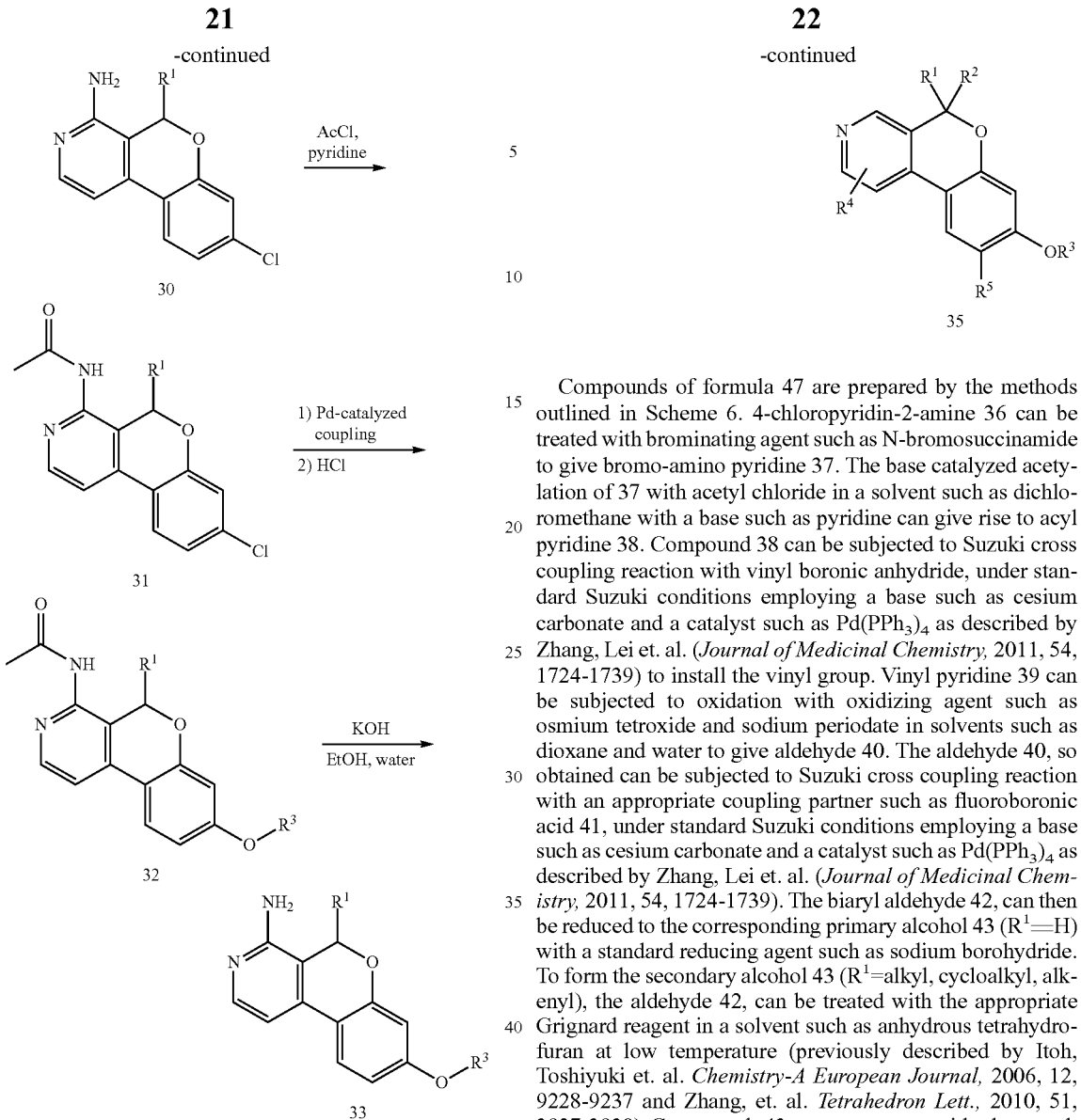

Compounds of formula 35, wherein $R^5$ is halo are prepared by the methods outlined in Scheme 5. The ether analogues represented by 34 can be prepared as in Scheme 2 and treated with a halogenating agent such as N-halosuccinamide to install a halogen at $R^5$. Deprotection of the side chain amino group using appropriate conditions as described in *Protective Groups in Organic Synthesis* (Greene, Wuts; 3$^{rd}$ ed., 1999, John Wiley & Sons, Inc.) can yield compounds represented by formula 33 wherein $R^5$ is halo.

Scheme 5

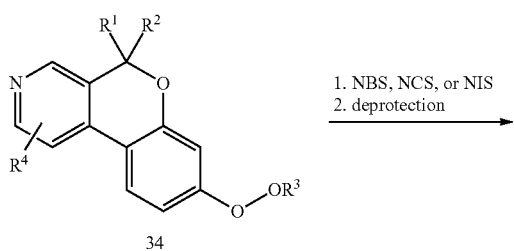

Compounds of formula 47 are prepared by the methods outlined in Scheme 6. 4-chloropyridin-2-amine 36 can be treated with brominating agent such as N-bromosuccinamide to give bromo-amino pyridine 37. The base catalyzed acetylation of 37 with acetyl chloride in a solvent such as dichloromethane with a base such as pyridine can give rise to acyl pyridine 38. Compound 38 can be subjected to Suzuki cross coupling reaction with vinyl boronic anhydride, under standard Suzuki conditions employing a base such as cesium carbonate and a catalyst such as Pd(PPh$_3$)$_4$ as described by Zhang, Lei et. al. (*Journal of Medicinal Chemistry*, 2011, 54, 1724-1739) to install the vinyl group. Vinyl pyridine 39 can be subjected to oxidation with oxidizing agent such as osmium tetroxide and sodium periodate in solvents such as dioxane and water to give aldehyde 40. The aldehyde 40, so obtained can be subjected to Suzuki cross coupling reaction with an appropriate coupling partner such as fluoroboronic acid 41, under standard Suzuki conditions employing a base such as cesium carbonate and a catalyst such as Pd(PPh$_3$)$_4$ as described by Zhang, Lei et. al. (*Journal of Medicinal Chemistry*, 2011, 54, 1724-1739). The biaryl aldehyde 42, can then be reduced to the corresponding primary alcohol 43 ($R^1$=H) with a standard reducing agent such as sodium borohydride. To form the secondary alcohol 43 ($R^1$=alkyl, cycloalkyl, alkenyl), the aldehyde 42, can be treated with the appropriate Grignard reagent in a solvent such as anhydrous tetrahydrofuran at low temperature (previously described by Itoh, Toshiyuki et. al. *Chemistry-A European Journal*, 2006, 12, 9228-9237 and Zhang, et. al. *Tetrahedron Lett.*, 2010, 51, 3927-3930). Compounds 43, upon treatment with a base such as sodium hydride at ambient temperature or with base such as potassium carbonate under heating conditions, in a solvent such as THF under inert atmosphere can afford the constrained chloro-substituted core 44. Compound of formula 44 where in R=Me can be prepared by methylation of corresponding core 44 (R=COOH) using base such as sodium hydride and alkylating agent such as methyl iodide in solvent such as THF at low temperature. Compounds of formula 44 where in R=COcyc-Pr, CO(OCH$_3$) can be prepared by deacylation of 44 (R=COCH$_3$) with reagent such as potassium hydroxide in solvents such as water and methanol, followed by acylation with corresponding acid chlorides in the presence of base such as pyridine based on the protection and deprotection procedures described in *Protective Groups in Organic Synthesis* (Greene, Wuts; 3$^{rd}$ ed., 1999, John Wiley & Sons, Inc.). Compounds of formula 44 can then be subjected to palladium catalyzed ether synthesis including reaction conditions familiar to those skilled in the art following procedures such as those described by Gowrisankar, et. al. (*J. Am. Chem. Soc.* 2010, 132, 11592-11598). The reactions can be performed, for example, using appropriately protected racemic or optically pure (S) or (R)-aminoalcohols to afford racemic or optically pure ethers respectively. For the purpose of preparing ethers represented by 45 from halides 44, any other functional groups in R³OH capable of interfering in Pd coupling reactions, such as the amino group of an aminoalcohol, can be protected with an appropriate protecting group reagent as described in Protective Groups in Organic Synthesis (Greene, Wuts; 3rd ed., 1999, John Wiley & Sons, Inc.). Removal of the protecting group can be achieved using appropriate conditions as described in the same reference to afford compounds of formula 47. Compound of formula 46 where in R⁵=halo can be prepared by halogenation of the corresponding ether (R⁵=H) using halogenating agent such as N-chlorosuccinamide. The ether analogues represented by compounds compounds 46 obtained via palladium catalyzed reactions, can be subjected to deprotection of R³ if necessary using appropriate conditions as described in *Protective Groups in Organic Synthesis* (Greene, Wuts; 3$^{rd}$ ed., 1999, John Wiley & Sons, Inc.) to yield compounds represented by formula 47. The diastereomeric mixtures so obtained could be resolved using preparative chiral HPLC or preparative chiral SFC techniques.

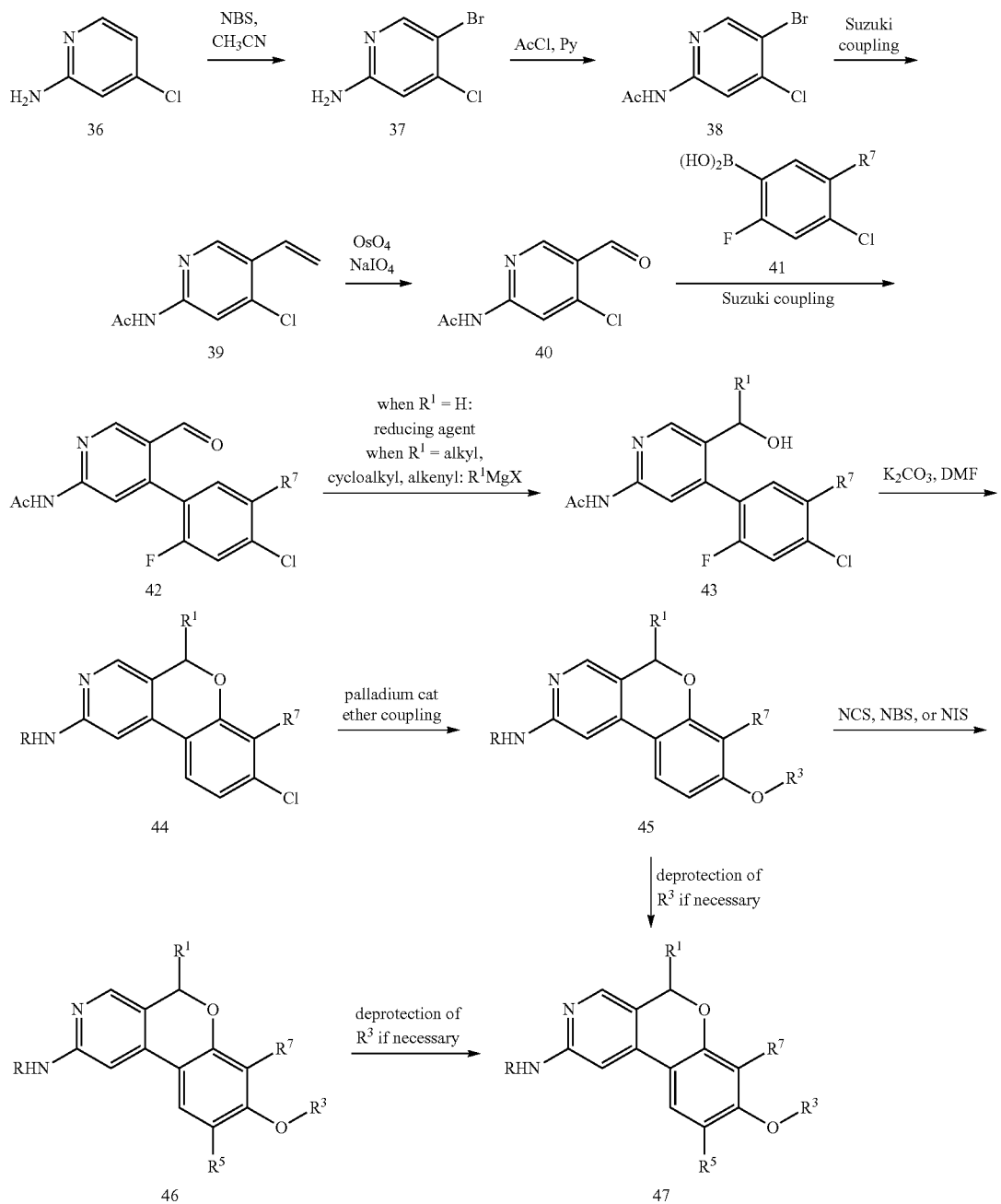

Compounds of formula 53 are prepared by the methods outlined in Scheme 7. Substituted 4-bromopyridine or 4-chloropyridine can be subjected to base mediated carboxylation with a base such as lithium diisopropylamide and dry ice to give the corresponding pyridine-3-carboxylic acid 48. The acid can be esterified using standard conditions known to those skilled in the art, such as treatment with a base such as DBU and an alkylating agent such as methyl iodide to give esters represented by the formula 49. The halopyrine, 49, can then be subjected to Suzuki cross coupling reaction with an appropriate coupling partner such as fluoroboronic acid 11, under standard Suzuki conditions employing a base such as cesium carbonate and a catalyst such as $Pd(PPh_3)_4$ as described by Zhang, Lei et. al. (*Journal of Medicinal Chemistry*, 2011, 54, 1724-1739) for compounds represented by formula 50. The ester can be converted to the corresponding alcohol represented by formula 51 by treatment with a reducing agent such as LAH. The alcohol, upon treatment with a hydride source such as sodium hydride in a solvent such as THF under inert atmosphere can afford the constrained halo-substituted core, 52. Compounds of formula 52 can then be subjected to palladium catalyzed ether synthesis including reaction conditions familiar to those skilled in the art following procedures such as those described by Gowrisankar, et. al. (*J. Am. Chem. Soc.* 2010, 132, 11592-11598). For the purpose of preparing ethers represented by 53 from chlorides 52 any other functional groups in $R^3OH$ capable of interfering in Pd coupling reactions can be protected with an appropriate protecting group reagent as described in Protective Groups in Organic Synthesis (Greene, Wuts; 3rd ed., 1999, John Wiley & Sons, Inc.). These protecting groups can subsequently be unmasked by the methods described in the same reference above.

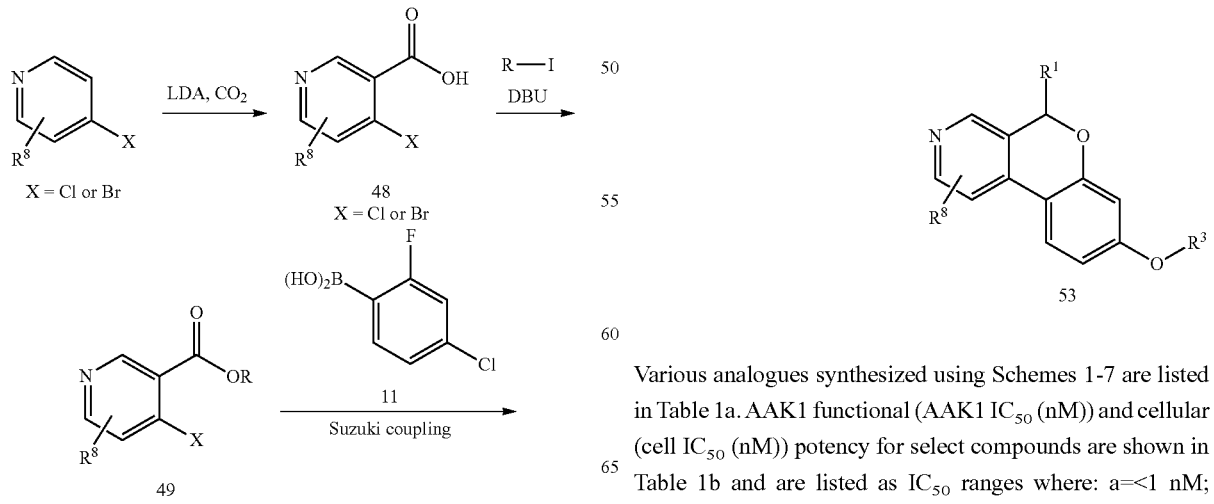

Various analogues synthesized using Schemes 1-7 are listed in Table 1a. AAK1 functional (AAK1 $IC_{50}$ (nM)) and cellular (cell $IC_{50}$ (nM)) potency for select compounds are shown in Table 1b and are listed as $IC_{50}$ ranges where: a=<1 nM; b=1-10 nM; c=10-100 nM; d=100-1000 nM.

TABLE 1a
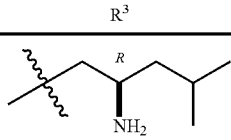
(I)
| Ex | Stereochem | R¹ | R² | R⁴ | R⁵ | R⁶ | R⁷ | R⁸ | R³ |
|---|---|---|---|---|---|---|---|---|---|
| 1 | R | H | H | H | H | H | H | H | 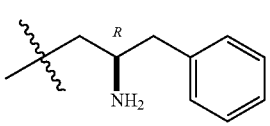 |
| 2 | R | H | H | H | H | H | H | H | 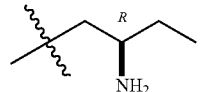 |
| 3 | R | H | H | H | H | H | H | H | 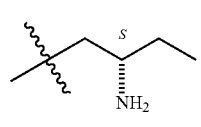 |
| 4 | S | H | H | H | H | H | H | H | 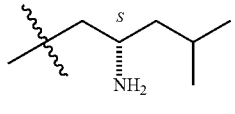 |
| 5 | S | H | H | H | H | H | H | H | 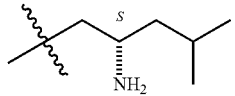 |
| 6 | diastereomers | Me | H | H | H | H | H | H | 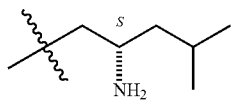 |
| 6a | Dia-1 | Me | H | H | H | H | H | H | 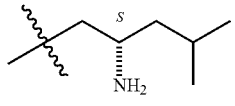 |
| 6b | Dia-2 | H | Me | H | H | H | H | H | 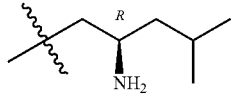 |
| 7a | Dia-1 | Me | H | H | H | H | H | H | 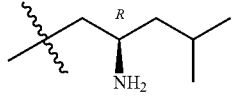 |
| 7b | Dia-2 | H | Me | H | H | H | H | H | 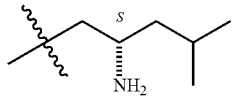 |
| 8 | diastereomers | Cyc-Pr | H | H | H | H | H | H |  |

TABLE 1a-continued

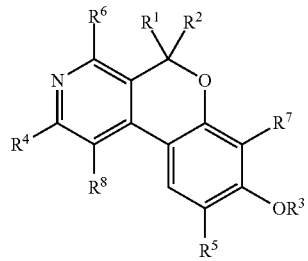

(I)

| Ex | Stereo-chem | R¹ | R² | R⁴ | R⁵ | R⁶ | R⁷ | R⁸ | R³ |
|---|---|---|---|---|---|---|---|---|---|
| 8a | Dia-1 | Cyc-Pr | H | H | H | H | H | H | (S)-CH₂CH(NH₂)CH₂CH(CH₃)₂ |
| 8b | Dia-2 | H | Cyc-Pr | H | H | H | H | H | (S)-CH₂CH(NH₂)CH₂CH(CH₃)₂ |
| 9 | diastereomers | Cyc-Pr | H | H | H | H | H | H | (R)-CH₂CH(NH₂)CH₂CH(CH₃)₂ |
| 9a | Dia-1 | Cyc-Pr | H | H | H | H | H | H | (R)-CH₂CH(NH₂)CH₂CH(CH₃)₂ |
| 9b | Dia-2 | H | Cyc-Pr | H | H | H | H | H | (R)-CH₂CH(NH₂)CH₂CH(CH₃)₂ |
| 10 | diastereomers | Et | H | H | H | H | H | H | (S)-CH₂CH(NH₂)CH₂CH(CH₃)₂ |
| 10a | Dia-1 | Et | H | H | H | H | H | H | (S)-CH₂CH(NH₂)CH₂CH(CH₃)₂ |
| 10b | Dia-2 | H | Et | H | H | H | H | H | (S)-CH₂CH(NH₂)CH₂CH(CH₃)₂ |
| 11 | S | | =O | H | H | H | H | H | (S)-CH₂CH(NH₂)CH₂CH(CH₃)₂ |
| 12 | S | H | H | H | H | NHAc | H | H | (S)-CH₂CH(NH₂)CH₂CH(CH₃)₂ |
| 13 | S | H | H | H | H | NH₂ | H | H | (S)-CH₂CH(NH₂)CH₂CH(CH₃)₂ |

TABLE 1a-continued

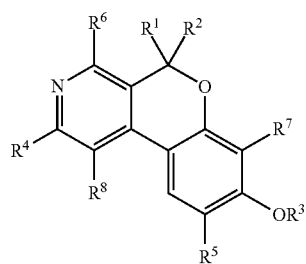

(I)

| Ex | Stereo-chem | R¹ | R² | R⁴ | R⁵ | R⁶ | R⁷ | R⁸ | R³ |
|---|---|---|---|---|---|---|---|---|---|
| 14 | S | H | H | H | Br | H | H | H | ⁓⁓CH(CH₂CH(CH₃)₂)NH₂ (S), isobutyl |
| 15 | S | Me | H | H | H | NH2 | H | H | ⁓⁓CH(CH₂CH(CH₃)₂)NH₂ (S) |
| 16 | S | H | H | H | H | H | H | F | ⁓⁓CH(CH₂CH(CH₃)₂)NH₂ (S) |
| 17 | Racemate | H | H | H | H | H | H | H | ⁓⁓CH(CH₂CH₂CF₃)NH₂ branched |
| 18 | S | H | H | NHAc | H | H | H | H | ⁓⁓CH(CH₂CH(CH₃)₂)NH₂ (S) |
| 19 | S | oxetane (R¹,R² together) | | H | H | H | H | H | ⁓⁓CH(CH₂CH(CH₃)₂)NH₂ (S) |
| 20 | S | CH2OH | CH2Cl | H | H | H | H | H | ⁓⁓CH(CH₂CH(CH₃)₂)NH₂ (S) |
| 21 | S | Me | H | H | Br | H | H | H | ⁓⁓CH(CH₂CH(CH₃)₂)NH₂ (S) |
| 22 | S | Me | H | H | CN | H | H | H | ⁓⁓CH(CH₂CH(CH₃)₂)NH₂ (S) |
| 23 | S | H | H | H | CN | H | H | H | ⁓⁓CH(CH₂CH(CH₃)₂)NH₂ (S) |

TABLE 1a-continued

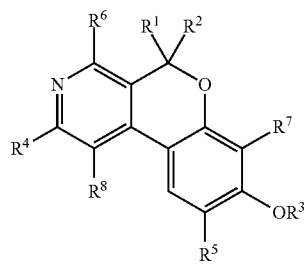

(I)

| Ex | Stereo-chem | R¹ | R² | R⁴ | R⁵ | R⁶ | R⁷ | R⁸ | R³ |
|---|---|---|---|---|---|---|---|---|---|
| 24 | diastereomers | Me | H | H | H | H | H | H | -CH₂-CH(NH₂)-CH₂-cyclopentyl |
| 25 | S | =O | | H | Br | H | H | H | -CH₂-CH(S)(NH₂)-CH₂-CH(CH₃)₂ |
| 26 | diastereomers | Me | H | H | H | H | H | H | -CH₂-CH(NH₂)-CH₂-C(CH₃)₂F |
| 27 | diastereomers | CF3 | H | H | Cl | H | H | H | -CH₂-CH(S)(NH₂)-CH₂-CH(CH₃)₂ |
| 27a | Dia-1 | CF3 | H | H | Cl | H | H | H | -CH₂-CH(S)(NH₂)-CH₂-CH(CH₃)₂ |
| 27b | Dia-2 | CF3 | H | H | Cl | H | H | H | -CH₂-CH(S)(NH₂)-CH₂-CH(CH₃)₂ |
| 28 | diastereomers | CF3 | H | H | Br | H | H | H | -CH₂-CH(S)(NH₂)-CH₂-CH(CH₃)₂ |
| 29 | diastereomers | Me | H | NH2 | H | H | H | H | -CH₂-CH(S)(NH₂)-CH₂-CH(CH₃)₂ |
| 30 | diastereomers | Me | H | NHAc | H | H | H | H | -CH₂-CH(S)(NH₂)-CH₂-CH(CH₃)₂ |
| 31a | Dia-1 | H | Me | H | I | H | H | H | -CH₂-CH(S)(NH₂)-CH₂-CH(CH₃)₂ |
| 31b | Dia-2 | Me | H | H | I | H | H | H | -CH₂-CH(S)(NH₂)-CH₂-CH(CH₃)₂ |

TABLE 1a-continued (I)

| Ex | Stereo-chem | R¹ | R² | R⁴ | R⁵ | R⁶ | R⁷ | R⁸ | R³ |
|---|---|---|---|---|---|---|---|---|---|
| 32 | S | H | H | NHAc | Cl | H | H | H | (S)-4-methylpentan-2-yl, 2-NH₂ |
| 33 | S | H | H | NH₂ | H | H | H | H | (S)-4-methylpentan-2-yl, 2-NH₂ |
| 34 | S | =O | | H | H | Me | H | H | (S)-4-methylpentan-2-yl, 2-NH₂ |
| 35 | S | H | H | NHAc | H | H | Me | H | (S)-4-methylpentan-2-yl, 2-NH₂ |
| 36 | Racemate | H | H | NHAc | H | H | H | H | 5,5,5-trifluoro-3-aminopentyl (attached via methyl) |
| 37 | S | H | H | NHAc | H | H | OMe | H | (S)-4-methylpentan-2-yl, 2-NH₂ |
| 38 | S | H | H | NHAc | H | H | CHF2 | H | (S)-4-methylpentan-2-yl, 2-NH₂ |
| 39 | S | H | H | Me | H | H | H | H | (S)-4-methylpentan-2-yl, 2-NH₂ |
| 40 | R | H | H | NHAc | H | H | H | H | (R)-4-methylpentan-2-yl, 2-NH₂ |
| 41 | S | H | H | NHAc | H | H | F | H | (S)-4-methylpentan-2-yl, 2-NH₂ |

TABLE 1a-continued (I)

| Ex | Stereo-chem | R¹ | R² | R⁴ | R⁵ | R⁶ | R⁷ | R⁸ | R³ |
|---|---|---|---|---|---|---|---|---|---|
| 42 | S | H | H | cyclopropyl-C(O)NH- | H | H | H | H | (S)-CH(CH₃)CH₂CH(CH₃)₂ with NH₂ |
| 43 | S | H | H | MeO-C(O)NH- | H | H | H | H | (S)-CH(CH₃)CH₂CH(CH₃)₂ with NH₂ |
| 44 | Racemate | H | H | NHAc | H | H | H | H | C(CH₃)(NH₂)CH₂CH(CH₃)₂ |

TABLE 1b

| Ex | (M + H)⁺ | AAK1 IC$_{50}$ (nM) | cell IC$_{50}$ (nM) |
|---|---|---|---|
| 1 | 299.2 | 20 | |
| 2 | 333.2 | d | |
| 3 | 271.1 | d | |
| 4 | 271.1 | c | |
| 5 | 299.2 | 3.3 | 8.4 |
| 6 | 313.2 | b | |
| 6a | 313.2 | 27 | 25 |
| 6b | 313.2 | 9.1 | 4.3 |
| 7a | 313.2 | 81 | >300 |
| 7b | 313.2 | c | |
| 8 | 339.2 | c | c |
| 8a | 339.2 | d | |
| 8b | 339.2 | c | c |
| 9 | 339.2 | d | |
| 9a | 339.2 | d | >300 |
| 9b | 339.2 | d | >300 |
| 10 | 327.2 | c | c |
| 10a | 327.2 | c | c |
| 10b | 327.2 | c | c |
| 11 | 313.2 | 22 | 38 |
| 12 | 356.2 | c | c |
| 13 | 314.2 | b | b |
| 14 | 377.0 | b | b |
| 15 | 328.2 | b | b |
| 16 | 317.0 | b | b |
| 17 | 339.1 | c | c |
| 18 | 356.2 | b | b |
| 19 | 341.2 | d | |
| 20 | 377.2 | c | |
| 21 | 391.0 | b | a |
| 22 | 338.2 | b | a |
| 23 | 324.2 | b | |
| 24 | 339.2 | c | c |
| 25 | 391.0 | b | |
| 26 | 331.2 | b | c |
| 27 | 401.2 | b | b |
| 27a | 401.2 | b | |
| 27b | 401.2 | b | b |
| 28 | 445.2 | b | b |
| 29 | 328.2 | c | |
| 30 | 370.2 | c | |
| 31a | 439.0 | b | |
| 31b | 439.0 | b | |
| 32 | 390.2 | 66 | >100 |
| 33 | 314.2 | c | c |
| 34 | 327.2 | c | |
| 35 | 370.2 | a | a |
| 36 | 396.2 | c | b |
| 37 | 386.2 | c | b |
| 38 | 406.2 | a | b |
| 39 | 312.5 | d | |
| 40 | 356.2 | b | |
| 41 | 372.2 | 0.3 | 2.1 |
| 42 | 382.3 | 0.5 | 2.1 |
| 43 | 372.2 | b | b |
| 44 | 370.4 | b | c |

In the following examples, proton NMR spectra were recorded on either a Bruker 400 or 500 MHz NMR spectrometer. Chemical shifts are reported in δ values relative to tetramethylsilane. Liquid chromatography (LC)/mass spectra were run on a Shimadzu LC coupled to a Waters Micromass ZQ. HPLC retention times were obtained using at least one of the following methods:

LC-MS methods:

Method A: Phenomenex C18 2×50 mm (3 μm), A=95% H₂O/5% MeCN, B=95% MeCN/5% H₂O, Modifier 10 mM NH₄OAc, 0.00 min=0% B, 4 min=100% B 5 min=100% B, Flow rate=0.8 mL/min Method B: Phenomenex C18 2×50 mm (3 μm), A=95% H₂O/5% ACN, B=95% MeCN/5% H₂O, Modifier 10 mM NH₄OAc, 0.00 min=30% B, 4 min=100% B 5 min=100% B, Flow rate=0.8 mL/min LC/MS Method C=Column: PUROSPHER@star RP-18 (4×55 mm), 3 μm; Buffer: 20 mMNH$_4$OAC IN WATER; Mphase A: Buffer+ACN(90+10); Mphase B: Buffer+MeCN (10+90); Flow: 2.5 ml/min)

LC/MS Method D=Column: ZORBAX SB C18 (46×50 mm), 5 μm; Positive mode Mphase A: 10% MeOH-90% H2O-0.1% TFA; Mphase B: 90% MeOH-10% H$_2$O-0.1% TFA; Flow: 5 ml/min)

LC/MS Method E=Column-Ascentis Express C8 (5×2.1 mm), 2.7 μm; Mphase A: 2% MeCN-98% H$_2$O-10 mM NH4COOH; Mphase B: 98% ACN-2% H$_2$O-10 mM NH$_4$COOH; Flow: 1 mL/min)

LC/MS Method F=Column-ACQUITY UPLC BEH C18 (2.1×50 mm), 1.7 μm; Mphase A:0.1% TFA in water; Mphase B: 1% TFA in ACN; Flow: 1 mL/min)

LC/MS Method G=Column-ACQUITY UPLC BEH C18 (2.1×50 mm), 1.7 μm; Mphase A:5 mM NH4OAc:ACN (95:5); Mphase B: 5 mM NH4OAc:ACN (5:95) Flow: 1 mL/min)

LC/MS Method H=Column: Xbridge BEH C18 (50×2.1 mm) 2.5 μm, Mobile phase A-1% HCOOH in H$_2$O; Mobile Phase B: ACN, Flow rate 1 mL/min): $t_R$=1.55 min LC/MS Method I=Column-ACE Excel 2 C18 (50×3.0) mm-2 μm; Mphase A: 2% MeCN-98% H$_2$O-10 mM NH4COOH; Mphase B: 98% ACN-2% H$_2$O-10 mM NH$_4$COOH; Flow: 1.2 mL/min):

LC/MS Method J=Column: Xbridge C18 (50×2.1 mm) 2.5 um, Mobile phase A-10 mM Ammonium hydrogen carbonate, Mobile Phase B: ACN, Flow rate 1 mL/min LC/MS Method K=Column: Kinetex C18 (50×2.1 mm-2.6 μm), Mobile phase A-2% ACN-98% H$_2$O-10 mM Ammonium formate, Mobile Phase B: 98% ACN-2% H$_2$O-10 mM Ammonium formate, Flow rate 1 mL/min Preparative HPLC Methods:

Method A: Waters Atlantis 30×100 mm, A=90% H$_2$O/10% MeOH, B=90% MeOH/10% H$_2$O, Modifier 0.1% TFA, 0.00 min=10% B, 12 min=100% B, 15.0 min=100% B, Flow rate=40 mL/min.

Method B: Waters Atlantis OBD 30×100 mm S5, A=90% H$_2$O/10% MeOH, B=90% MeOH/10% H$_2$O, Modifier 0.1% TFA, 0.00 min=10% B, 15 min=100% B, 18.0 min=100% B, Flow rate=40 mL/min.

Method C: Waters Atlantis 30×100 mm, A=90% H$_2$O/10% MeOH, B=90% MeOH/10% H$_2$O, Modifier 0.1% TFA, 0.00 min=10% B, 15 min=100% B, Flow rate=40 mL/min.

Chiral HPLC Methods:
Method A: CHIRALCEL OJH (250×4.6) mm 5 micron Mob. phase: 0.2% DEA in n-hexane:ethanol (80:20)
Method B: CHIRALPAK AD-H (250×4.6) mm 5 micron Mob. Phase A: 0.2% DEA in n-hexane (70) B: ethanol (30)
Method C: CHIRALPAK-ASH (250×4.6) mm 5 micron Mob. Phase A: 0.2% DEA in n-hexane:ethanol (90:10)

Analytical HPLC Methods:
Method A: Waters analytical C18 sunfire column (4.6×150 mm, 3.5 μm); mobile phase:
Buffer: 0.05% TFA in H$_2$O pH=2.5 adjusted with ammonia A=buffer and acetonitrile (95:5), B=acetonitrile and buffer (95:5); 0-15 min, 0% B→50% B; 15-18 min, 50% B→100% B; 18-23 min, 100% B; flow rate=1 mL/min; λ=254 nm and 220 nm; run time=28 min.

Method B: Waters analytical phenyl xbridge column (4.6× 150 mm, 3.5 μm), mobile phase:
Buffer: 0.05% TFA in H$_2$O pH=2.5 adjusted with ammonia A=buffer and acetonitrile (95:5), B=acetonitrile and buffer (95:5); 0-15 min, 0% B→50% B; 15-18 min, 50% B→100% B; 18-23 min, 100% B; flow rate=1 mL/min; λ=254 nm and 220 nm; run time=28 min.

Example 1

(R)-1-(5H-chromeno[3,4-e]pyridin-8-yloxy)-4-methylpentan-2-amine

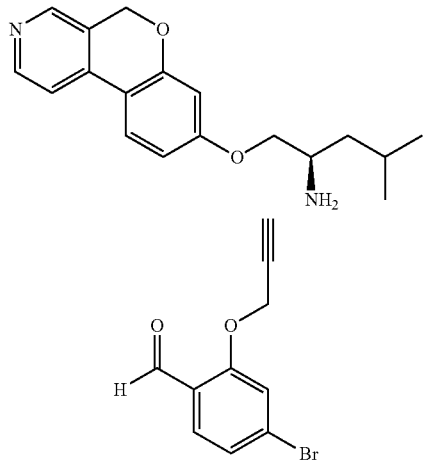

Part A. 4-bromo-2-(prop-2-ynyloxy)benzaldehyde

Conversion of 4-bromo-2-hydroxybenzaldehyde to its sodium salt was carried out as follows: A solution of 4-bromo-2-hydroxybenzaldehyde (3.0 g, 24.9 mmol) in MeOH (~150 mL) was treated with 1N aq. NaOH (15.7 mL, 1.05 equiv). The resulting pale yellow solution was concentrated under reduced pressure. EtOH (30 mL) was added to the residue and the solution was concentrated under reduced pressure. This was repeated with EtOH (30 mL) and then with heptane (50 mL). The resulting yellow, powdery sodium salt was dissolved in DMF (60 mL) with stirring and to it was added propargyl bromide in toluene (80 wt %, 2.33 mL, 1.4 equiv). The reaction mixture was stirred at ambient temperature for 22 h, after which time the volatiles were concentrated under reduced pressure. The residue was partitioned between EtOAc (70 mL) and water (40 mL). The organic layer was separated and treated with charcoal (~1 g) then dried (Na$_2$SO$_4$) and filtered. The filtrate was concentrated under reduced pressure. The residue obtained was crystallized from EtOAc and hexane (3:7). Crop I afforded 4-bromo-2-(prop-2-ynyloxy)benzaldehyde (893 mg) as colorless needles. The mother liquor was concentrated under reduced pressure and crystallized again from EtOAc and hexane (7:93) to obtain a further Crop II of 4-bromo-2-(prop-2-ynyloxy)benzaldehyde (1.902 g). The mother liquor was concentrated again and subjected to one more crystallization as described before. Crop III yielded additional 4-bromo-2-(prop-2-ynyloxy)benzaldehyde (344 mg). All the three crops were combined to give a total of 3.14 g (87% yield) of 4-bromo-2-(prop-2-ynyloxy)benzaldehyde as colorless needles. $^1$H NMR (500

MHz, CDCl$_3$) δ 10.43 (s, 1H), 7.74 (d, J=8.2 Hz, 1H), 7.31 (d, J=1.5 Hz, 1H), 7.24-7.28 (m, 1H), 4.85 (d, J=2.4 Hz, 2H), 2.64 (t, J=2.4 Hz, 1H); LCMS (Method A) (ESI) m/e 239.0, 241.0 Br pattern [(M+H)$^+$, calcd for C$_{10}$H$_7$BrO$_2$ 239.0]; SiO$_2$ TLC (EtOAc:Hexane=1:9) indicated R$_f$ of 0.32 compared with an R$_f$ of 0.43 for starting material aldehyde.

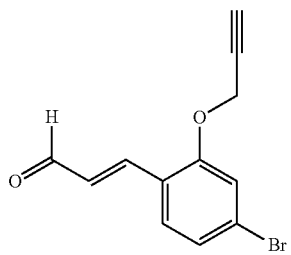

Part B. (E)-3-(4-bromo-2-(prop-2-ynyloxy)phenyl) acrylaldehyde

A mixture of 4-bromo-2-(prop-2-ynyloxy)benzaldehyde (0.852 g, 3.56 mmol) and formylmethylenetriphenylphosphorane (2.2 g, 7.12 mmol, 2 equiv) suspended in THF (20 mL) under nitrogen was stirred at ambient temperature for 18 h and then at 50° C. for another 24 h. The reaction mixture was filtered through a bed of silica gel (~25 g) eluting with EtOAc:hexane (1:4, 300 mL). The filtrate was concentrated under reduced pressure and the residue was purified by silica gel chromatography using a linear gradient of EtOAc:hexane (1:19 to 1:9). Pooled fractions containing the title compound and its Z-isomer in the ratio of (39:11, by NMR) was concentrated under reduced pressure to give (E)-3-(4-bromo-2-(prop-2-ynyloxy)phenyl)acrylaldehyde (0.69 g, 2.6 mmol, 57% yield). $^1$H NMR (500 MHz, CDCl$_3$) δ 9.71 (d, J=7.6 Hz, 1H), 7.77 (d, J=16.2 Hz, 1H), 7.45 (d, J=8.2 Hz, 1H), 7.26-7.17 (m, 2H), 6.77 (dd, J=16.2, 7.6 Hz, 1H), 4.82 (d, J=2.4 Hz, 1H), 4.80-4.75 (m, 1H), 2.62 (t, J=2.4 Hz, 1H). The Z-isomer showed the aldehydic proton at δ 9.87 (d, J=7.9 Hz) and a smaller cis-coupling (J=11.4 Hz) for the olefinic proton at δ 6.22; LCMS (Method B) (ESI) m/e 265.0, 267.0 Br pattern [(M+H)$^+$, calcd for C$_{12}$H$_9$BrO$_2$ 265.0].

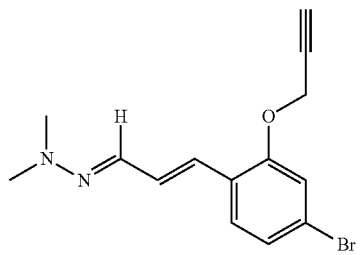 [SMILES: C#CCOc1cc(Br)ccc1/C=C/C=N/N(C)C]

Part C. (E)-2-((E)-3-(4-bromo-2-(prop-2-ynyloxy) phenyl)allylidene)-1,1-dimethylhydrazine A solution of (E)-3-(4-bromo-2-(prop-2-ynyloxy)phenyl) acrylaldehyde (2.85 g, 10.8 mmol) in dichloromethane (200 mL) containing anhydrous MgSO$_4$ (16 g) was cooled in an ice bath with stirring. To the ice-cold solution was added 1,1-dimethylhydrazine (2.45 mL, 32.4 mmol) dropwise and the reaction mixture was allowed to warm up to ambient temperature and was stirred for 18 h. The volatiles were concentrated under reduced pressure and the residue was coevaporated sequentially with dichloromethane (50 mL), dichloroethane (50 mL) and heptane (50 mL). (E)-2-((E)-3-(4-bromo-2-(prop-2-ynyloxy)phenyl)allylidene)-1,1-dimethylhydrazine (2.7 g, 8.79 mmol, 90% yield, 90% purity) was obtained as a yellow powder. $^1$H NMR (500 MHz, CDCl$_3$) δ 7.39 (d, J=7.9 Hz, 1H), 7.20-7.10 (m, 3H), 7.00-6.86 (m, 2H), 4.75 (d, J=2.3 Hz, 2H), 2.95 (s, 6H), 2.58 (t, J=2.3 Hz, 1H); LCMS (Method B) (ESI) m/e 307.0, 309.0 Br pattern [(M+H)$^+$, calcd for C$_{14}$H$_{15}$BrN$_2$O 307.0].

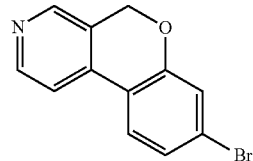 [SMILES: Brc1ccc2c(c1)OCc1cnccc1-2]

Part D. 8-bromo-5H-chromeno[3,4-c]pyridine

A solution of (E)-2-((E)-3-(4-bromo-2-(prop-2-ynyloxy) phenyl)allylidene)-1,1-dimethylhydrazine (116 mg, 374 mmol) and 2,6-di-tert-butyl-4-methylphenol (82 mg, 374 mmol) in mesitylene (4.5 mL) was degassed at 50° C. by bubbling argon for ~15 min while sonicating in a thick glass vial. The vial was capped under argon and heated to 140° C. in an oil bath with stirring for 138 h (5.75 days). The reaction mixture was cooled to ambient temperature and the solvent was concentrated under reduced pressure. The dark residue was purified by silica gel chromatography with EtOAc: dichloromethane (1:19) as the eluant. Fractions containing the required product were combined and concentrated under reduced pressure to give 8-bromo-5H-chromeno[3,4-c]pyridine (27 mg, 0.088 mmol, 25% yield based on 89% purity) as a pale yellow powder. $^1$H NMR (500 MHz, CDCl$_3$) δ 8.63 (d, J=5.2 Hz, 1H), 8.45 (s, 1H), 7.62 (d, J=8.2 Hz, 1H), 7.52 (d, J=5.2 Hz, 1H), 7.27-7.22 (m, 2H), 5.20 (s, 2H); LCMS (Method A) (ESI) m/e 262.0, 264.0 Br pattern [(M+H)$^+$, calcd for C$_{14}$H$_{15}$BrN$_2$O 262.0].

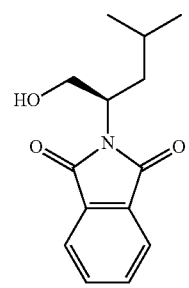 [SMILES: CC(C)C[C@H](CO)N1C(=O)c2ccccc2C1=O]

Part E. (R)-2-(1-hydroxy-4-methylpentan-2-yl)isoindoline-1,3-dione

The title compound was prepared in 75% yield on a 4 mmol scale as described in WO 2005/041684 A2. The product obtained had similar spectral characteristics as those reported.

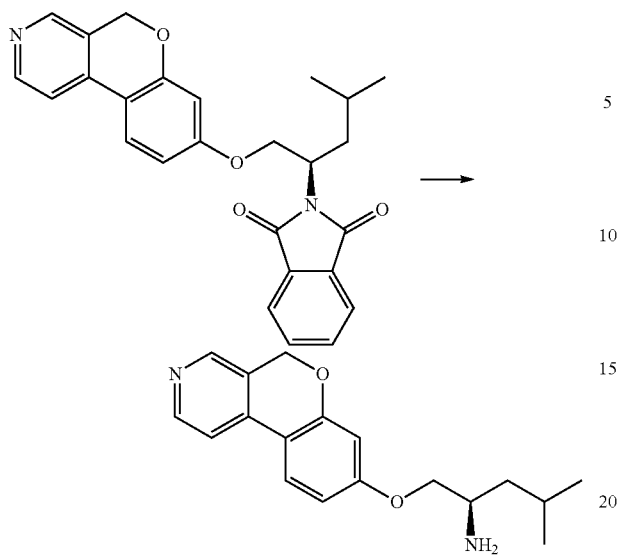

Part F. (R)-1-(5H-chromeno[3,4-d]pyridin-8-yloxy)-4-methylpentan-2-amine

Nitrogen was slowly bubbled for 5 min through a suspension of 8-bromo-5H-chromeno[3,4-c]pyridine (26 mg, 0.1 mmol), (R)-2-(1-hydroxy-4-methylpentan-2-yl)isoindoline-1,3-dione (116 mg, 0.47 mmol, 4.7 equiv), 5-(di-tert-butylphosphino)-1',3',5'-triphenyl-17'-1,4'-bipyrazole (30 mg, 0.06 mmol, 0.6 equiv), $Cs_2CO_3$ (49 mg, 0.15 mmol, 1.5 equiv) and $Pd(OAc)_2$ (7 mg, 0.03 mmol, 0.3 equiv) in toluene (0.5 mL) in a thick glass vial. The vial was capped and then heated at 80° C. for 19 h. The reaction mixture was cooled to ambient temperature and filtered through celite, washing with dichloromethane. The combined filtrate was concentrated under reduced pressure and the residue obtained was purified via silica gel chromatography with EtOAc:DCM (1:4) as the eluant. Fractions containing the desired product (with impurities) were concentrated under reduced pressure to give (R)-2-(1-(5H-chromeno[3,4-c]pyridin-8-yloxy)-4-methylpentan-2-yl)isoindoline-1,3-dione: $^1$H NMR (500 MHz, $CDCl_3$) δ 8.54 (d, J=5.2 Hz, 1H), 8.37 (s, 1H), 7.89-7.82 (m, 2H), 7.77-7.70 (m, 2H), 7.59 (d, J=8.9 Hz, 1H), 7.41 (d, J=5.5 Hz, 1H), 6.60 (dd, J=8.7, 2.6 Hz, 1H), 6.51 (d, J=2.4 Hz, 1H), 5.12 (s, 2H), 4.85-4.75 (m, 1H), 4.57 (t, J=9.5 Hz, 1H), 4.18 (dd, J=9.5, 4.9 Hz, 1H), 2.27-2.17 (m, 1H), 1.63-1.54 (m, 2H), 1.00 (d, J=5.8 Hz, 3H), 0.97 (d, J=6.1 Hz, 3H). By proton NMR the mixture was determined to be desired product, reagent and the phosphine oxide derived from the catalyst in an approximately 10:10:3 ratio respectively. Without further purification this mixture was taken to the next step of deprotection of phthalimido group as follows: A solution of (R)-2-(1-(5H-chromeno[3,4-c]pyridin-8-yloxy)-4-methylpentan-2-yl)isoindoline-1,3-dione (44 mg, 0.102 mmol) in ethanol (2 mL) was combined with hydrazine (0.022 mL, 714 mmol) and the solution was stirred at 45° C. for 3 h. The reaction mixture was cooled to room temperature and diluted with diethylether (10 mL) then filtered. The filtrate was concentrated under reduced pressure and the residue was purified by preparative HPLC (Method A). (R)-1-(5H-chromeno[3,4-c]pyridin-8-yloxy)-4-methylpentan-2-amine (23 mg, 0.077 mmol, 43% yield for two steps) was obtained as a pale yellow oil. $^1$H NMR (500 MHz, $CD_3OD$) δ 8.71-8.57 (m, 2H), 8.24 (d, J=6.4 Hz, 1H), 8.08 (m, 1H), 6.95 (dd, J=8.9, 2.4 Hz, 1H), 6.80 (d, J=2.4 Hz, 1H), 5.37 (s, 2H), 4.36 (m, 1H), 4.19 (dd, J=10.5, 6.4 Hz, 1H), 3.78-3.66 (m, 1H), 1.88-1.76 (m, 1H), 1.75-1.60 (m, 2H), 1.09-0.98 (m, 6H); LCMS (Method A) (ESI) m/e 299.2 [(M+H)$^+$, calcd for $C_{18}H_{22}N_2O_2$ 299.2]; optical rotation: $[α]^{20}_D$ (MeOH)=−5.9°.

Example 2

(R)-1-(5H-chromeno[3,4-d]pyridin-8-yloxy)-3-phenylpropan-2-amine

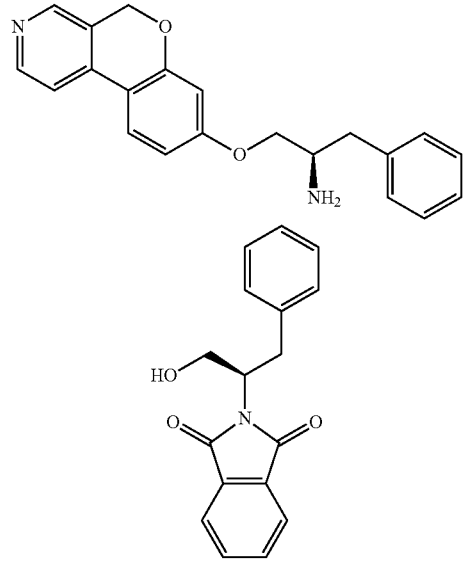

Part A. (R)-2-(1-hydroxy-3-phenylpropan-2-yl)isoindoline-1,3-dione

The title compound was prepared following the same protocol described for the synthesis of (R)-2-(1-hydroxy-4-methylpentan-2-yl)isoindoline-1,3-dione in Example 1, Part E. The compound thus prepared had the properties described in Sikoraiova, J. et. al. J. Heterocyclic. Chem. 2002, 39, 383.

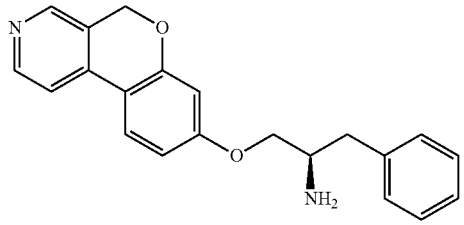 [SMILES: N[C@@H](COc1ccc2c(c1)OCc1cnccc1-2)Cc1ccccc1]

Part B. (R)-1-(5H-chromeno[3,4-d]pyridin-8-yloxy)-3-phenylpropan-2-amine

The title compound was prepared in 46% yield following the same protocol described in Example 1, Part F on a 30 mg (103 mmol) scale. After preparative HPLC (Method B) purification, (R)-1-(5H-chromeno[3,4-c]pyridin-8-yloxy)-3-phenylpropan-2-amine was obtained as a pale yellow oil. $^1$H NMR (500 MHz, $CD_3OD$) δ 8.72-8.59 (m, 2H), 8.24 (d, J=6.4 Hz, 1H), 8.07 (d, J=8.9 Hz, 1H), 7.43-7.36 (m, 2H), 7.36-7.29 (m, 3H), 6.93 (dd, J=8.9, 2.4 Hz, 1H), 6.74 (d, J=2.4 Hz, 1H), 5.36 (s, 2H), 4.27 (dd, J=10.7, 3.1 Hz, 1H), 4.11 (dd, J=10.7, 5.5 Hz, 1H), 3.96-3.88 (m, 1H), 3.15 (d, J=7.6 Hz, 2H); LCMS (Method A) (ESI) m/e 333.2 [(M+H)$^+$, calcd for $C_{21}H_{21}N_2O_2$ 333.2].

Example 3

(R)-1-(5H-chromeno[3,4-c]pyridin-8-yloxy)butan-2-amine

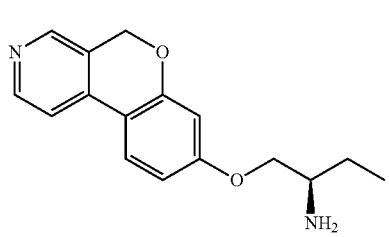

Part A. (R)-2-(1-hydroxybutan-2-yl)isoindoline-1,3-dione

The title compound was prepared following the same protocol described for the synthesis of (R)-2-(1-hydroxy-4-methylpentan-2-yl)isoindoline-1,3-dione in Example 1, Part E. The compound thus prepared had the properties described in Sikoraiova, J. et. al. *J. Heterocyclic. Chem.* 2002, 39, 383.

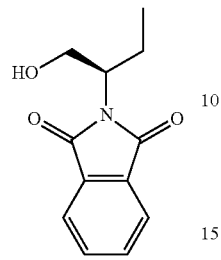

Part B. (R)-1-(5H-chromeno[3,4-c]pyridin-8-yloxy)butan-2-amine

The title compound was prepared in 21% yield following the same protocol described in Example 1, Part F on a 26 mg (100 mmol) scale. After preparative HPLC purification (Method B), (R)-1-(5H-chromeno[3,4-c]pyridin-8-yloxy)butan-2-amine was obtained as a pale yellow oil: $^1$H NMR (500 MHz, CD$_3$OD) δ 8.74-8.60 (m, 2H), 8.24 (d, J=6.4 Hz, 1H), 8.08 (d, J=8.9 Hz, 1H), 6.95 (dd, J=8.9, 2.4 Hz, 1H), 6.80 (d, J=2.4 Hz, 1H), 5.37 (s, 2H), 4.36 (dd, J=10.4, 3.4 Hz, 1H), 4.21 (dd, J=10.5, 6.6 Hz, 1H), 3.59 (m, 1H), 1.96-1.77 (m, 2H), 1.13 (t, J=7.6 Hz, 3H); LCMS (Method A) (ESI) m/e 271.1 [(M+H)$^+$, calcd for C$_{16}$H$_{19}$N$_2$O$_2$ 271.1].

Example 4

(S)-1-(5H-chromeno[3,4-c]pyridin-8-yloxy)butan-2-amine

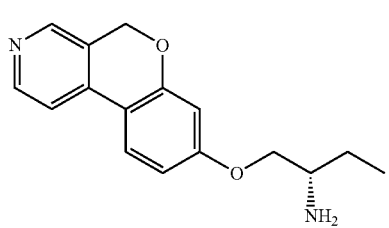 [SMILES: CC[C@H](N)COc1ccc2c(c1)OCc1cnccc1-2]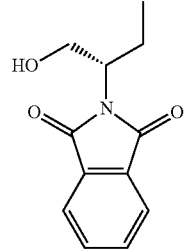

Part A. (S)-2-(1-hydroxybutan-2-yl)isoindoline-1,3-dione

The title compound was prepared following the same protocol described for the synthesis of (R)-2-(1-hydroxy-4-methylpentan-2-yl)isoindoline-1,3-dione in Example 1, Part E. The compound thus prepared had the properties described (Sikoraiova, J. et. al. *J. Heterocyclic. Chem.* 2002, 39, 383).

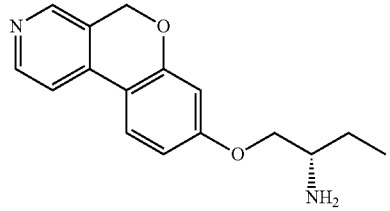

Part B. (S)-1-(5H-chromeno[3,4-c]pyridin-8-yloxy)butan-2-amine

The title compound was prepared in 19% yield following the same protocol described in Example 1, Part F on a 26 mg (100 mmol) scale. After preparative HPLC purification (Method C), (S)-1-(5H-chromeno[3,4-c]pyridin-8-yloxy)butan-2-amine was obtained as a pale yellow oil: $^1$H NMR (500 MHz, CD$_3$OD) δ 8.74-8.60 (m, 2H), 8.24 (d, J=6.4 Hz, 1H), 8.08 (d, J=8.9 Hz, 1H), 6.95 (dd, J=8.9, 2.4 Hz, 1H), 6.80 (d, J=2.4 Hz, 1H), 5.37 (s, 2H), 4.36 (dd, J=10.4, 3.4 Hz, 1H), 4.21 (dd, J=10.5, 6.6 Hz, 1H), 3.59 (m, 1H), 1.96-1.77 (m, 2H), 1.13 (t, J=7.6 Hz, 3H); LCMS (Method A) (ESI) m/e 271.1 [(M+H)$^+$, calcd for C$_{16}$H$_{19}$N$_2$O$_2$ 271.1].

Example 5

(S)-1-(5H-chromeno[3,4-c]pyridin-8-yloxy)-4-methylpentan-2-amine

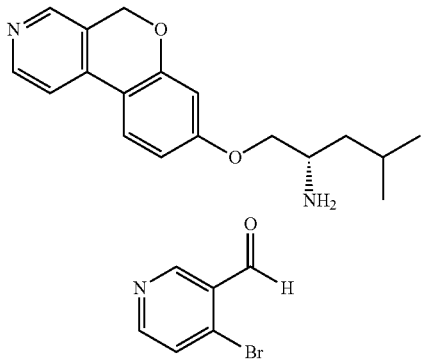

Part A. 4-bromonicotinaldehyde

To a stirred solution of diisopropylamine (9.02 mL, 63.3 mmol) in THF (75 mL) at −78° C. was added n-butyllithium (1.6 M in hexane) (30 mL, 76 mmol) dropwise under nitrogen atmosphere. After complete addition the solution was stirred for 30 min at −78° C. 4-Bromopyridine HCl (5 g, 31.6 mmol) was added portionwise and the resultant solution stirred at −78° C. for 1 h. DMF (2.94 mL, 38.0 mmol) was then added dropwise at −78° C. to the solution. The reaction mixture was warmed to room temperature slowly and stirred for 12 h. The reaction mixture was quenched with 3 N HCl and stirred for 2 h. The solution was neutralized with saturated sodium bicarbonate solution, extracted with EtOAc (75 mL), dried over sodium sulfate and concentrated under reduced pressure to give 4-bromonicotinaldehyde (3.75 g, 20.16 mmol, 64% yield). The crude product was used without purification in the next step. $^1$H NMR (400 MHz, CDCl$_3$) δ 10.39 (s, 1H), 9.00 (s, 1H), 8.56 (d, J=5.2 Hz, 1H), 7.62 (d, J=5.2 Hz, 1H).

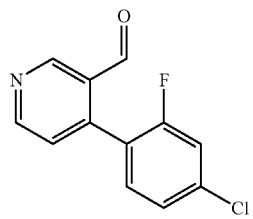 [SMILES: O=Cc1cnccc1-c1ccc(Cl)cc1F]

Part B. 4-(4-chloro-2-fluorophenyl)nicotinaldehyde

To a mixture of 4-bromonicotinaldehyde (3.00 g, 16.13 mmol), (4-chloro-2-fluorophenyl)boronic acid (2.81 g, 16.13 mmol), cesium carbonate (10.51 g, 32.3 mmol) and Pd(PPh$_3$)$_4$ (0.932 g, 0.806 mmol) was added THF (50 mL) and water (8 mL). Nitrogen gas was bubbled through the stirred suspension for 5 min. The reaction mixture was stirred under nitrogen atmosphere at 85° C. for 6 h. The reaction mixture was then cooled to room temperature and filtered through celite. The filtrate was diluted with ethyl acetate (30 mL) and washed with water (1×25 mL) and brine (1×25 mL). The combined organic extracts were dried over sodium sulfate and concentrated under reduced pressure. The crude residue was purified via silica gel chromatography (ethyl acetate/hexanes) to yield 4-(4-chloro-2-fluorophenyl)nicotinaldehyde (1.5 g, 6.37 mmol, 39% yield for two steps). $^1$H NMR (400 MHz, CDCl$_3$) δ 10.01 (s, 1H), 9.18 (s, 1H), 8.86 (d, J=5.1 Hz, 1H), 7.30 (m, 4H).

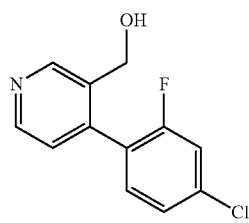 [SMILES: OCc1cnccc1-c1ccc(Cl)cc1F]

Part C. (4-(4-chloro-2-fluorophenyl)pyridin-3-yl)methanol

To a solution of 4-(4-chloro-2-fluorophenyl)nicotinaldehyde (3 g, 12.73 mmol) in a mixture of methanol (5 mL) and tetrahydrofuran (5 mL) cooled to 0° C. was added NaBH$_4$ (0.722 g, 19.10 mmol) and the solution stirred for 30 min. The reaction was quenched by addition of water (10 mL). The solution was extracted with ethyl acetate (3×15 mL). The combined organic extracts were washed with water (1×15 mL) and brine (1×15 mL), dried with sodium sulfate and concentrated under reduced pressure to yield (4-(4-chloro-2-fluorophenyl)pyridin-3-yl)methanol that was used without further purification in the next step. LCMS (ESI) m/e 238 [(M+H)$^+$, calcd for C$_{12}$H$_{10}$ClFNO 238.0].

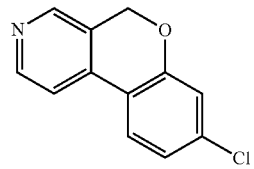 [SMILES: Clc1ccc2c(c1)OCc1cnccc1-2]

Part D. 8-Chloro-5H-chromeno[3,4-c]pyridine

To a cooled solution of (4-(4-chloro-2-fluorophenyl)pyridin-3-yl)methanol (2.89 g, 12.14 mmol) in THF (10 mL) at 0° C. was added a sodium hydride (1.94 g, 48.6 mmol) suspension in THF (10 mL) and the resultant mixture was stirred at 0° C. for 40 min. The reaction was quenched by addition of cold water (15 mL) and extracted with ethyl acetate (3×15 mL). The combined organic extracts were dried with sodium sulfate and concentrated under reduced pressure. The residue so obtained was purified by column chromatography (50% ethyl acetate in pet ether) to afford 8-chloro-5H-chromeno[3,4-c]pyridine (1.6 g, 7.35 mmol, 61% yield) as a white solid. $^1$H NMR (400 MHz, MeOD) δ 8.54 (d, J=5.60 Hz, 1H), 8.43 (s, 1H), 7.89 (d, J=8.40 Hz, 1H), 7.76 (d, J=5.60 Hz, 1H), 7.14 (dd, J=2.40, 8.40 Hz, 1H), 7.07 (d, J=2.00 Hz, 1H), 5.24 (s, 2H); LCMS (ESI) m/e 218 [(M+H)$^+$, calcd for C$_{12}$H$_9$ClNO 218.0].

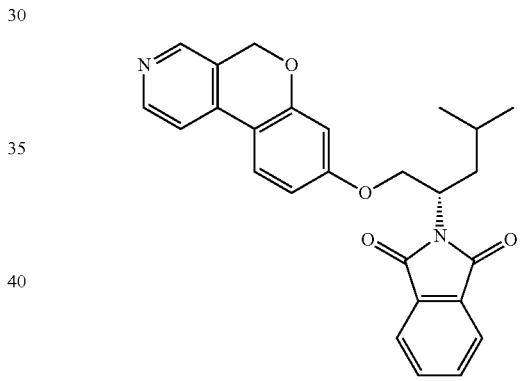

Part E. (S)-2-(1-((5H-chromeno[3,4-c]pyridin-8-yl)oxy)-4-methylpentan-2-yl)isoindoline-1,3-dione To a stirred suspension of 8-chloro-5H-chromeno[3,4-c]pyridine (1 g, 4.59 mmol), (S)-2-(1-hydroxy-4-methylpentan-2-yl)isoindoline-1,3-dione (3.43 g, 13.88 mmol), di-tert-butyl(2',4',6'-triisopropyl-[1,1'-biphenyl]-2-yl)phosphine (1.17 g, 2.76 mmol) and cesium carbonate (2.245 g, 6.89 mmol) in toluene (4 mL) was added palladium (II) acetate (0.309 g, 1.38 mmol). Nitrogen gas was bubbled through the mixture for 5 min, and then the mixture was heated at 80° C. for 14 h. The reaction was diluted with ethyl acetate (25 mL) and filtered through celite. The filtrate was washed with water (1×20 mL) and brine (1×20 mL), dried over sodium sulfate and concentrated under reduced pressure. The residue was purified via silica gel column chromatography (60% ethyl acetate in hexanes) to afford (S)-2-(1-((5H-chromeno[3,4-c]pyridin-8-yl)oxy)-4-methylpentan-2-yl)isoindoline-1,3-dione (2 g, 4.67 mmol, quantitative yield) as a semi solid. LCMS (ESI) m/e 429 [(M+H)$^+$, calcd for C$_{26}$H$_{25}$N$_2$O$_4$ 429.2].

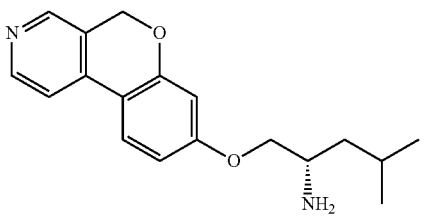 [SMILES: CC(C)C[C@H](N)COc1ccc2c(c1)OCc1cnccc1-2]

Part F. (S)-1-(5H-chromeno[3,4-c]pyridin-8-yloxy)-4-methylpentan-2-amine

To the solution of (S)-2-(1-((5H-chromeno[3,4-c]pyridin-8-yl)oxy)-4-methylpentan-2-yl)isoindoline-1,3-dione (1.47 g, 3.43 mmol) in ethanol (8 mL) under a nitrogen atmosphere was added hydrazine (0.754 mL, 24.02 mmol) at rt and the reaction mixture was then stirred at 45° C. in an oil bath for 3 h. A white precipitate formed during the course of the reaction. The reaction mixture was quenched by addition of water (15 mL) and the product was extracted with ethyl acetate (3×25 mL). The combined organic extracts were dried with sodium sulfate and concentrated under reduced pressure. The residue was purified by preparative HPLC on a reverse phase C-18 column using 10 mM ammonium acetate buffer and acetonitrile gradient. The fractions were concentrated under reduced pressure and lyophilized to yield (S)-1-((5H-chromeno[3,4-c]pyridin-8-yl)oxy)-4-methylpentan-2-amine (0.4 g, 0.970 mmol, 39% yield) as a yellow solid. $^1$H NMR (400 MHz, CD$_3$OD) δ 8.48 (d, J=5.6 Hz, 1H), 8.37 (s, 1H), 7.86 (d, J=8.8 Hz, 1H), 7.70 (d, J=5.2 Hz, 1H), 6.83 (dd, J=8.4, 2.4, 1H), 6.70 (d, J=2.4 Hz, 1H), 5.20 (s, 2H), 4.28 (dd, J=11.2, 3.6, 1H), 4.10 (dd, J=10.4, 6.4, 1H), 3.66 (m, 1H), 1.82 (m, 1H), 1.69-1.63 (m, 2H), 1.04 (m, 6H); LCMS (ESI) m/e 299.2 [(M+H)$^+$, calcd for C$_{18}$H$_{22}$N$_2$O$_2$ 299.38]; LC/MS retention time (Method E): t$_R$=1.78 min. HPLC retention time (method A): t$_R$=7.97 min; CHIRAL HPLC retention time (method C): t$_R$=12.87 min; optical rotation: [α]$^{20}$$_D$ (MeOH)=+7.1°.

Example 6

(2S)-4-methyl-1-(5-methyl-5H-chromeno[3,4-e]pyridin-8-yloxy)pentan-2-amine

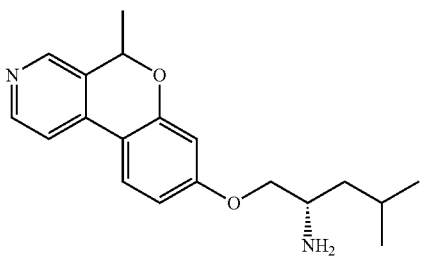

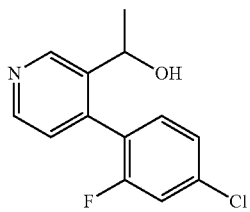

Part A. 1-(4-(4-chloro-2-fluorophenyl)pyridin-3-yl)ethanol

To a solution of 4-(4-chloro-2-fluorophenyl)nicotinaldehyde (0.12 g, 0.509 mmol) (prepared as in Example 5, Part B) in anhydrous THF (15 mL) was added methyl magnesium bromide (3.0 M in diethyl ether) (0.364 g, 3.06 mmol) at −60° C. dropwise. After complete addition the solution was stirred at −60° C. for 10 min. The reaction mixture was then allowed to warm to room temperature and stirred for 1 h. The reaction was quenched by addition of saturated aqueous ammonium chloride solution (15 mL). The organics were extracted with ethyl acetate (3×20 mL) and washed with water (1×15 mL) and brine (1×15 mL). The combined organic extracts were dried over sodium sulfate and concentrated under reduced pressure. The residue was purified via preparative TLC (20% ethyl acetate in hexane) to afford 1-(4-(4-chloro-2-fluorophenyl)pyridin-3-yl)ethanol (40 mg, 0.159 mmol, 31% yield) as an off-white solid: $^1$H NMR (400 MHz, CDCl$_3$) δ 8.89 (s, 1H), 8.50 (s, 1H), 7.15-7.26 (m, 3H), 7.07 (d, J=3.8 Hz, 1H), 4.82 (q, J=6.3 Hz, 1H), 3.06 (bs, 1H), 1.40 (d, J=6.3 Hz, 3H).

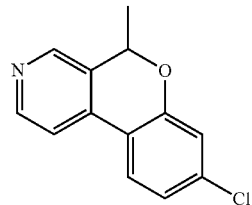 [SMILES: CC1Oc2cc(Cl)ccc2-c2ccncc21]

Part B.
8-Chloro-5-methyl-5H-chromeno[3,4-c]pyridine

To a stirred suspension of NaH (3.81 mg, 0.159 mmol) in anhydrous THF (5 mL), was added a THF (5 mL) solution of 1-(4-(4-chloro-2-fluorophenyl)pyridin-3-yl)ethanol (20 mg, 0.079 mmol) dropwise and the reaction mixture was stirred at room temperature for 4 h. The reaction was quenched by addition of saturated aqueous ammonium chloride solution (15 mL) and the product was extracted with ethyl acetate (3×20 mL). The combined organics were washed with water (1×15 mL) and brine (1×15 mL), dried over sodium sulfate and concentrated under reduced pressure. The residue was purified via preparative TLC (40% ethyl acetate in hexane) to afford 8-chloro-5-methyl-5H-chromeno[3,4-c]pyridine (12 mg, 0.052 mmol, 63% yield). $^1$H NMR (400 MHz, CDCl$_3$) δ 8.59 (d, J=5.2 Hz, 1H), 8.42 (s, 1H), 7.66 (d, J=8.3 Hz, 1H), 7.49 (d, J=5.2 Hz, 1H), 7.06 (m, 2H), 5.36 (q, J=6.6 Hz, 1H), 1.66 (d, J=6.6 Hz, 3H); LCMS (ESI) m/e 232 [(M+H)$^+$, calcd for C$_{13}$H$_{11}$ClNO 232.1].

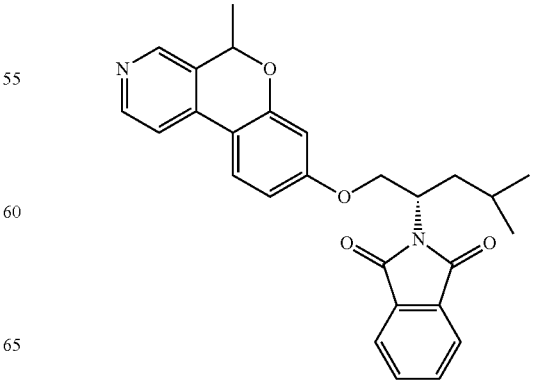

Part C. 2-((2S)-4-methyl-1-(5-methyl-5H-chromeno [3,4-c]pyridin-8-yloxy)pentan-2-yl)isoindoline-1,3-dione To a stirred solution of 8-bromo-5-methyl-5H-chromeno [3,4-c]pyridine (200 mg, 0.724 mmol) in toluene (4 mL), were added (S)-2-(1-hydroxy-4-methylpentan-2-yl)isoindoline-1,3-dione (537 mg, 2.173 mmol), di-tert-butyl(2',4',6'-triisopropyl-[1',1'-biphenyl]-2-yl)phosphine (185 mg, 0.435 mmol), cesium carbonate (354 mg, 1.086 mmol) and palladium (II) acetate (48.8 mg, 0.217 mmol). Nitrogen was bubbled through the reaction mixture for 10 min and the mixture was heated at 80° C. 12 h. The reaction mixture was cooled to room temperature and filtered through celite and residue rinsed with ethyl acetate. The filtrate was concentrated under reduced pressure and purified via prep TLC (60% ethyl acetate in pet ether) to afford 2-((2S)-4-methyl-1-(5-methyl-5H-chromeno[3,4-c]pyridin-8-yloxy)pentan-2-yl) isoindoline-1,3-dione (205 mg, 0.463 mmol, 64% yield). LCMS (ESI) m/e 443.2 [(M+H)$^+$, calcd for $C_{27}H_{27}N_2O_4$ 443.2]; LC/MS retention time (Method C): $t_R$=2.27 min.

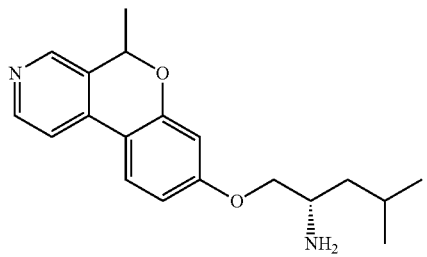 [SMILES: CC(C)C[C@H](N)COc1ccc2c(c1)OC(C)c1cnccc1-2]

Part D. (2S)-4-methyl-1-(5-methyl-5H-chromeno[3,4-c]pyridin-8-yloxy)pentan-2-amine To a solution of 1-((2S)-4-methyl-1-((5-methyl-5H-chromeno[3,4-c]pyridin-8-yl)oxy)pentan-2-yl)pyrrolidine-2,5-dione (205 mg, 0.520 mmol) in ethanol (20 mL) was added hydrazine monohydrate (260 mg, 5.20 mmol). The reaction mixture was heated at 45° C. for 5 h. The reaction mixture was cooled to room temperature, ether (50 mL) was added, and the mixture filtered. The filtrate was concentrated under reduced pressure. The residue was dissolved in dichloromethane (2 mL) and cooled to 0° C. 4 M HCl in dioxane (2 mL) was added the solution was stirred for 1 h. The reaction mixture was concentrated under reduced pressure and residue was dissolved in water (5 mL). The aqueous layer was washed with ethyl acetate (3×25 mL). To the aqueous layer was added acetonitrile (2 mL) and the solution was lyophilized to yield (2S)-4-methyl-1-(5-methyl-5H-chromeno[3,4-c]pyridin-8-yloxy)pentan-2-amine as an HCl salt. The crude product was purified via preparative HPLC (0.1% TFA in water and MeCN) to afford (2S)-4-methyl-1-(5-methyl-5H-chromeno [3,4-c]pyridin-8-yloxy)pentan-2-amine, 2TFA (145 mg, 0.268 mmol, 52% yield): $^1$H NMR (400 MHz, CD$_3$OD) δ 8.64 (d, J=6.1 Hz, 1H), 8.60 (s, 1H), 8.19 (d, J=6.1 Hz, 1H), 8.05 (d, J=8.9 Hz, 1H), 6.92 (m, 1H), 6.78 (d, J=2.5 Hz, 1H), 5.5 (m, 1H), 4.35 (m, 1H), 4.17 (m, 1H), 3.72 (m, 1H), 1.79 (m, 1H), 1.73 (d, J=6.6 Hz, 3H), 1.67 (m, 2H), 1.04 (m, 6H); LCMS (ESI) m/e 313.2 [(M+H)$^+$, calcd for $C_{19}H_{25}N_2O_2$ 313.2]; LC/MS retention time (Method E): $t_R$=1.69 min.

The diastereomeric mixture so obtained was resolved by preparative chiral HPLC (0.2% DEA in n-hexane, ethanol).

Diastereomer 1: Obtained diastereomer 1 (0.023 g, 0.072 mmol, 27% yield) as a pale yellow oil: $^1$H NMR (400 MHz, CD$_3$OD) δ 8.46 (d, J=5.36 Hz, 1H), 8.36 (s, 1H), 7.83 (d, J=8.7 Hz, 1H), 7.69 (d, J=5.2 Hz, 1H), 6.76 (m, 1H), 6.62 (d, J=2.48 Hz, 1H), 5.39 (m, 1H), 4.03 (m, 1H), 3.85 (m, 1H), 3.32 (m, 1H), 1.82 (m, 1H), 1.64 (m, 3H), 1.43 (m, 2H), 0.99 (m, 6H); HPLC retention time (method A): $t_R$=7.41 min; HPLC retention time (method B): $t_R$=8.97 min. CHIRAL HPLC retention time (method B): $t_R$=14.88 min.

Diastereomer 2: Obtained diastereomer 2 (0.022 g, 0.070 mmol, 26% yield) as a pale yellow oil: $^1$H NMR (400 MHz, CD$_3$OD) δ 8.46 (d, J=5.36 Hz, 1H), 8.36 (s, 1H), 7.83 (d, J=8.7 Hz, 1H), 7.69 (d, J=5.2 Hz, 1H), 6.76 (m, 1H), 6.62 (d, J=2.48 Hz, 1H), 5.39 (m, 1H), 4.03 (m, 1H), 3.85 (m, 1H), 3.33 (m, 1H), 1.82 (m, 1H), 1.64 (m, 3H), 1.43 (m, 2H), 0.99 (m, 6H); HPLC retention time (method A): $t_R$=7.45 min; HPLC retention time (method B): $t_R$=8.93 min. CHIRAL HPLC retention time (method B): $t_R$=19.41 min.

Example 7

(2R)-4-methyl-1-(5-methyl-5H-chromeno[3,4-d] pyridin-8-yloxy)pentan-2-amine

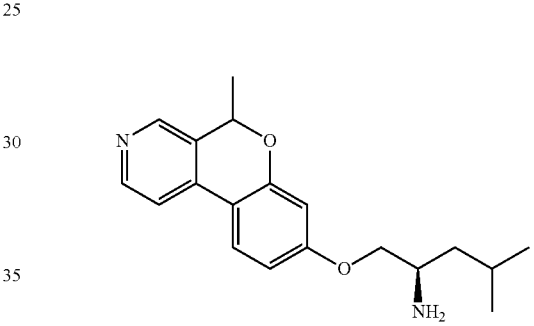

(2R)-4-methyl-1-(5-methyl-5H-chromeno[3,4-c]pyridin-8-yloxy)pentan-2-amine was prepared in analogous fashion to Example 6. The diastereomeric mixture so obtained was resolved by preparative chiral HPLC (0.2% DEA in n-hexane, ethanol).

Diastereomer 1: Obtained diastereomer 1 (19 mg, 0.061 mmol, 26% yield) as a yellow solid: $^1$H NMR (400 MHz, CD$_3$OD) δ 8.67 (d, J=6.40 Hz, 1H), 8.65 (s, 1H), 8.26 (d, J=6.40 Hz, 1H), 8.09 (d, J=8.80 Hz, 1H), 6.95 (q, J=2.40 Hz, 1H), 6.80 (d, J=2.40 Hz, 1H), 5.58 (q, J=6.40 Hz, 1H), 4.36 (q, J=3.20 Hz, 1H), 4.18 (q, J=6.40 Hz, 1H), 3.73 (q, J=2.80 Hz, 1H), 1.74-1.85 (m, 1H), 1.72 (d, J=2.80 Hz, 3H), 1.61-1.70 (m, 2H), 1.05 (q, J=3.60 Hz, 6H); LCMS (ESI) m/e 313.2 [(M+H)$^+$, calcd for $C_{19}H_{25}N_2O_2$ 313.2]; LC/MS retention time (Method E): $t_R$=1.73 min; HPLC retention time (method A): $t_R$=8.06 min; HPLC retention time (method B): $t_R$=9.11 min; Chiral HPLC retention time (method B): $t_R$=15.34 min.

Diastereomer 2: Obtained diastereomer 2 (31 mg, 0.099 mmol, 43% yield) as a yellow solid:

$^1$H NMR (400 MHz, CD$_3$OD) δ 8.68 (d, J=6.40 Hz, 1H), 8.65 (s, 1H), 8.27 (d, J=6.40 Hz, 1H), 8.09 (d, J=8.80 Hz, 1H), 6.95 (dd, J=2.40, 8.80 Hz, 1H), 6.80 (d, J=2.80 Hz, 1H), 5.58 (q, J=6.80 Hz, 1H), 4.36 (dd, J=3.60, 10.60 Hz, 1H), 4.19 (q, J=6.40 Hz, 1H), 3.70-3.76 (m, 1H), 1.74-1.85 (m, 1H), 1.72 (d, J=3.20 Hz, 3H), 1.61-1.70 (m, 2H), 1.05 (q, J=4.00 Hz, 6H); LCMS (ESI) m/e 313.2 [(M+H)$^+$, calcd for $C_{19}H_{25}N_2O_2$ 313.2]; LC/MS retention time (Method E): $t_R$=1.72 min; HPLC retention time (method B): $t_R$=13.14 min, Chiral HPLC retention time (method B): $t_R$=12.06 min.

Example 8

(2S)-1-(5-cyclopropyl-5H-chromeno[3,4-c]pyridin-8-yloxy)-4-methylpentan-2-amine

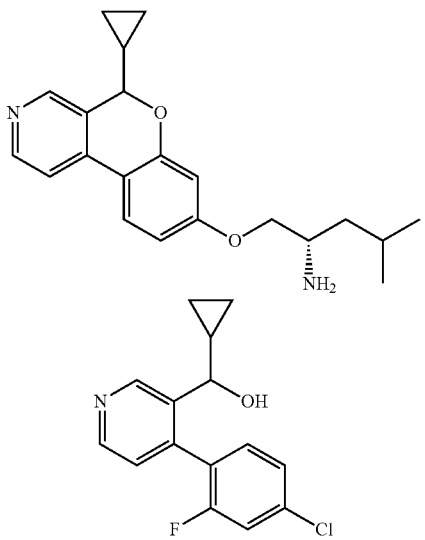

Part A. (4-(4-chloro-2-fluorophenyl)pyridin-3-yl)(cyclopropyl)methanol

To a solution of 4-(4-chloro-2-fluorophenyl)nicotinaldehyde (1.6 g, 6.79 mmol) (prepared as in Example 5, Part B) in THF (32 mL) cooled to −78° C., was added cyclopropylmagnesium bromide (27.2 mL, 13.58 mmol) dropwise over a period of 20 min. The reaction mixture was allowed to stir at −78° C. for 3 h. The dry ice bath was removed and reaction mixture was brought to room temperature. The reaction mixture was quenched by addition of saturated aqueous ammonium chloride solution (30 mL). The reaction mixture was extracted with ethyl acetate (3×50 mL). The combined organic extracts were washed with brine (1×50 mL), dried over sodium sulfate and concentrated under reduced pressure. The crude product was purified by silica gel chromatography (30% ethyl acetate in pet ether) to afford (4-(4-chloro-2-fluorophenyl)pyridin-3-yl)(cyclopropyl)methanol (900 mg, 3.24 mmol, 48% yield). LCMS (ESI) m/e 278.0 [(M+H)$^+$, calcd for $C_{15}H_{14}ClFNO$ 278.1]; LC/MS retention time (Method C): $t_R$=1.62 min.

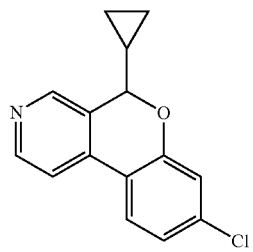 [SMILES: Clc1ccc2c(c1)OC(C1CC1)c1cnccc1-2]

Part B. 8-Chloro-5-cyclopropyl-5H-chromeno[3,4-c]pyridine

To a suspension of NaH (389 mg, 9.72 mmol) in THF (9 mL) cooled to 0° C., was added (4-(4-chloro-2-fluorophenyl)pyridin-3-yl)(cyclopropyl)methanol (900 mg, 3.24 mmol) in THF (9 mL) dropwise over a period of 10 min. The reaction mixture was stirred at 0° C. for 15 min and then warmed to room temperature and stirred for 15 h. The reaction mixture was quenched by addition of cold water (10 mL) and extracted with ethyl acetate (3×25 mL). The combined organic extracts were washed with brine (1×25 mL), dried over sodium sulfate and concentrated under reduced pressure. The crude residue was purified via silica gel column chromatography (ethyl acetate/hexanes) to give 8-chloro-5-cyclopropyl-5H-chromeno[3,4-c]pyridine (630 mg, 2.45 mmol, 75% yield). LCMS (ESI) m/e 258.0 [(M+H)$^+$, calcd for $C_{15}H_{13}ClNO$ 258.1]; LC/MS retention time (Method C): $t_R$=2.08 min.

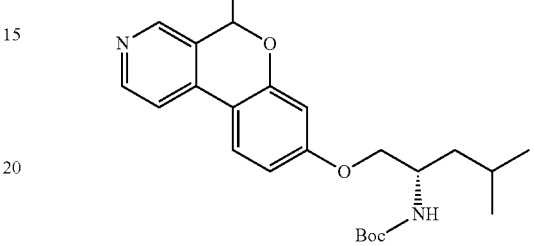

Part C. tert-Butyl-(2S)-1-(5-cyclopropyl-5H-chromeno[3,4-e]pyridin-8-yloxy)-4-methylpentan-2-ylcarbamate To a stirred solution of 8-chloro-5-cyclopropyl-5H-chromeno[3,4-c]pyridine (275 mg, 1.067 mmol) in toluene (3 mL) was added (S)-tert-butyl (1-hydroxy-4-methylpentan-2-yl)carbamate (696 mg, 3.20 mmol), cesium carbonate (427 mg, 1.310 mmol), di-tert-butyl(2',4',6'-triisopropyl-[1',1'-biphenyl]-2-yl)phosphine (272 mg, 0.640 mmol) and palladium (II) acetate (71.9 mg, 0.320 mmol). Nitrogen was bubbled through the reaction mixture for 10 min then the mixture was heated at 80° C. for 12 h. The reaction mixture was cooled to room temperature and filtered through celite. The filtrate was diluted with water (10 mL) and extracted with ethyl acetate (3×15 mL). The combined organic extracts were washed with brine (1×15 mL), dried over sodium sulfate and concentrated under reduced pressure. The crude product was purified via silica gel chromatography (ethyl acetate/pet ether) to give tert-butyl-(2S)-1-(5-cyclopropyl-5H-chromeno[3,4-c]pyridin-8-yloxy)-4-methylpentan-2-ylcarbamate (250 mg, 0.57 mmol, 50% yield). LCMS (ESI) m/e 439.2 [(M+H)$^+$, calcd for $C_{26}H_{35}N_2O_4$ 439.3]; LC/MS retention time (Method C): $t_R$=2.16 min.

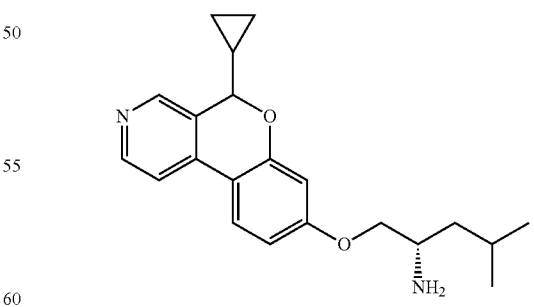

Part D. (2S)-1-(5-cyclopropyl-5H-chromeno[3,4-e]pyridin-8-yloxy)-4-methylpentan-2-amine To a solution of tert-butyl((2S)-1-((5-cyclopropyl-5H-chromeno[3,4-c]pyridin-8-yl)oxy)-4-methylpentan-2-yl)

carbamate (250 mg, 0.570 mmol) in CH$_2$Cl$_2$ (4 mL) cooled to 0° C. was added 1N HCl in dioxane (2 mL, 0.570 mmol) slowly over a period of 5 min. The reaction mixture was stirred at 0° C. for 5 min then was warmed to room temperature and allowed to stir for 2 h. The solvents were removed by concentration under reduced pressure. The crude product was washed with ethyl acetate to yield (2S)-1-(5-cyclopropyl-5H-chromeno[3,4-c]pyridin-8-yloxy)-4-methylpentan-2-amine as an HCl salt (240 mg, 42% yield). LCMS (ESI) m/e 339.2 [(M+H)$^+$, calcd for C$_{21}$H$_{27}$N$_2$O$_2$ 339.2]; LC/MS retention time (Method C): $t_R$=1.28 min. The diastereomeric mixture of amines was resolved by chiral preparative HPLC (0.2% DEA in n-hexane, ethanol).

Diastereomer 1: Obtained diastereomer 1 (45 mg, 0.133 mmol, 23% yield) as a yellow oil. $^1$H NMR (400 MHz, CD$_3$OD) δ 8.48 (s, 1H), 8.47 (d, J=5.5 Hz, 1H), 7.83 (d, J=8.7 Hz, 1H), 7.70 (d, J=5.3 Hz, 1H), 6.75 (m, 1H), 6.65 (d, J=2.4 Hz, 1H), 4.52 (d, J=8.9 Hz, 1H), 4.04 (m, 1H), 3.87 (m, 1H), 3.29 (m, 1H), 1.82 (m, 1H), 1.39 (m, 3H), 0.99 (m, 6H), 0.70 (m, 2H), 0.61 (m, 1H), 0.52 (m, 1H); LCMS (ESI) m/e 339.2 [(M+H)$^+$, calcd for C$_{21}$H$_{27}$N$_2$O$_2$ 339.2]; LC/MS retention time (Method C): $t_R$=1.46 min; HPLC retention time (method A): $t_R$=8.92 min; HPLC retention time (method B): $t_R$=10.33 min; Chiral HPLC retention time (method C): $t_R$=10.3 min.

Diastereomer 2: Obtained diastereomer 2 (35 mg, 0.103 mmol, 18% yield) as a yellow oil. $^1$H NMR (400 MHz, CD$_3$OD) δ 8.48 (s, 1H), 8.47 (d, J=5.4 Hz, 1H), 7.83 (d, J=8.7 Hz, 1H), 7.70 (d, J=5.3 Hz, 1H), 6.75 (m, 1H), 6.65 (d, J=2.4 Hz, 1H), 4.52 (d, J=8.9 Hz, 1H), 4.04 (m, 1H), 3.85 (m, 1H), 3.33 (m, 1H), 1.83 (m, 1H), 1.39 (m, 3H), 0.99 (m, 6H), 0.70 (m, 2H), 0.53-0.61 (m, 2H); LCMS (ESI) m/e 339.2 [(M+H)$^+$, calcd for C$_{21}$H$_{27}$N$_2$O$_2$ 339.2]; LC/MS retention time (Method C): $t_R$=1.46 min; HPLC retention time (method A): $t_R$=8.89 min; HPLC retention time (method B): $t_R$=10.34 min; Chiral HPLC retention time (method C): $t_R$=14.11 min.

Example 9

(2R)-4-methyl-1-(5-methyl-5H-chromeno[3,4-d]pyridin-8-yloxy)pentan-2-amine

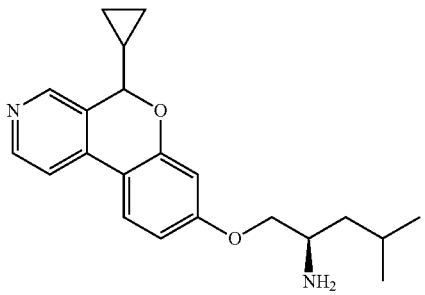 [SMILES: CC(C)C[C@@H](N)COc1ccc2c(c1)OC(C1CC1)c1cnccc1-2]

(2R)-4-methyl-1-(5-methyl-5H-chromeno[3,4-c]pyridin-8-yloxy)pentan-2-amine was prepared in analogous fashion to Example 8. The diastereomeric mixture was resolved using chiral prep HPLC (0.2% DEA in n-hexane and ethanol).

Diastereomer 1: Obtained diastereomer 1 (0.03 g, 0.089 mmol, 19% yield) as a yellow oil: $^1$H NMR (400 MHz, CD$_3$OD) δ 8.48 (d, J=1.60 Hz, 1H), 8.47 (s, 1H), 7.83 (d, J=8.80 Hz, 1H), 7.70 (d, J=5.20 Hz, 1H), 6.76 (dd, J=2.80, 8.60 Hz, 1H), 6.66 (d, J=2.40 Hz, 1H), 4.52 (d, J=9.20 Hz, 1H), 4.05 (dd, J=3.60, 9.40 Hz, 1H), 3.87 (q, J=7.20 Hz, 1H), 3.32-3.33 (m, 1H), 1.81-1.84 (m, 1H), 1.32-1.52 (m, 3H), 0.98-1.02 (m, 6H), 0.71 (dd, J=2.80, 4.60 Hz, 2H), 0.50-0.54 (m, 2H); LCMS (ESI) m/e 339.2 [(M+H)$^+$, calcd for C$_{21}$H$_{27}$N$_2$O$_2$ 339.2]; LC/MS retention time (Method C): $t_R$=1.33 min; HPLC retention time (method A): $t_R$=4.51 min; HPLC retention time (method B): $t_R$=5.18 min; Chiral HPLC retention time (method C): $t_R$=11.01 min.

Diastereomer 2: Obtained diastereomer 2 (0.028 g, 0.083 mmol, 18% yield) as a yellow oil: $^1$H NMR (400 MHz, CD$_3$OD) δ 8.48 (d, J=1.60 Hz, 1H), 8.47 (s, 1H), 7.83 (d, J=8.80 Hz, 1H), 7.70 (d, J=5.60 Hz, 1H), 6.75 (dd, J=2.40, 8.80 Hz, 1H), 6.65 (d, J=2.40 Hz, 1H), 4.52 (d, J=9.20 Hz, 1H), 4.03 (dd, J=3.60, 9.40 Hz, 1H), 3.86 (dd, J=7.20, 9.40 Hz, 1H), 3.20-3.28 (m, 1H), 1.79-1.86 (m, 1H), 1.38-1.46 (m, 3H), 1.00 (q, J=6.40 Hz, 6H), 0.72 (d, J=2.80 Hz, 2H), 0.51-0.65 (m, 2H), LCMS (ESI) m/e 339.2 [(M+H)$^+$, calcd for C$_{21}$H$_{27}$N$_2$O$_2$ 339.2]; LC/MS retention time (Method C): $t_R$=1.34 min; HPLC retention time (method A): $t_R$=4.55 min; HPLC retention time (method B): $t_R$=5.18 min; Chiral HPLC retention time (method C): $t_R$=14.57 min.

Example 10

(2S)-1-(5-ethyl-5H-chromeno[3,4-c]pyridin-8-yloxy)-4-methylpentan-2-amine

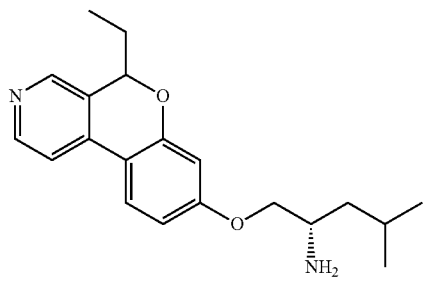

Part A. 1-(4-(4-chloro-2-fluorophenyl)pyridin-3-yl)prop-2-en-1-ol

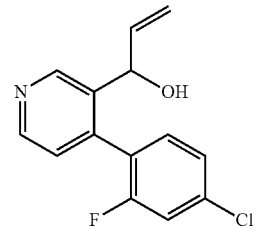

To a stirred solution of 4-(4-chloro-2-fluorophenyl)nicotinaldehyde (0.5 g, 2.122 mmol) (prepared as in Example 5, Part B) in THF (25 mL) at −70° C. was added vinylmagnesium bromide (1.0 M in THF) (6.37 mL, 6.64 mmol) dropwise and the solution was stirred at this temperature for 45 min. The reaction was quenched with saturated aqueous ammonium chloride solution (20 mL) and extracted with ethyl acetate (2×15 mL). The combined organic extracts were washed with brine (1×15 mL), dried over sodium sulfate and concentrated under reduced pressure. The crude product was used without purification in the next step. LCMS (ESI) m/e 264 [(M+H)$^+$, calcd for C$_{14}$H$_{12}$ClFNO 264.0]; LC/MS retention time (Method C): $t_R$=1.59 min.

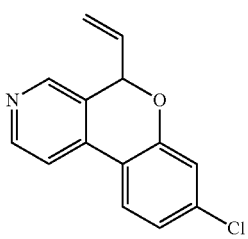 [SMILES: C=CC1Oc2cc(Cl)ccc2-c2ccncc21]

Part B.
8-chloro-5-vinyl-5H-chromeno[3,4-c]pyridine

To a stirred suspension of NaH (0.182 g, 7.58 mmol) in THF (30 mL) was added 1-(4-(4-chloro-2-fluorophenyl)pyridin-3-yl)prop-2-en-1-ol (0.5 g, 1.896 mmol) dissolved in THF (5 mL) and the reaction mixture was stirred at room temperature for 2 h. The reaction was quenched by addition of saturated aqueous ammonium chloride solution (5 mL) and extracted with ethyl acetate (3×10 mL). The combined organic extracts were washed with brine (1×10 mL), dried over sodium sulfate and concentrated under reduced pressure. The crude 8-chloro-5-vinyl-5H-chromeno[3,4-c]pyridine was used without purification in the next step.

$^1$H NMR (400 MHz, CDCl$_3$) δ 8.61 (d, J=5.2 Hz, 1H), 8.40 (s, 1H), 7.65 (d, J=8.8 Hz, 1H), 7.5 (d, J=5.2 Hz, 1H), 7.06 (d, J=2.2 Hz, 2H), 6.09 (m, 1H), 5.70 (d, J=6.2 Hz, 1H), 5.37 (m, 1H), 5.28 (m, 1H).

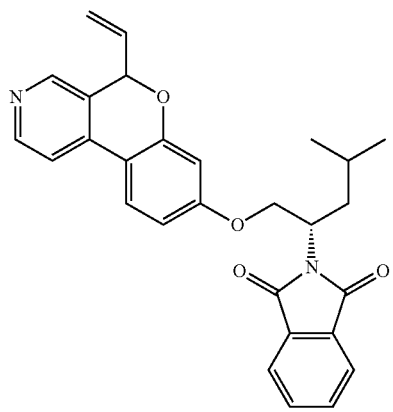 [SMILES: C=CC1Oc2cc(OC[C@H](CC(C)C)N3C(=O)c4ccccc4C3=O)ccc2-c2ccncc21]

Part C. 2-((2S)-4-methyl-1-(5-vinyl-5H-chromeno[3,4-e]pyridin-8-yloxy)pentan-2-yl)isoindoline-1,3-dione To a stirred suspension of 8-chloro-5-vinyl-5H-chromeno[3,4-c]pyridine (0.2 g, 0.821 mmol), (S)-2-(1-hydroxy-4-methylpentan-2-yl)isoindoline-1,3-dione (0.609 g, 2.462 mmol), 2-di-tert-butylphosphino-2,4,6-triisopropylbiphenyl (0.209 g, 0.492 mmol), and cesium carbonate (0.401 g, 1.231 mmol) in toluene (25 mL) was added palladium (II) acetate (0.055 g, 0.246 mmol). Nitrogen gas was bubbled through the mixture for 5 min, and then the reaction mixture was heated to 80° C. for 14 h. The reaction was diluted with ethyl acetate (25 mL) and filtered through celite. The filtrate was washed with water (1×20 mL) and brine (1×20 mL), dried over sodium sulfate and concentrated under reduced pressure. The residue was purified via silica gel column chromatography (60% ethyl acetate in hexanes) to afford 24(2S)-4-methyl-1-(5-vinyl-5H-chromeno[3,4-c]pyridin-8-yloxy)pentan-2-yl)isoindoline-1,3-dione (0.3 g, 0.660 mmol, 40% yield for three steps). LCMS (ESI) m/e 455.2 [(M+H)$^+$, calcd for C$_{28}$H$_{27}$N$_2$O$_4$ 455.2]; LC/MS retention time (Method C): t$_R$=2.16 min.

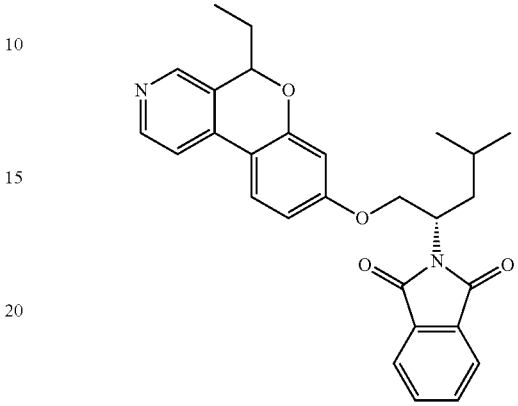

Part D. 2-((2S)-1-(5-ethyl-5H-chromeno[3,4-e]pyridin-8-yloxy)-4-methylpentan-2-yl)isoindoline-1,3-dione To a stirred solution of 2-((2S)-4-methyl-1-((5-vinyl-5H-chromeno[3,4-c]pyridin-8-yl)oxy)pentan-2-yl)isoindoline-1,3-dione (0.3 g, 0.660 mmol) in methanol (15 mL) was added 10% palladium on carbon (0.070 g, 0.660 mmol). The resultant mixture was stirred at room temperature under a hydrogen atmosphere (1 atm) for 12 h. The reaction mixture was then filtered through celite and concentrated under reduced pressure to yield crude 2-((2S)-1-(5-ethyl-5H-chromeno[3,4-c]pyridin-8-yloxy)-4-methylpentan-2-yl)isoindoline-1,3-dione (0.28 g, 0.221 mmol, 33% crude yield); LCMS (ESI) m/e 457.2 [(M+H)$^+$, calcd for C$_{28}$H$_{29}$N$_2$O$_4$ 457.2]; LC/MS retention time (Method C): t$_R$=2.32 min.

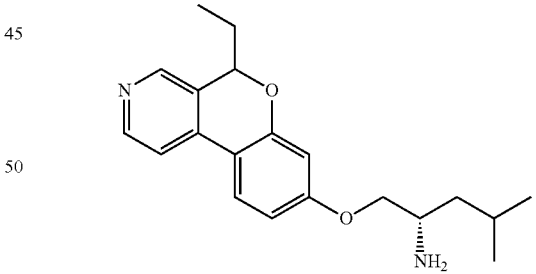

Part E. (2S)-1-(5-ethyl-5H-chromeno[3,4-e]pyridin-8-yloxy)-4-methylpentan-2-amine To a stirred solution of 2-(2S)-1-(5-ethyl-5H-chromeno[3,4-c]pyridin-8-yloxy)-4-methylpentan-2-yl)isoindoline-1,3-dione (0.25 g, 0.548 mmol) in ethanol (15 mL) was added hydrazine (0.172 mL, 5.48 mmol) and the reaction mixture was stirred at 40° C. for 6 h. The reaction was cooled to room temperature then diluted with DCM (20 mL) and filtered through a bed of celite. The filtrate was concentrated under reduced pressure and purified by preparative HPLC (0.1%

TFA in water and methanol) to yield (2S)-1-((5-ethyl-5H-chromeno[3,4-d]pyridin-8-yl)oxy)-4-methylpentan-2-amine (40 mg, 21% yield). The diastereomeric mixture was resolved by SFC (0.5% DEA in methanol).

Diastereomer 1: Diastereomer 1 (2S)-1-((5-ethyl-5H-chromeno[3,4-c]pyridin-8-yl)oxy)-4-methylpentan-2-amine (12 mg, 0.037 mmol, 7% yield) was obtained as an off-white sticky solid. $^1$H NMR (400 MHz, CD$_3$OD) δ 8.45 (d, J=5.4 Hz, 1H), 8.32 (s, 1H), 7.81 (d, J=8.7 Hz, 1H), 7.69 (d, J=5.3 Hz, 1H), 6.74 (m, 1H), 6.62 (d, J=2.4 Hz, 1H), 5.21 (m, 1H), 4.02 (m, 1H), 3.83 (m, 1H), 3.25 (m, 1H), 1.94 (m, 1H), 1.79 (m, 2H), 1.42 (m, 2H), 1.06 (m, 3H), 0.99 (m, 6H); LCMS (ESI) m/e 327.2 [(M+H)$^+$, calcd for C$_{20}$H$_{27}$N$_2$O$_2$ 327.2]; LC/MS retention time (Method C): t$_R$=1.48 min; HPLC retention time (method B): t$_R$=14.09 min.

Diastereomer 2: Diastereomer 2 (2S)-1-((5-ethyl-5H-chromeno[3,4-c]pyridin-8-yl)oxy)-4-methylpentan-2-amine (13 mg, 0.04 mmol, 7% yield) was obtained as an off-white sticky solid. $^1$H NMR (400 MHz, CD$_3$OD) δ 8.45 (d, J=5.4 Hz, 1H), 8.32 (s, 1H), 7.81 (d, J=8.7 Hz, 1H), 7.69 (d, J=5.3 Hz, 1H), 6.74 (m, 1H), 6.62 (d, J=2.4 Hz, 1H), 5.21 (m, 1H), 4.02 (m, 1H), 3.83 (m, 1H), 3.25 (m, 1H), 1.94 (m, 1H), 1.79 (m, 2H), 1.42 (m, 2H), 1.06 (m, 3H), 0.99 (m, 6H); LCMS (ESI) m/e 327.2 [(M+H)$^+$, calcd for C$_{20}$H$_{27}$N$_2$O$_2$ 327.2]; LC/MS retention time (Method C): t$_R$=1.48 min; HPLC retention time (method B): t$_R$=13.85 min.

Example 11

(S)-8-(2-amino-4-methylpentyloxy)-5H-chromeno[3,4-c]pyridin-5-one

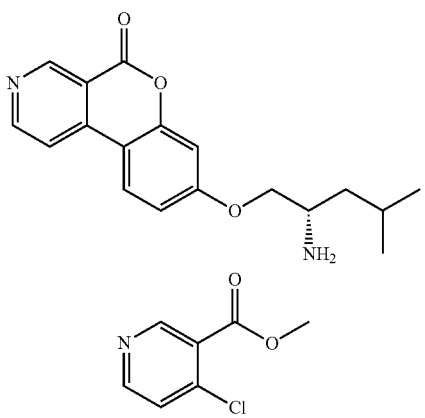

Part A. methyl 4-chloronicotinate

To a solution of 4-chloronicotinic acid (0.5 g, 3.17 mmol) in CH$_2$Cl$_2$ (60 mL) was added oxalyl chloride (1.007 g, 7.93 mmol) dropwise at room temperature followed by the addition of DMF (0.4 mL). The solution was stirred at room temperature for 3 h. Methanol (1.9 mL, 46.8 mmol) was added dropwise and the clear solution was further stirred for 30 min. The solvent was evaporated under reduced pressure to yield methyl 4-chloronicotinate (0.67 g, 3.90 mmol, 50% yield). LCMS (ESI) m/e 172.5 [(M+H)$^+$, calcd for C$_7$H$_7$ClNO$_2$ 172.0]; LCMS retention time (Method D): t$_R$=1.15 min.

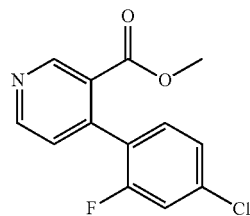 [SMILES: COC(=O)c1cnccc1-c1ccc(Cl)cc1F]

Part B. methyl 4-(4-chloro-2-fluorophenyl)nicotinate

To a stirred solution of methyl 4-chloronicotinate (7 g, 40.8 mmol), (4-chloro-2-fluorophenyl)boronic acid (7.11 g, 40.8 mmol) and cesium carbonate (26.6 g, 82 mmol) in a mixture of dioxane (60 mL) and water (8 mL) purged with nitrogen gas for 5 min, was added Pd(PPh$_3$)$_4$ (2.83 g, 2.448 mmol) and the resultant mixture was heated at 85° C. for 15 h. Water (30 mL) was added and the mixture was extracted with EtOAc (1×50 mL). The organic layer was washed with water (1×30 mL) and brine (1×30 mL), dried over sodium sulfate and concentrated under reduced pressure. The residue was purified via silica gel column (30% EtOAc in hexane) to give methyl 4-(4-chloro-2-fluorophenyl)nicotinate (5 g, 18.82 mmol, 40% yield). LCMS (ESI) m/e 266.7 [(M+H)$^+$, calcd for C$_{13}$H$_{10}$ClFNO$_2$ 266.0]; LCMS retention time (Method C): t$_R$=1.73 min.

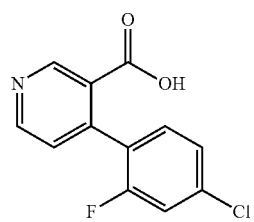 [SMILES: O=C(O)c1cnccc1-c1ccc(Cl)cc1F]

Part C. 4-(4-Chloro-2-fluorophenyl)nicotinic acid

To a solution of methyl 4-(4-chloro-2-fluorophenyl)nicotinate (1 g, 3.76 mmol) in MeOH (10 mL) and water (10 mL) was added NaOH (0.602 g, 15.06 mmol) and the solution stirred at room temperature for 2 h. The volatile organic solvent was evaporated under reduced pressure. The reaction mixture was cooled to 0° C. and acidified with 50% aqueous HCl. The precipitated so formed was collected by vacuum filtration to yield 4-(4-chloro-2-fluorophenyl)nicotinic acid (0.3 g, 1.192 mmol, 30% crude yield) as an off-white solid which was carried directly into the next step. $^1$H NMR (400 MHz, CD$_3$OD) δ 9.12 (s, 1H), 8.78 (d, J=5.20 Hz, 1H), 7.29-7.48 (m, 4H).

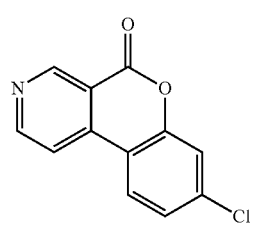 [SMILES: O=c1oc2cc(Cl)ccc2c2ccncc12]

Part D. 8-chloro-5H-chromeno[3,4-c]pyridin-5-one

To a solution of 4-(4-chloro-2-fluorophenyl)nicotinic acid (0.3 g, 1.192 mmol) in anhydrous DMSO (1 mL) was added Cs$_2$CO$_3$ (0.388 g, 1.192 mmol) and the mixture was subjected to microwave heating for 2 h at 60° C. The reaction mixture was diluted with water and extracted with ethyl acetate (2×15 mL). The combined organic extracts were washed with water (1×15 mL) and brine (1×15 mL), dried over sodium sulfate and concentrated under reduced pressure to afford 8-chloro-5H-chromeno[3,4-c]pyridin-5-one (0.2 g, 0.863 mmol, 72% yield over 2 steps). $^1$H NMR (400 MHz, CDCl$_3$) δ 9.57 (d, J=0.40 Hz, 1H), 8.98 (d, J=5.60 Hz, 1H), 8.01 (d, J=8.80 Hz, 1H), 7.88 (q, J=0.40 Hz, 1H), 7.44 (d, J=2.00 Hz, 1H), 7.39 (q, J=2.00 Hz, 1H); LCMS (ESI) m/e 232.6 [(M+H)$^+$, calcd for C$_{12}$H$_7$ClNO$_2$ 232.0]; LCMS retention time (Method D): t$_R$=0.81 min.

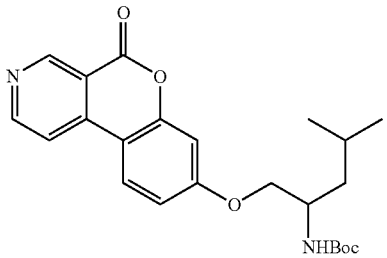 [SMILES: CC(C)CC(COc1ccc2c(c1)oc(=O)c1cnccc12)NC(=O)OC(C)(C)C]

Part E. tert-butyl (4-methyl-1-((5-oxo-5H-chromeno[3,4-c]pyridin-8-yl)oxy)pentan-2-yl)carbamate Tert-butyl (4-methyl-1-((5-oxo-5H-chromeno[3,4-c]pyridin-8-yl)oxy)pentan-2-yl)carbamate was prepared in an analogous fashion to Example 8, Part C to give the titled product (0.18 g, 0.436 mmol, 50% yield). $^1$H NMR (400 MHz, CD$_3$OD) δ 9.36 (s, 1H), 8.85 (d, J=5.6 Hz, 1H), 8.22 (d, J=8.8 Hz, 1H), 8.15 (d, J=5.6 Hz, 1H), 7.08 (m, 1H), 7.01 (d, J=2.4 Hz, 1H), 4.04-4.07 (m, 3H), 1.48 (m, 1H), 1.46 (s, 9H), 1.36 (m, 2H), 0.94-1.01 (m, 6H); LCMS (ESI) m/e 413 [(M+H)$^+$, calcd for C$_{23}$H$_{29}$N$_2$O$_5$ 413.2]; LCMS retention time (Method D): t$_R$=0.96 min.

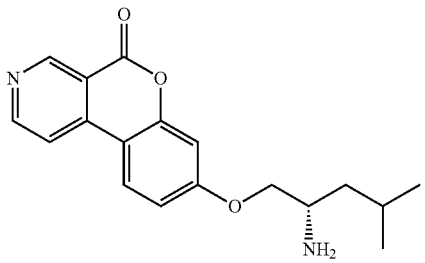 [SMILES: CC(C)C[C@H](N)COc1ccc2c(c1)oc(=O)c1cnccc12]

Part F (S)-8-(2-amino-4-methylpentyloxy)-5H-chromeno[3,4-c]pyridin-5-one

The deprotection of tert-butyl (4-methyl-1-((5-oxo-5H-chromeno[3,4-c]pyridin-8-yl)oxy)pentan-2-yl)carbamate was carried out in an analogous fashion to Example 8, Part D to give (S)-8-(2-amino-4-methylpentyloxy)-5H-chromeno[3,4-c]pyridin-5-one (0.065 g, 0.208 mmol, 44% yield) as a white solid. $^1$H NMR (400 MHz, MeOD) δ 9.37 (s, 1H), 8.80 (d, J=10.6 Hz, 1H), 8.28 (d, J=8.9 Hz, 1H), 8.22 (d, J=5.6 Hz, 1H), 7.17 (m, 1H), 7.09 (d, J=2.4 Hz, 1H), 4.23 (m, 1H), 4.07 (m, 1H), 3.50 (m, 1H), 1.84 (m, 1H), 1.57 (m, 2H), 1.17 (m, 6H); LCMS (ESI) m/e 313.2 [(M+H)$^+$, calcd for C$_{18}$H$_{21}$N$_2$O$_3$ 313.2]; LC/MS retention time (Method C): t$_R$=1.25 min; HPLC retention time (method A): t$_R$=4.90 min; HPLC retention time (method B): t$_R$=5.47 min.

Example 12

(S)—N-(8-(2-amino-4-methylpentyloxy)-5H-chromeno[3,4-c]pyridin-4-yl)acetamide

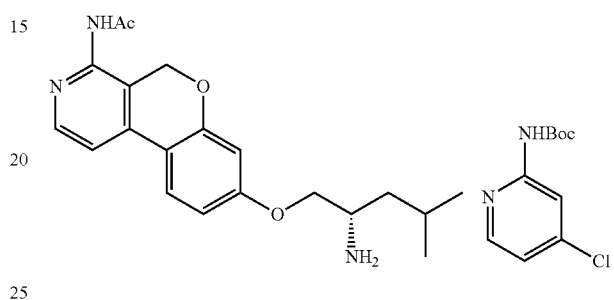

Part A. tert-Butyl 4-chloropyridin-2-ylcarbamate

A stirred solution of 4-chloropicolinic acid (0.2 g, 1.269 mmol), DPPA (0.351 g, 1.269 mmol) and TEA (0.354 mL, 2.54 mmol) in tert-butanol (15 mL) was purged with nitrogen for 5 min and the reaction mixture was heated at 100° C. for 12 h. The mixture was cooled to room temperature and the volatiles were removed under reduced pressure. The reaction mixture was diluted with water (15 mL) and extracted with ethyl acetate (3×15 mL). The combined organic extracts were washed with brine (1×15 mL), dried over sodium sulfate and concentrated under reduced pressure. The residue was purified by silica gel chromatography (15% Ethyl acetate in hexane) to yield tert-butyl (4-chloropyridin-2-yl)carbamate (0.17 g, 0.743 mmol, 59% yield) as a yellow solid. $^1$H NMR (400 MHz, CD$_3$OD) δ 8.23 (d, J=5.2 Hz, 1H), 7.88 (d, J=5.2 Hz, 1H), 7.16 (m, 1H), 1.48 (s, 9H).

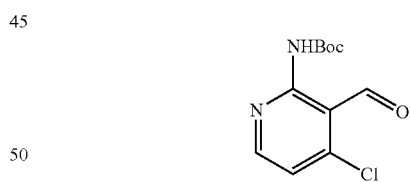

Part B. tert-Butyl 4-chloro-3-formylpyridin-2-ylcarbamate

To a stirred solution of tert-butyl (4-chloropyridin-2-yl) carbamate (1.00 g, 4.37 mmol) in THF (30 mL) cooled to −78° C. was added n-butyllithium (2.55 M in hexane, 4.1 mL, 10.06 mmol) dropwise. After complete addition the solution was stirred at −78° C. for 1 h. DMF (1.591 mL, 20.55 mmol) was added dropwise and the resultant solution stirred at −78° C. for an additional 1 h. The reaction mixture was then quenched by addition of saturated aqueous ammonium chloride solution (20 mL) and extracted with ethyl acetate (2×25 mL). The combined organic extracts were washed with brine (1×20 mL), dried over sodium sulfate and concentrated under reduced pressure. The crude residue was purified via neutral alumina gel chromatography (ethyl acetate/hexanes) to yield tert-butyl (4-chloro-3-formylpyridin-2-yl)carbamate (530 mg, 2.07 mmol, 27% yield) as a yellow solid. $^1$H NMR (400 MHz, CDCl$_3$) δ 10.73 (s, 1H), 10.55 (s, 1H), 8.52 (d, J=5.3 Hz, 1H), 7.06 (d, J=5.3 Hz, 1H), 1.56 (s, 9H); LCMS (ESI) m/e 255.2 [(M–H)$^-$, calcd for C$_{11}$H$_{12}$ClN$_2$O$_3$ 255.0]; LCMS retention time (Method C): t$_R$=1.73 min.

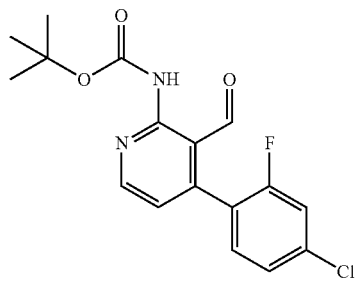 [SMILES: CC(C)(C)OC(=O)Nc1nccc(-c2ccc(Cl)cc2F)c1C=O]

Part C. tent-Butyl 4-(4-chloro-2-fluorophenyl)-3-formylpyridin-2-ylcarbamate

To a stirred suspension of tert-butyl (4-bromo-3-formylpyridin-2-yl)carbamate (100 mg, 0.332 mmol), (4-chloro-2-fluorophenyl)boronic acid (57.9 mg, 0.332 mmol) and cesium carbonate (216 mg, 0.664 mmol) in THF (50 mL) and water (8 ml) was added Pd(PPh$_3$)$_4$ (19.19 mg, 0.017 mmol) and the reaction mixture was heated to 85° C. overnight. The reaction mixture was cooled to room temperature, diluted with water (30 mL) and extracted with ethyl acetate (2×25 mL). The combined organic extracts were washed with brine (1×25 mL), dried over sodium sulfate and concentrated under reduced pressure. The crude residue was purified via silica gel chromatography (ethyl acetate/hexanes) to afford tert-butyl 4-(4-chloro-2-fluorophenyl)-3-formylpyridin-2-ylcarbamate (60 mg, 0.171 mmol, 35% yield). LCMS (ESI) m/e 349.2 [(M–H)$^-$, calcd for C$_{17}$H$_{15}$ClFN$_2$O$_3$ 349.1]; LC/MS retention time (Method C): t$_R$=2.05 min.

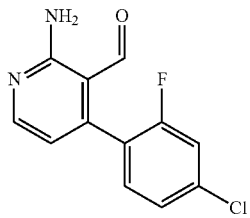 [SMILES: Nc1nccc(-c2ccc(Cl)cc2F)c1C=O]

Part D.
2-Amino-4-(4-chloro-2-fluorophenyl)nicotinaldehyde

To a stirred solution of tert-butyl (4-(4-chloro-2-fluorophenyl)-3-formylpyridin-2-yl)carbamate (0.9 g, 2.57 mmol) in CH$_2$Cl$_2$ (15 mL) was added TFA (3.95 mL, 51.3 mmol) and the reaction mixture was stirred at room temperature for 3 h. The reaction was quenched by addition of saturated aqueous sodium bicarbonate solution (15 mL) and extracted with CH$_2$Cl$_2$ (2×15 mL). The combined organic extracts were washed with brine (1×15 mL), dried over sodium sulfate and concentrated under reduced pressure. The crude 2-amino-4-(4-chloro-2-fluorophenyl)nicotinaldehyde (0.6 g, 2.40 mmol, 41% yield) was carried into the next step without further purification. LCMS (ESI) m/e 251.0 [(M+H)$^+$, calcd for C$_{12}$H$_9$ClFN$_2$O 251.0]; LC/MS retention time (Method C): t$_R$=1.67 min.

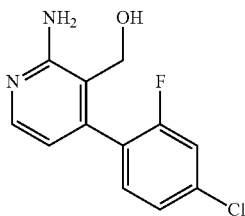 [SMILES: Nc1nccc(-c2ccc(Cl)cc2F)c1CO]

Part E. (2-amino-4-(4-chloro-2-fluorophenyl)pyridin-3-yl)methanol

To a stirred solution of 2-amino-4-(4-chloro-2-fluorophenyl)nicotinaldehyde (50 mg, 0.199 mmol) in MeOH (2 mL) and THF (5 mL) was added sodium borohydride (9.06 mg, 0.239 mmol) then the solution was stirred for 1 h. The volatile organics were removed under reduced pressure and the residue was quenched by addition of saturated aqueous ammonium chloride solution (10 mL). The reaction mixture was extracted with CH$_2$Cl$_2$ (2×10 mL). The combined organic extracts were washed with brine (1×10 mL), dried over sodium sulfate and concentrated under reduced pressure to yield (2-amino-4-(4-chloro-2-fluorophenyl)pyridin-3-yl)methanol (50 mg, 0.198 mmol, 21% yield for two steps). LCMS (ESI) m/e 253 [(M+H)$^+$, calcd for C$_{12}$H$_{11}$ClFN$_2$O 253.0]; LC/MS retention time (Method C): t$_R$=1.48 min.

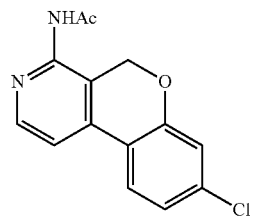 [SMILES: CC(=O)Nc1nccc2c1COc1cc(Cl)ccc1-2]

Part F. N-(8-chloro-5H-chromeno[3,4-c]pyridin-4-yl)acetamide

To a stirred solution of 8-chloro-5H-chromeno[3,4-c]pyridin-4-amine (0.08 g, 0.344 mmol) in pyridine (5 mL) at 0° C. was added acetyl chloride (0.024 mL, 0.344 mmol) and the solution was stirred for 2 h. The volatile organics were removed under reduced pressure and the residue was diluted with water (5 mL). The reaction mixture was extracted with CH$_2$Cl$_2$ (2×15 mL). The combined organic extracts were washed with brine (1×10 mL), dried over sodium sulfate and concentrated under reduced pressure. The crude residue was taken to the next step without purification. LCMS (ESI) m/e 273 [(M)$^-$, calcd for C$_{14}$H$_{10}$ClN$_2$O$_2$ 273.1]; LC/MS retention time (Method C): t$_R$=1.89 min.

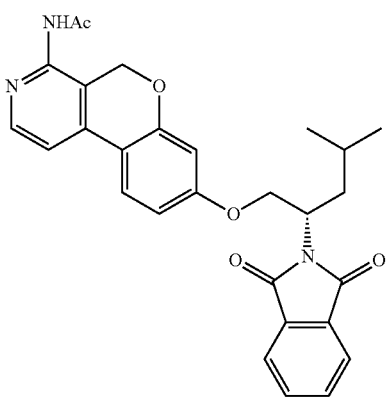 [SMILES: CC(=O)Nc1nccc2c1COc1cc(OC[C@H](CC(C)C)N3C(=O)c4ccccc4C3=O)ccc1-2]

Part G. (S)—N-(8-((2-(1,3-dioxoisoindolin-2-yl)-4-methylpentyl)oxy)-5H-chromeno[3,4-d]pyridin-4-yl)acetamide To a stirred solution of N-(8-chloro-5H-chromeno[3,4-c]pyridin-4-yl)acetamide (47 mg, 0.171 mmol), (S)-2-(1-hydroxy-4-methylpentan-2-yl)isoindoline-1,3-dione (127 mg, 0.513 mmol), 2-di-tert-butylphosphino-2,4,6-triisopropylbiphenyl (43.6 mg, 0.103 mmol), and cesium carbonate (84 mg, 0.257 mmol) in toluene (25 mL) at room temperature was added palladium (II) acetate (11.52 mg, 0.051 mmol). Nitrogen was bubbled through the solution for 5 min, and the mixture heated at 80° C. for 14 h. The reaction mixture was cooled to room temperature and diluted with ethyl acetate (30 mL) then filtered through celite. Water (30 mL) was added and the organic layer was separated and washed with brine (1×25 mL), dried with sodium sulfate and concentrated under reduced pressure. The residue was used without further purification in the next step. LCMS (ESI) m/e 486.2 [(M+H)$^+$, calcd for $C_{28}H_{28}N_3O_5$ 486.2]; LC/MS retention time (Method C): $t_R$=2.07 min.

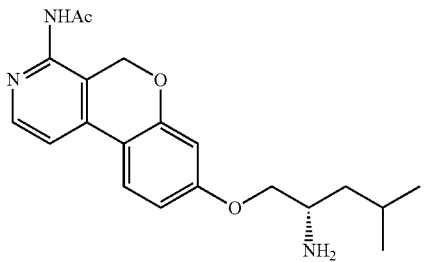 [SMILES: CC(=O)Nc1nccc2c1COc1cc(OC[C@@H](N)CC(C)C)ccc1-2]

Part H. (S)—N-(8-(2-amino-4-methylpentyloxy)-5H-chromeno[3,4-c]pyridin-4-yl)acetamide To a stirred solution of (S)-tert-butyl (1-((4-acetamido-5H-chromeno[3,4-c]pyridin-8-yl)oxy)-4-methylpentan-2-yl)carbamate (150 mg, 0.329 mmol) in CH$_2$Cl$_2$ (10 mL) at room temperature was added TFA (0.025 mL, 0.329 mmol) and the solution was stirred at room temperature for 3 h. The solution was concentrated under reduced pressure and the sample was purified by preparative HPLC (0.1% TFA in water and methanol) yielding (S)—N-(8-((2-amino-4-methylpentyl)oxy)-5H-chromeno[3,4-c]pyridin-4-yl)acetamide (40 mg, 0.113 mmol, 33% yield for three steps) as an off-white solid. $^1$H NMR (400 MHz, CD$_3$OD) δ 8.34 (d, J=5.3 Hz, 1H), 7.81 (d, J=8.7 Hz, 1H), 7.58 (d, J=5.4 Hz, 1H), 6.77 (m, 1H), 6.63 (d, J=2.4 Hz, 1H), 4.94 (s, 2H), 4.03 (m, 1H), 3.85 (m, 1H), 3.33 (m, 1H), 2.21 (s, 3H), 1.81 (m, 1H), 1.43 (m, 2H), 0.99 (m, 6H); LCMS (ESI) m/e 356.2 [(M+H)$^+$, calcd for $C_{20}H_{26}N_3O_3$ 356.2]; LC/MS retention time (Method C): $t_R$=1.26 min; HPLC retention time (method A): $t_R$=8.02 min; HPLC retention time (method B): $t_R$=9.08 min.

Example 13

(S)-8-((2-amino-4-methylpentyl)oxy)-5H-chromeno[3,4-c]pyridin-4-amine

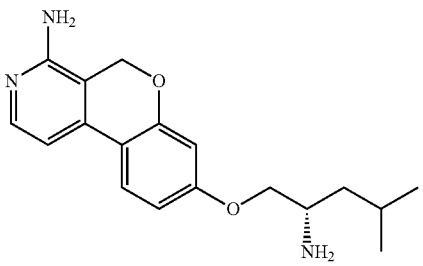 [SMILES: CC(C)C[C@H](N)COc1ccc2c(c1)OCc1c-2ccnc1N]

To a stirred solution of (S)—N-(8-((2-amino-4-methylpentyl)oxy)-5H-chromeno[3,4-c]pyridin-4-yl)acetamide (20 mg, 0.056 mmol) (prepared as in Example 12, Part H) in a mixture of ethanol (10 mL) and water (2 mL) was added KOH (31.6 mg, 0.563 mmol) and the reaction was heated at 70° C. for 14 h. After completion of the reaction, the volatile organic solvent was removed under reduced pressure, water (20 mL) was added and the solution extracted with dichloromethane (2×20 mL). The combined organic extracts were washed with water (1×20 mL), dried over sodium sulfate and concentrated under reduced pressure to obtain (S)-8-((2-amino-4-methylpentyl)oxy)-5H-chromeno[3,4-c]pyridin-4-amine (2.31 mg, 7.15 umol, 13% yield) as an off-white solid. $^1$H NMR (400 MHz, MeOD) δ 7.90 (d, J=5.6 Hz, 1H), 7.69 (d, J=8.7 Hz, 1H), 6.98 (d, J=5.6 Hz, 1H), 6.72 (m, 1H), 6.6 (d, J=2.5 Hz, 1H), 5.07 (s, 2H), 4.10 (m, 1H), 3.92 (m, 1H), 3.40 (m, 1H), 1.82 (m, 1H), 1.49 (m, 2H), 1.01 (m, 6H); LCMS (ESI) m/e 314.2 [(M+H)$^+$, calcd for $C_{18}H_{24}N_3O_2$ 314.2]; LC/MS retention time (Method C): $t_R$=1.21 min; HPLC retention time (method A): $t_R$=7.52 min; HPLC retention time (method B): $t_R$=8.68 min.

Example 14

(S)-1-(9-bromo-5H-chromeno[3,4-c]pyridin-8-yloxy)-4-methylpentan-2-amine

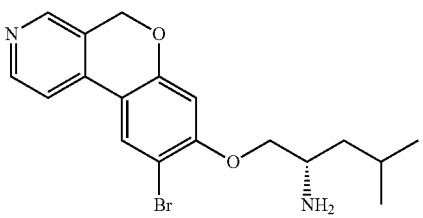

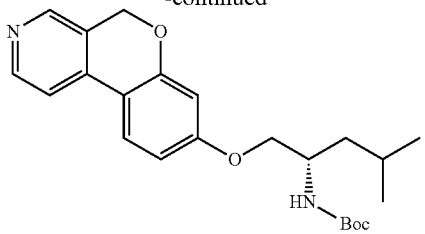

Part A. (S)-tert-butyl 1-(5H-chromeno[3,4-c]pyridin-8-yloxy)-4-methylpentan-2-ylcarbamate To 8-chloro-5H-chromeno[3,4-c]pyridine (0.489 g, 2.247 mmol) (prepared as in Example 5, Part D), (S)-tert-butyl (1-hydroxy-4-methylpentan-2-yl)carbamate (1.474 g, 6.79 mmol), di-tert-butyl(2',4',6'-triisopropyl-[1',1'-biphenyl]-2-yl)phosphine (0.572 g, 1.348 mmol), palladium (II) acetate (0.151 g, 0.674 mmol) and cesium carbonate (1.098 g, 3.37 mmol) was added toluene (4 mL). Nitrogen gas was bubbled through the mixture for 5 min and the mixture heated at 80° C. for 15 h. The reaction mixture was cooled to room temperature and filtered through a bed of celite. Water (10 mL) was added to the filtrate and the product was extracted with ethyl acetate (3×15 mL). The combined organic extracts were washed with brine (1×10 mL), dried with sodium sulfate and concentrated under reduced pressure. The residue so obtained was purified by preparative TLC using (50% ethyl acetate in pet ether) to afford tert-butyl (1-((5H-chromeno[3,4-c]pyridin-8-yl)oxy)-4-methylpentan-2-yl)carbamate (0.4 g, 1.00 mmol, 45% yield) as a semi solid. LCMS (ESI) m/e 399.2 [(M+H)$^1$, calcd for $C_{23}H_{31}N_2O_4$ 399.5]; LC/MS retention time (Method C): $t_R$=2.16 min.

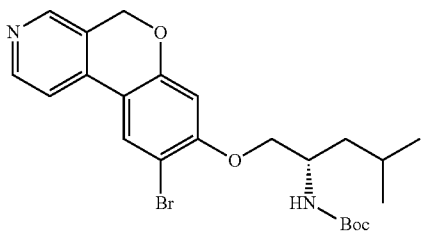 [SMILES: CC(C)C[C@@H](COc1cc2c(cc1Br)-c1ccncc1CO2)NC(=O)OC(C)(C)C]

Part B. (S)-tert-butyl 1-(9-bromo-5H-chromeno[3,4-d]pyridin-8-yloxy)-4-methylpentan-2-ylcarbamate A solution of tert-butyl (1-((5H-chromeno[3,4-c]pyridin-8-yl)oxy)-4-methylpentan-2-yl)carbamate (0.072 g, 0.181 mmol) in acetonitrile (5 mL) cooled to 0° C. and stirred for 2 min. NBS (0.029 g, 0.163 mmol) was added in single portion and the reaction mixture stirred at 0° C. for 2 h. The solvent was removed under reduced pressure and water 10 mL) was added. The product was extracted with ethyl acetate (3×15 mL). The combined organic extracts were washed with water (1×20 mL) dried over sodium sulfate and concentrated under reduced pressure. The residue was purified via preparative TLC (40% EtOAc:pet ether) to obtain (S)-tert-butyl 1-(9-bromo-5H-chromeno[3,4-c]pyridin-8-yloxy)-4-methylpentan-2-ylcarbamate (30 mg, 0.063 mmol, 35% yield). $^1$H NMR (400 MHz, CD$_3$OD) δ 8.48 (d, J=5.4 Hz, 1H), 8.38 (s, 1H), 8.07 (s, 1H), 7.68 (d, J=5.4 Hz, 1H), 6.73 (s, 1H), 5.21 (s, 2H), 4.02-3.98 (m, 3H), 1.92-1.71 (m, 1H), 1.56-1.52 (m, 2H), 0.97 (t, J=6.8 Hz, 6H).

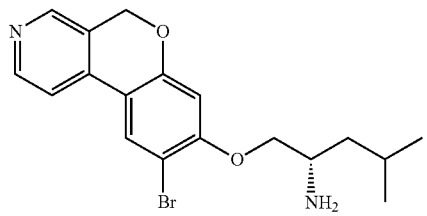 [SMILES: CC(C)C[C@H](N)COc1cc2c(cc1Br)-c1ccncc1CO2]

Part C. (S)-1-(9-bromo-5H-chromeno[3,4-c]pyridin-8-yloxy)-4-methylpentan-2-amine To a solution of tert-butyl (1-((9-bromo-5H-chromeno[3,4-c]pyridin-8-yl)oxy)-4-methylpentan-2-yl)carbamate (0.045 g, 0.094 mmol) in dichloromethane (4 mL) cooled to 0° C. was added hydrogen chloride, 2M in diethyl ether (6 mL, 0.094 mmol) slowly over a period of 5 min. The reaction mixture was stirred at 0° C. for 5 min, then at room temperature for 2 h. The solvents were removed by concentration under reduced pressure. The crude product was taken up in water (10 mL) and washed with diethyl ether (3×10 mL). The aqueous layer was concentrated and purified by reverse phase HPLC (0.1% TFA in water and acetonitrile) to yield 1-((9-bromo-5H-chromeno[3,4-c]pyridin-8-yl)oxy)-4-methylpentan-2-amine (0.016 g, 0.042 mmol, 45% yield) as a yellow solid. $^1$H NMR (400 MHz, CD$_3$OD) δ 8.68 (bs, 2H), 8.35 (s, 1H), 8.26 (s, 1H), 6.90 (s, 1H), 5.39 (s, 2H), 4.41 (m, 1H), 4.27 (m, 1H), 3.76 (m, 1H), 1.82 (m, 2H), 1.69 (m, 1H), 1.05 (m, 6H). LCMS (ESI) m/e 377.0 [(M+H)$^+$, calcd for $C_{18}H_{22}BrN_2O_2$ 377.1]; LC/MS retention time (Method D): $t_R$=1.25 min; HPLC retention time (method A): $t_R$=8.59 min; HPLC retention time (method B): $t_R$=10.33 min.

Example 15

8-(((S)-2-amino-4-methylpentyl)oxy)-5-methyl-5H-chromeno[3,4-c]pyridin-4-amine

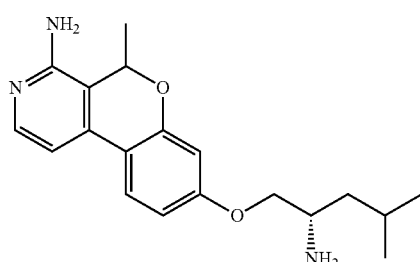

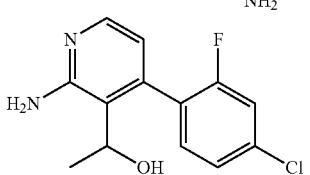

Part A. 1-(2-amino-4-(4-chloro-2-fluorophenyl)pyridin-3-yl)ethanol

To a stirred solution of 2-amino-4-(4-chloro-2-fluorophenyl)nicotinaldehyde (0.2 g, 0.798 mmol) (prepared as described in Example 12, Part D) in THF (15 mL) was added methylmagnesium bromide (3.0 M in THF) (0.82 mL, 2.394 mmol) at −60° C. and the reaction was stirred for 30 min. The reaction was quenched with saturated ammonium chloride solution, extracted with ethyl acetate (2×10 mL). The combined organic layers were washed with brine (1×10 mL), dried over sodium sulphate, and concentrated under reduced pressure to give 1-(2-amino-4-(4-chloro-2-fluorophenyl)pyridin-3-yl)ethanol (0.2 g, 0.691 mmol, 87% yield). LCMS (ESI) m/e 267.0 [(M+H)$^+$, calcd for $C_{13}H_{13}ClFN_2O$ 267.1]; LC/MS retention time (Method D): $t_R$=1.36 min.

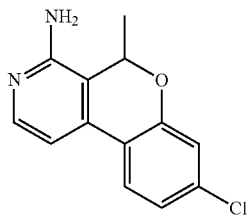 [SMILES: CC1Oc2cc(Cl)ccc2-c2ccnc(N)c21]

Part B. 8-chloro-5-methyl-5H-chromeno[3,4-c]pyridin-4-amine

Prepared as described in Example 5, Part D using 1-(2-amino-4-(4-chloro-2-fluorophenyl)pyridin-3-yl)ethanol to afford 8-chloro-5-methyl-5H-chromeno[3,4-c]pyridin-4-amine (0.15 g, 0.557 mmol, 74% yield). LCMS (ESI) m/e 247.0 [(M+H)$^+$, calcd for $C_{13}H_{12}ClN_2O$ 247.05]; LC/MS retention time (Method D): $t_R$=1.52 min.

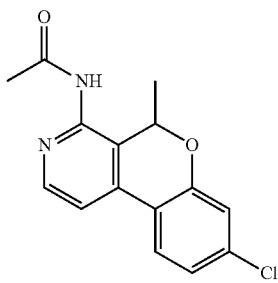 [SMILES: CC(=O)Nc1nccc2c1C(C)Oc1cc(Cl)ccc1-2]

Part C. N-(8-chloro-5-methyl-5H-chromeno[3,4-c]pyridin-4-yl)acetamide

Prepared as described in Example 12, Part F using 8-chloro-5-methyl-5H-chromeno[3,4-c]pyridin-4-amine to afford N-(8-chloro-5-methyl-5H-chromeno[3,4-c]pyridin-4-yl)acetamide (0.142 g, 0.398 mmol, 66% yield). LCMS (ESI) m/e 289.0 [(M+H)$^+$, calcd for $C_{15}H_{14}ClN_2O_2$ 289.1]; LC/MS retention time (Method B): $t_R$=1.62 min.

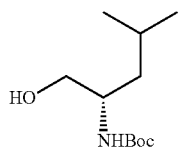

Part D. (S)-tert-butyl (1-hydroxy-4-methylpentan-2-yl)carbamate

To a stirred solution of (S)-2-amino-4-methylpentan-1-ol (5 g, 42.7 mmol) in tetrahydrofuran (100 mL) at rt was added BOC$_2$O (9.91 mL, 42.7 mmol) dropwise and the reaction was stirred at rt for 5 h. After the completion of reaction, solvent was removed under reduced pressure to yield (S)-tert-butyl (1-hydroxy-4-methylpentan-2-yl)carbamate (6.3 g, 29.0 mmol, 68% yield) as a colorless oil. $^1$H NMR (400 MHz, DMSO-d$_6$) δ 6.42 (d, J=8.8 Hz, 1H), 4.55 (m, 1H), 3.32 (m, 1H), 3.27 (m, 1H), 3.17 (m, 1H), 1.47 (m, 1H), 1.37 (s, 9H), 1.22 (m, 2H), 0.85 (m, 6H).

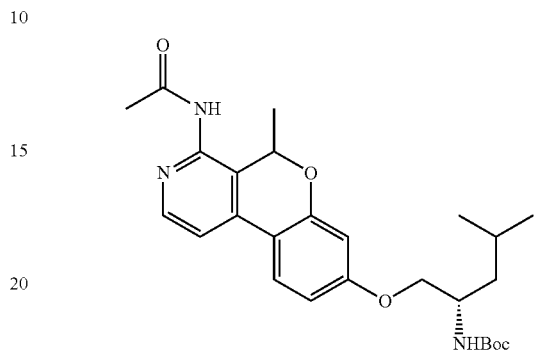

Part E. tert-butyl ((2S)-1-(4-acetamido-5-methyl-5H-chromeno[3,4-d]pyridin-8-yl)oxy)-4-methylpentan-2-yl)carbamate Prepared as described in Example 8, Part C using (S)-tert-butyl (1-hydroxy-4-methylpentan-2-yl)carbamate and N-(8-chloro-5-methyl-5H-chromeno[3,4-c]pyridin-4-yl)acetamide to afford tert-butyl ((2S)-1-((4-acetamido-5-methyl-5H-chromeno[3,4-c]pyridin-8-yl)oxy)-4-methylpentan-2-yl)carbamate (0.6 g, 0.882 mmol, 51% yield) as a yellow solid. LCMS (ESI) m/e 470.2 [(M+H)$^+$, calcd for $C_{26}H_{36}N_3O_5$ 470.3]; LC/MS retention time (Method C): $t_R$=1.89 min.

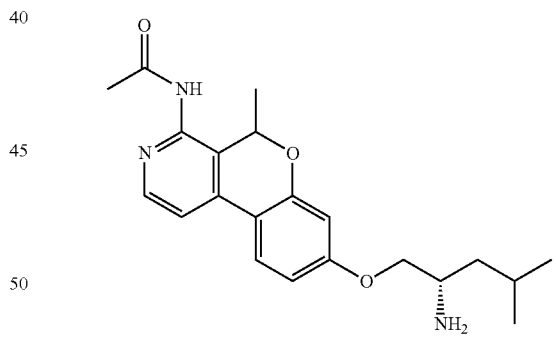

Part F. N-(8-(((S)-2-amino-4-methylpentyl)oxy)-5-methyl-5H-chromeno[3,4-d]pyridin-4-yl)acetamide To a stirred solution of tert-butyl ((2S)-1-((4-acetamido-5-methyl-5H-chromeno[3,4-c]pyridin-8-yl)oxy)-4-methylpentan-2-yl)carbamate (0.15 g, 0.319 mmol) in dichloromethane (25 mL) at room temperature was added TFA (0.246 mL, 3.19 mmol) and the mixture stirred for 12 h. After completion of reaction, the solvent was removed under reduced pressure to afford N-(8-(((S)-2-amino-4-methylpentyl)oxy)-5-methyl-5H-chromeno[3,4-c]pyridin-4-yl)acetamide (0.18 g, 0.281 mmol, 58% yield) as a brown oil. The product was carried forward into the next step without further purification. LCMS (ESI) m/e 370.2 [(M+H)⁺, calcd for C$_{21}$H$_{28}$N$_3$O$_3$ 370.2]; LC/MS retention time (Method C): t$_R$=1.14 min.

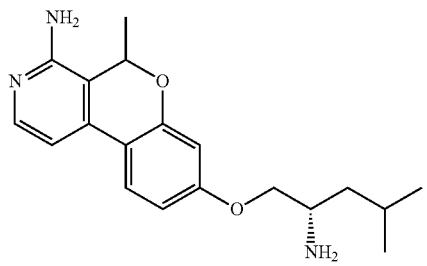 [SMILES: CC(C)C[C@H](N)COc1ccc2c(c1)OC(C)c1c-2ccnc1N]

Part G. 8-(((S)-2-amino-4-methylpentyl)oxy)-5-methyl-5H-chromeno[3,4-c]pyridin-4-amine Prepared as described in Example 13 using N-(8-(((S)-2-amino-4-methylpentyl)oxy)-5-methyl-5H-chromeno[3,4-c]pyridin-4-yl)acetamide to afford 8-(((S)-2-amino-4-methylpentyl)oxy)-5-methyl-5H-chromeno[3,4-c]pyridin-4-amine (15 mg, 0.045 mmol, 9% yield) as a yellow solid. $^1$H NMR (400 MHz, MeOD) δ 7.95 (m, 2H), 7.35 (m, 1H), 6.92 (m, 1H), 6.74 (s, 1H), 5.66 (m, 1H), 4.35 (m, 1H), 4.15 (m, 1H), 3.74 (m, 1H), 1.82-1.72 (m, 3H), 1.52 (m, 3H), 1.04 (m, 6H); LCMS (ESI) m/e 328.2 [(M+H)⁺, calcd for C$_{19}$H$_{26}$N$_3$O$_2$ 328.2]; LC/MS retention time (Method D): t$_R$=1.25 min; HPLC retention time (method A): t$_R$=8.78 min; HPLC retention time (method C): t$_R$=12.78 min.

Example 16

(S)-1-((1-fluoro-5H-chromeno[3,4-c]pyridin-8-yl)oxy)-4-methylpentan-2-amine

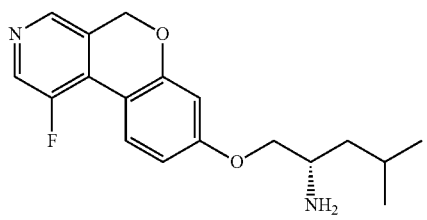

Part A. 4-chloro-5-fluoronicotinic acid

N-Butyllithium, 1.6 M in hexanes (9.50 mL, 15.21 mmol) was added to THF (20 mL) and cooled to −78° C. To this solution was added diisopropylamine (2.167 mL, 15.21 mmol) followed by 4-chloro-3-fluoropyridine (2 g, 15.21 mmol) and the solution stirred for 6 h at −78° C. The reaction mixture was then poured on to crushed dry ice and stirred until the reaction mixture warmed to room temperature. The reaction was quenched by addition of aqueous ammonium chloride solution and acidified to pH=2 using conc. HCl and extracted with ethyl acetate (3×10 mL). The combined organic layers were washed with brine (10 mL), dried over sodium sulphate and concentrated under reduced pressure to afford the 4-chloro-5-fluoronicotinic acid (1.7 g, 9.68 mmol, 64% yield) as a pale yellow solid. LCMS (ESI) m/e 175.9 [(M+H)⁺, calcd for C$_6$H$_4$ClFNO$_2$ 176.0]; LC/MS retention time (Method F): t$_R$=0.57 min.

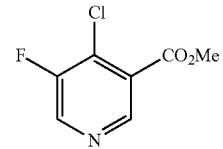 [SMILES: COC(=O)c1cncc(F)c1Cl]

Part B. methyl 4-chloro-5 fluoronicotinate

A solution of 4-chloro-5-fluoronicotinic acid (1.7 g, 9.68 mmol) in acetonitrile (18 mL) was cooled to 0° C. To this solution was added DBU (3.65 mL, 24.21 mmol) dropwise and the resultant solution stirred for 30 min. Iodomethane (3.03 mL, 48.4 mmol) was added dropwise and stirred at room temperature for 12 h. The volatiles were removed completely under reduced pressure and the residue purified via silica gel chromatography using a gradient of ethyl acetate in hexane to afford methyl 4-chloro-5-fluoronicotinate (1.2 g, 6.33 mmol, 65% yield) as a yellow solid. LCMS (ESI) m/e 190.0 [(M+H)⁺, calcd for C$_7$H$_6$ClFNO$_2$ 190.0]; LC/MS retention time (Method F): t$_R$=0.77 min.

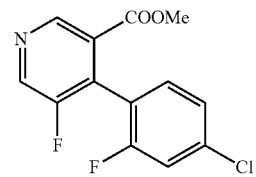 [SMILES: COC(=O)c1cncc(F)c1-c1ccc(Cl)cc1F]

Part C. Methyl 4-(4-chloro-2-fluorophenyl)-5-fluoronicotinate

To a solution of 4-chloro-5-fluoronicotinate (1.2 g, 6.33 mmol) in 1,4-dioxane (12 mL) and water (0.5 mL) was added (4-chloro-2-fluorophenyl)boronic acid (1.214 g, 6.96 mmol) and potassium phosphate, dibasic (2.205 g, 12.66 mmol). To this mixture, PdCl$_2$(dppf) (0.371 g, 0.506 mmol) was added and the solution purged with N$_2$ for 10 min then heated to 80° C. for 12 h. The mixture was cooled to room temperature and water (25 mL) was added. The solution was extracted with ethyl acetate (3×25 mL). The combined organic layers were washed with brine (25 mL) and concentrated under reduced pressure to afford the residue which was purified by silica gel column using a gradient of ethyl acetate in hexanes to afford methyl 4-(4-chloro-2-fluorophenyl)-5-fluoronicotinate (900 mg, 3.17 mmol, 50% yield) as a yellow solid. LCMS (ESI) m/e 284.0 [(M+H)⁺, calcd for C$_{13}$H$_9$ClF$_2$NO$_2$ 284.0]; LC/MS retention time (Method F): t$_R$=1.01 min.

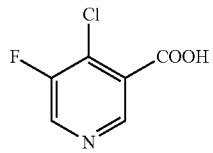

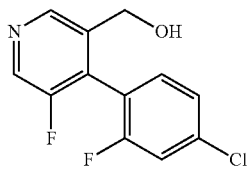 [SMILES: OCc1cncc(F)c1-c1ccc(Cl)cc1F]

Part D. (4-(4-chloro-2-fluorophenyl)-5-fluoropyridin-3-yl)methanol

To a solution of 4-(4-chloro-2-fluorophenyl)-5-fluoronicotinate (300 mg, 1.058 mmol) in tetrahydrofuran (7 mL) cooled to 0° C. was added LAH (0.441 mL, 1.058 mmol) in THF dropwise and the solution was stirred for 30 min. The reaction was then warmed to room temperature and stirred for 12 h. The reaction was quenched with saturated aqueous ammonium chloride (5 mL) and extracted with ethyl acetate (2×5 mL). The combined organic layers were dried over sodium sulphate and concentrated under reduced pressure to afford (4-(4-chloro-2-fluorophenyl)-5-fluoropyridin-3-yl) methanol (200 mg, 0.782 mmol, 74% yield) as a pale brown oil. LCMS (ESI) m/e 255.9 [(M+H)$^+$, calcd for $C_{12}H_9ClF_2NO$ 256.0]; LC/MS retention time (Method F): $t_R$=0.89 min.

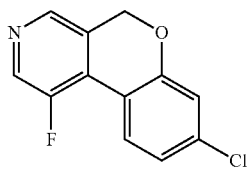 [SMILES: Fc1cncc2c1-c1ccc(Cl)cc1OC2]

Part E.
8-chloro-1-fluoro-5H-chromeno[3,4-d]pyridine

Prepared as described in Example 8, Part B using (4-(4-chloro-2-fluorophenyl)-5-fluoropyridin-3-yl)methanol to afford 8-chloro-1-fluoro-5H-chromeno[3,4-c]pyridine (35 mg, 0.149 mmol, 19% yield) as a white solid. LCMS (ESI) m/e 235.9 [(M+H)$^+$, calcd for $C_{12}H_8ClFNO$ 236.0]; LC/MS retention time (Method F): $t_R$=0.92 min.

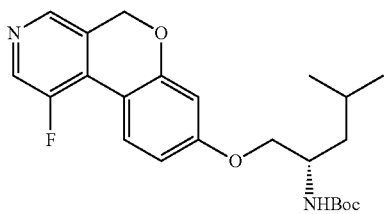 [SMILES: CC(C)C[C@@H](COc1ccc2c(c1)OCc1cncc(F)c1-2)NC(=O)OC(C)(C)C]

Part F. (S)-tert-butyl (1-((1-fluoro-5H-chromeno[3,4-d]pyridin-8-yl)oxy)-4-methylpentan-2-yl)carbamate Prepared as described in Example 8, Part C using 8-chloro-1-fluoro-5H-chromeno[3,4-c]pyridine to afford (S)-tert-butyl (1-((1-fluoro-5H-chromeno[3,4-c]pyridin-8-yl)oxy)-4-methylpentan-2-yl)carbamate (35 mg, 0.084 mmol, 66% yield) as a pale yellow solid. LCMS (ESI) m/e 417.1 [(M+H)$^+$, calcd for $C_{23}H_{30}FN_2O_4$ 417.2]; LC/MS retention time (Method F): $t_R$=1.00 min.

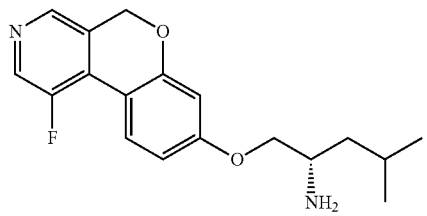 [SMILES: CC(C)C[C@H](N)COc1ccc2c(c1)OCc1cncc(F)c1-2]

Part G. (S)-1-(1-fluoro-5H-chromeno[3,4-c]pyridin-8-yl)oxy)-4-methylpentan-2-amine Prepared as described Example 8, Part D using (S)-tert-butyl (1-((1-fluoro-5H-chromeno[3,4-c]pyridin-8-yl)oxy)-4-methylpentan-2-yl)carbamate to afford (S)-1-((1-fluoro-5H-chromeno[3,4-c]pyridin-8-yl)oxy)-4-methylpentan-2-amine, 2 TFA (12.47 mg, 0.022 mmol, 26% yield) as a white solid. $^1$H NMR (400 MHz, MeOD) δ 9.46 (d, J=3.2 Hz, 1H), 8.29 (s, 1H), 8.05 (d, J=9.2 Hz, 1H), 6.87 (m, 1H), 6.77 (d, J=2.4 Hz, 1H), 5.2 (s, 2H), 4.33 (m, 1H), 4.12 (m, 1H), 3.69 (m, 1H), 1.85-1.71 (m, 3H), 1.1 (m, 6H). LCMS (ESI) m/e 317.0 [(M+H)$^+$, calcd for $C_{18}H_{22}FN_2O_2$ 317.2]; LC/MS retention time (Method F): $t_R$=0.62 min; HPLC retention time (method A): $t_R$=10.68 min; HPLC retention time (method B): $t_R$=11.50 min.

Example 17

1-(5H-chromeno[3,4-d]pyridin-8-yloxy)-5,5,5-trifluoropentan-2-amine

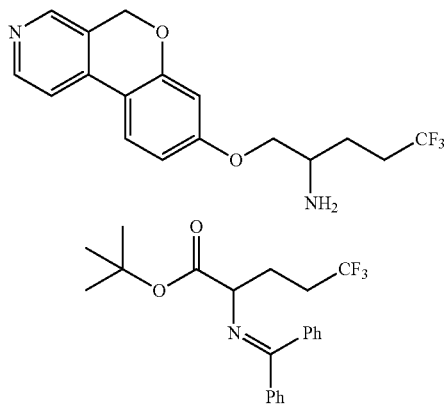

Part A. tert-butyl 2-(diphenylmethyleneamino)-5,5,5-trifluoropentanoate

To a stirred solution of tert-butyl 2-((diphenylmethylene) amino)acetate (1 g, 3.39 mmol) in THF (20 ml) cooled to −78° C. under nitrogen atmosphere was added LDA, 2M in THF/heptane/ethylbenzene (2.54 ml, 5.08 mmol) dropwise for 30 mins. To this mixture was then added 3,3,3-trifluoropropyl trifluoromethanesulfonate (1.083 g, 4.40 mmol). The reaction was gradually warmed to rt and stirred for 4 h. The reaction mixture was quenched by addition of saturated aqueous ammonium chloride at 0° C. The reaction mixture was then extracted with ethyl acetate (3×10 mL). The combined organic extracts were washed with water and brine, dried over sodium sulfate and then concentrated under reduced pressure. The crude product was purified by silica gel column chromatography using 2% ethyl acetate in hexane to afford tert-butyl 2-((diphenylmethylene)amino)-5,5,5-trifluoropentanoate (800 mg, 2.02 mmol, 60% yield) as a yellow oil. LCMS (ESI) m/e 391.9 [(M+H)$^+$, calcd for $C_{22}H_{24}F_3NO_2$, 392.2]; LC/MS retention time (method E): $t_R$=2.49 min.

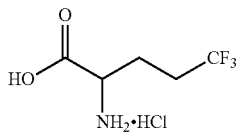

Part B. (S)-2-amino-5,5,5-trifluoropentanoic acid (Hydrochloride salt)

A stirred solution of tert-butyl 2-((diphenylmethylene)amino)-5,5,5-trifluoropentanoate (800 mg, 2.023 mmol) in 50% aqueous hydrochloric acid (0.123 mL, 2.023 mmol) was heated to reflux at 100° C. for 8 h. The reaction mixture was cooled to rt and washed with ethyl acetate (10 mL). The aqueous layer was concentrated under reduced pressure to afford 2-amino-5,5,5-trifluoropentanoic acid hydrochloride (400 mg, 1.82 mmol, 90% yield) as white solid. LCMS (ESI) m/e 171.7 [(M+H)$^+$, calcd for $C_5H_7F_3O_2$, 172.1]; LC/MS retention time (method H): $t_R$=0.80 min.

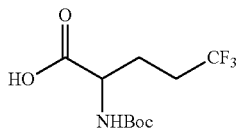

Part C. (S)-2-(tert-butoxycarbonylamino)-5,5,5-trifluoropentanoic acid

To a stirred solution of 2-amino-5,5,5-trifluoropentanoic acid hydrochloride (400 mg, 1.503 mmol) in THF (8 mL) and water (8 mL) was added $K_2CO_3$ (831 mg, 6.01 mmol) at rt and the solution was stirred for 10 min. To this mixture was added $BOC_2O$ (656 mg, 3.01 mmol). The reaction mixture was stirred for 8 h at rt. The reaction mixture was concentrated under reduced pressure. The aq. layer was washed with ethyl acetate (3×5 mL). The aqueous layer was acidified with saturated citric acid solution (5 mL) and then extracted with ethyl acetate (3×8 mL). The combined organic layers were washed with water (3×5 mL) followed by brine (10 mL), dried over sodium sulfate and concentrated under reduced pressure to afford 2-((tert-butoxycarbonyl)amino)-5,5,5-trifluoropentanoic acid (500 mg, 1.84 mmol) quantitatively as a colorless oil. The crude material was taken as such to the next step without further purification. $^1$H NMR (400 MHz, CDCl$_3$) δ 5.04 (s, 1H), 4.38 (s, 1H), 2.15-2.28 (m, 2H), 1.91-1.95 (m, 2H), 1.46 (s, 9H).

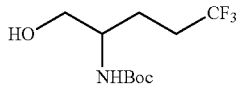

Part D. tert-butyl 5,5,5-trifluoro-1-hydroxypentan-2-ylcarbamate

To a stirred solution of 2-((tert-butoxycarbonyl)amino)-5,5,5-trifluoropentanoic acid (500 mg, 1.843 mmol) in THF (15 ml) cooled to −10° C. under a nitrogen atmosphere was added N-methylmorpholine (0.223 ml, 2.028 mmol) followed by isobutyl chloroformate (0.266 ml, 2.028 mmol) dropwise and stirred for 30 min. The reaction mixture was filtered. The filtrate was added to sodium borohydride (147 mg, 3.87 mmol) in water (10 mL) and stirred for 5 min. The mixture was diluted with ethyl acetate (10 mL). The organic layer was separated and washed with brine (2×10 mL), dried ($Na_2SO_4$) and evaporated under reduced pressure to afford tert-butyl (5,5,5-trifluoro-1-hydroxypentan-2-yl)carbamate (400 mg, 1.55 mmol, 84% yield) as a white solid which was taken to the next step without any purification. $^1$H NMR (400 MHz, CDCl$_3$) δ 3.73-3.59 (m, 3H), 2.24-2.16 (m, 2H), 1.87-1.69 (m, 2H), 1.44 (s, 9H).

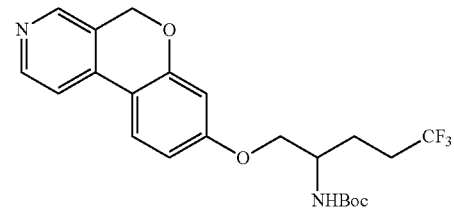 [SMILES: CC(C)(C)OC(=O)NC(CCC(F)(F)F)COc1ccc2c(c1)OCc1cnccc1-2]

Part E. tert-butyl 1-(5H-chromeno[3,4-c]pyridin-8-yloxy)-5,5,5-trifluoropentan-2-ylcarbamate Prepared as described in Example 8, Part C using 8-chloro-5H-chromeno[3,4-c]pyridine to afford tert-butyl (1-((5H-chromeno[3,4-c]pyridin-8-yl)oxy)-5,5,5-trifluoropentan-2-yl)carbamate (25 mg, 9.12 μmol, 4% yield) as a brownish solid. LCMS (ESI) m/e 439.2 [(M+H)$^+$, calcd for $C_{22}H_{26}F_3N_2O_4$, 439.2]
LC/MS retention time (method C): $t_R$=2.04 min.

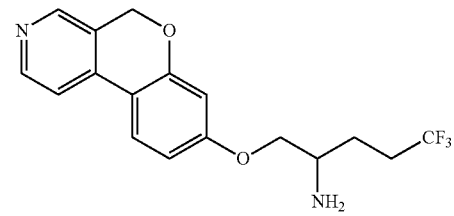 [SMILES: NC(CCC(F)(F)F)COc1ccc2c(c1)OCc1cnccc1-2]

Part F. 1-(5H-chromeno[3,4-c]pyridin-8-yloxy)-5,5,5-trifluoropentan-2-amine

Prepared as described in Example 8, Part D using tert-butyl (1-((5H-chromeno[3,4-c]pyridin-8-yl)oxy)-5,5,5-trifluoropentan-2-yl)carbamate to afford 1-(5H-chromeno[3,4-c]pyridin-8-yloxy)-5,5,5-trifluoropentan-2-amine (15 mg, 0.041 mmol, 18% yield) as a yellow oil. $^1$H NMR (400 MHz, MeOD) δ 8.68 (m, 2H), 8.27 (d, J=6.4 Hz, 1H), 8.11 (d, J=8.8 Hz, 1H), 6.97 (m, 1H), 6.83 (d, J=2.4 Hz, 1H), 5.39 (s, 2H), 4.39 (m, 1H), 4.26 (m, 1H), 3.78 (m, 1H), 2.5-2.43 (m, 2H), 2.15-2.07 (m, 2H); LCMS (ESI) m/e 339.1 [(M+H)$^+$, calcd for $C_{17}H_{15}F_3N_2O_2$ 339.1]; LC/MS retention time (Method E): $t_R$=1.76 min; HPLC retention time (method A): $t_R$=7.46 min; HPLC retention time (method B): $t_R$=8.75 min.

Example 18

(S)—N-(8-(2-amino-4-methylpentyloxy)-5H-chromeno[3,4-c]pyridin-2-yl)acetamide

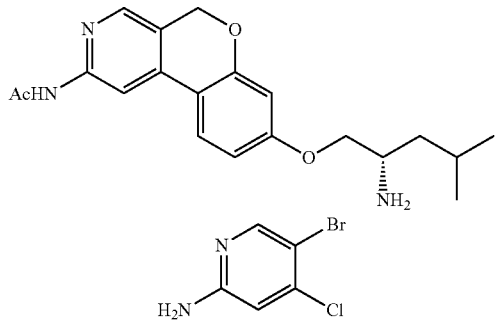

Part A. 4-chloropyridin-2-amine

To a stirred solution of 4-chloropyridin-2-amine (8 g, 62.2 mmol) in acetonitrile (600 mL) at rt was added NBS (11.08 g, 62.2 mmol) in portions and the reaction was stirred for 14 h. The reaction mixture was concentrated under reduced pressure. The residue was reconstituted in ethyl acetate and water. The organics were extracted with ethyl acetate (3×50 mL). The combined organic layers were washed with water (100 mL), brine (100 mL), and dried over sodium sulphate. The organics were concentrated under reduced pressure to afford 5-bromo-4-chloropyridin-2-amine as yellow solid (13 g, 99% yield) that was used without further purification in the next step. LCMS (ESI) m/e 207.0 [(M+H)$^+$, calcd for $C_5H_5BrClN_2$ 206.9]; LC/MS retention time (method B): $t_R$=0.8 min; $^1$H NMR (400 MHz, CDCl$_3$) δ 8.17 (s, 1H), 6.63 (s, 1H), 4.59 (s, 2H).

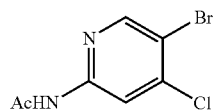

Part B. N-(5-bromo-4-chloropyridin-2-yl)acetamide

To a stirred solution of 5-bromo-4-chloropyridin-2-amine (11.6 g, 55.9 mmol) in pyridine (100 mL) at 0° C. was added acetyl chloride (3.98 mL, 55.9 mmol) and the reaction was stirred at rt for 3 hours. The reaction was quenched with cold water. The reaction mixture was concentrated under reduced pressure. The residue was reconstituted in ethyl acetate and water. The organics were extracted with ethyl acetate (3×50 mL). The combined organic layers were washed with water (100 mL), brine (100 mL) and dried over sodium sulfate. The organics were concentrated under reduced pressure to afford N-(5-bromo-4-chloropyridin-2-yl)acetamide as a white solid (14.6 g, 55.9 mmol, quantitative yield) that was used without further purification in the next step. LCMS (ESI) m/e 249 [(M+H)$^+$, calcd for $C_7H_7BrClN_2O$ 248.9 LC/MS retention time (method B): $t_R$=1.64 min; $^1$H NMR (400 MHz, DMSO-d$_6$) δ 10.87 (s, 1H), 8.58 (s, 1H), 8.33 (s, 1H), 2.11 (s, 3H).

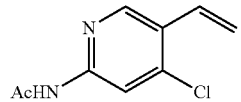

Part C. N-(4-chloro-5-vinylpyridin-2-yl)acetamide

To a stirred solution of N-(5-bromo-4-chloropyridin-2-yl)acetamide (7 g, 28.1 mmol), 2,4,6-trivinyl-1,3,5,2,4,6-trioxatriborinane complex with pyridine (1:1) (8.78 g, 36.5 mmol), and sodium carbonate (5.95 g, 56.1 mmol) solution in 7 mL of water in a mixture of toluene (50 mL) and ethanol (8 mL), was added Pd(PPh$_3$)$_4$ (0.973 g, 0.842 mmol). The solution was purged with nitrogen gas was bubbled for 5 min then heated at 85° C. for 14 h. The reaction was cooled to room temperature and was diluted with ethyl acetate (50 mL) ten filtered through a bed of celite. The filtrate was diluted with water and the organic layer was separated, washed with brine, dried over sodium sulphate. The organics were concentrated under reduced pressure and residue was purified by silica gel column chromatography using a gradient of ethyl acetate in hexanes. Product eluted at 30% ethyl acetate in hexane and required fractions were concentrated to yield N-(4-chloro-5-vinylpyridin-2-yl)acetamide (5.92 g, 27.7 mmol, 99% yield) as yellow solid. LCMS (ESI) m/e 197.2 [(M+H)$^+$, calcd for $C_9H_{10}ClN_2O$ 197.04] LC/MS retention time (method A): $t_R$=1.50 min; $^1$H NMR (400 MHz, DMSO-d$_6$) δ 10.79 (s, 1H), 8.64 (s, 1H), 8.18 (d, J=6.40 Hz, 1H), 6.88 (dd, J=11.2, 17.6 Hz, 1H), 5.99 (dd, J=17.60, 0.80 Hz, 1H), 5.47 (dd, J=11.40, 0.80 Hz, 1H), 2.12 (s, 3H).

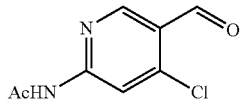

Part D. N-(4-chloro-5-formylpyridin-2-yl)acetamide

To a stirred solution of N-(4-chloro-5-vinylpyridin-2-yl)acetamide (6 g, 30.5 mmol) and 2,6-lutidine (7.11 mL, 61.0 mmol) in a mixture of dioxane (110 mL) and water (25 mL) at 0° C. was added osmium tetroxide, 2.5 wt % solution in 2-methyl-2-propanol (9.58 mL, 30.5 mmol) followed by the addition of sodium periodate (19.58 g, 92 mmol) and the reaction was stirred for 4 h. The reaction mixture was diluted with water and extracted with ethyl acetate (2×100 mL). The combined organic layers were washed with brine solution, dried over sodium sulphate, concentrated under reduced pressure. The residue was purified by silica column using hexane/Ethyl acetate to yield N-(4-chloro-5-formylpyridin-2-yl)acetamide as an off-white solid (5.8 g, 28.1 mmol, 92% yield). LCMS (ESI) m/e 197.0 [(M)$^-$, calcd for $C_8H_6ClN_2O_2$ 197.04] LC/MS retention time (method A): $t_R$=1.21 min; $^1$H NMR (400 MHz, DMSO-d$_6$) δ 11.20 (s, 1H), 10.18 (s, 1H), 8.76 (s, 1H), 8.27 (s, 1H), 2.16 (s, 3H).

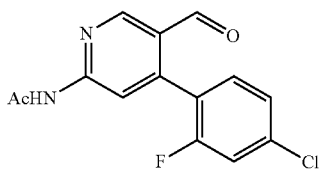 [SMILES: CC(=O)Nc1cc(-c2ccc(Cl)cc2F)c(C=O)cn1]

Part E. N-(4-(4-chloro-2-fluorophenyl)-5-formylpyridin-2-yl)acetamide

To a stirred solution of N-(4-chloro-5-formylpyridin-2-yl)acetamide (3 g, 15.11 mmol), (4-chloro-2-fluorophenyl)boronic acid (2.63 g, 15.11 mmol), cesium carbonate (9.84 g, 30.2 mmol) in a mixture of water (8 mL) and THF (25 mL) was added Pd(PPh$_3$)$_4$ (19.19 mg, 0.017 mmol) and the reaction was heated to 85° C. for 12 h. The reaction mixture was diluted with water and extracted with ethyl acetate (2×25 mL). The combined organic layers were washed with water, brine, dried over sodium sulphate, and concentrated under reduced pressure. The residue was purified by silica gel chromatography using hexane/ethyl acetate as eluant yielding N-(4-(4-chloro-2-fluorophenyl)-5-formylpyridin-2-yl)acetamide (2.8 g, 9.01 mmol, 60% yield) as an off-white solid. LCMS (ESI) m/e 291.0 [(M)$^-$, calcd for C$_{14}$H$_9$ClFN$_2$O$_2$ 291.0] LC/MS retention time (method A): t$_R$=1.69 min; $^1$H NMR (400 MHz, DMSO-d$_6$) δ 11.14 (s, 1H), 9.84 (d, J=Hz, 1H), 8.88 (s, 1H), 8.13 (s, 1H), 7.61 (dd, J=2.00, 10.00 Hz, 1H), 7.46-7.48 (m, 2H), 2.11 (s, 3H).

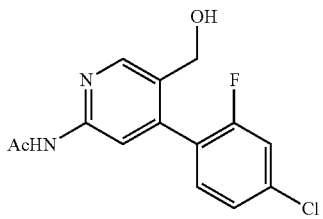 [SMILES: CC(=O)Nc1cc(-c2ccc(Cl)cc2F)c(CO)cn1]

Part F. N-(4-(4-chloro-2-fluorophenyl)-5-(hydroxymethyl)pyridin-2-yl)acetamide Prepared as described in Example 5, Part C using N-(4-(4-chloro-2-fluorophenyl)-5-formylpyridin-2-yl)acetamide (9 g, 24.29 mmol) to afford N-(4-(4-chloro-2-fluorophenyl)-5-(hydroxymethyl)pyridin-2-yl)acetamide (9 g, quantitative yield) as a brown oil. This was taken to the next step without purification. LCMS (ESI) m/e 295.2 [(M)$^-$, calcd for C$_{14}$H$_{13}$ClFN$_2$O$_2$ 295.1] LC/MS retention time (method E): t$_R$=1.44 min.

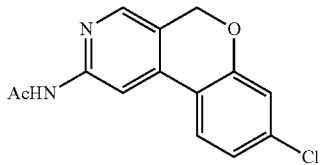 [SMILES: CC(=O)Nc1cc2c(cn1)COc1cc(Cl)ccc1-2]

Part G. N-(8-chloro-5H-chromeno[3,4-c]pyridin-2-yl)acetamide

To a stirred solution of N-(4-(4-chloro-2-fluorophenyl)-5-(hydroxymethyl)pyridin-2-yl)acetamide (9 g, 23.82 mmol) in DMF (90 mL) was added potassium carbonate (9.88 g, 71.5 mmol) and the resultant mixture was sealed tightly and heated at 95° C. for 16 h. The reaction mixture was then cooled to room temperature and volatiles were removed under reduced pressure. The crude material was taken up in water (200 mL) and filtered. The residue was washed with water (2×250 mL) and dried under reduced pressure for 16 h to afford N-(8-chloro-5H-chromeno[3,4-c]pyridin-2-yl)acetamide (5.5 g, 20.02 mmol, 84% yield) as a pale brown solid. LCMS (ESI) m/e 275.2 [(M)$^-$, calcd for C$_{14}$H$_{12}$ClN$_2$O$_2$ 275.1] LC/MS retention time (method D): t$_R$=1.77 min; $^1$H NMR (400 MHz, DMSO-d$_6$) δ 10.6 (s, 1H), 8.41 (s, 1H), 8.25 (s, 1H), 7.78 (d, J=8.4 Hz, 1H), 7.22-7.15 (m, 2H), 5.2 (s, 2H), 2.2 (s, 3H).

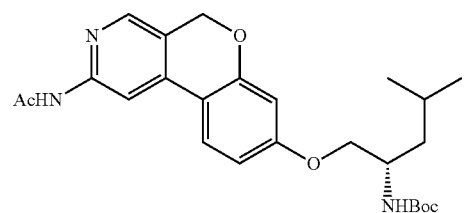 [SMILES: CC(=O)Nc1cc2c(cn1)COc1cc(OC[C@H](CC(C)C)NC(=O)OC(C)(C)C)ccc1-2]

Part H. (S)-tert-butyl 1-(2-acetamido-5H-chromeno[3,4-d]pyridin-8-yloxy)-4-methylpentan-2-ylcarbamate A stirred suspension of N-(8-chloro-5H-chromeno[3,4-c]pyridin-2-yl)acetamide (2.5 g, 9.10 mmol), (S)-tert-butyl (1-hydroxy-4-methylpentan-2-yl)carbamate (5.93 g, 27.3 mmol), di-tert-butyl(2',4',6'-triisopropyl-3-methoxy-6-methyl-[1,1'-biphenyl]-2-yl)phosphine (RockPhos) (0.171 g, 0.364 mmol), cesium carbonate (4.45 g, 13.65 mmol) and molecular sieves 4 Å (1.5 g, 9.10 mmol) in toluene (10 mL) were purged with argon gas for 10 min then treated with allylpalladium(II) chloride (0.067 g, 0.182 mmol). Argon gas was bubbled again for 15 min and the resultant mixture was sealed tightly and heated at 90° C. for 21 h. The reaction was cooled to room temperature and diluted with ethyl acetate (15 mL) and filtered through celite pad. The filtrate was evaporated under reduced pressure to afford crude material which was purified by column chromatography on silica gel (3% methanol in chloroform) to afford the required product contaminated with Boc-leucinol. The oily mixture was then was treated with hexane (2×10 mL) to afford white solid which was purified by SFC method (Column: Chiracel OJ-H, (250× 4.6)mm, 5 g, 0.5% DEA in acetonitrile) to afford (S)-tert-butyl(1-((2-acetamido-5H-chromeno[3,4-c]pyridin-8-yl)oxy)-4-methylpentan-2-yl)carbamate (2.4 g, 5.24 mmol, 58% yield). $^1$H NMR (400 MHz, MeOD) δ 8.31 (s, 1H), 8.09 (s, 1H), 7.72 (d, J=8.4 Hz, 1H), 6.71 (dd, J=2.4 Hz, J=8.8 Hz, 1H), 6.56 (d, J=2.4 Hz, 1H), 5.09 (s, 2H), 3.95 (m, 3H), 2.20 (s, 3H), 1.72 (m, 1H), 1.51-1.39 (m, 2H), 1.47 (s, 9H), 1.16 (m, 6H).

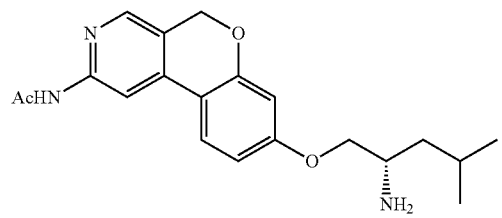 [SMILES: CC(=O)Nc1cc2c(cn1)COc1cc(OC[C@@H](N)CC(C)C)ccc1-2]

Part I. (S)—N-(8-(2-amino-4-methylpentyloxy)-5H-chromeno[3,4-c]pyridin-2-yl)acetamide Prepared as described in Example 8, Part D using (S)-tert-butyl 1-(2-acetamido-5H-chromeno[3,4-c]pyridin-8-yloxy)-4-methylpentan-2-ylcarbamate (4.8 g, 10.54 mmol) to afford (S)—N-(8-(2-amino-4-methylpentyloxy)-5H-chromeno[3,4-c]pyridin-2-yl)acetamide (3.26 g, 9.06 mmol, 86% yield) as a yellow solid. LCMS (ESI) m/e 356.2 [(M)$^-$, calcd for $C_{20}H_{26}N_3O_3$ 356.2] LC/MS retention time (method H): $t_R$=1.55 min; $^1$H NMR (400 MHz, MeOD) δ 8.31 (s, 1H), 8.15 (s, 1H), 7.83 (d, J=8.4 Hz, 1H), 6.85 (dd, J=2.4 Hz, 8.8 Hz, 1H), 6.71 (d, J=2.8 Hz, 1H), 5.15 (s, 2H), 4.31 (dd, J=3.2 Hz, 10.8 Hz, 1H), 4.11 (dd, J=6.4 Hz, 10.4 Hz, 1H), 3.72 (m, 1H), 2.25 (s, 3H), 1.65-1.85 (m, 3H), 1.04 (m, 6H).

Example 19

(S)-4-methyl-1-(spiro[chromeno[3,4-c]pyridine-5,3'-oxetan]-8-yloxy)pentan-2-amine

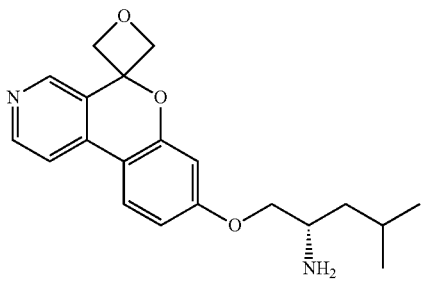

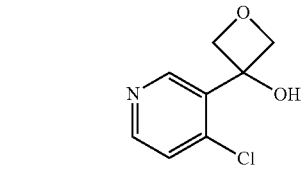

Part A. 3-(4-chloropyridin-3-yl)oxetan-3-ol

4-Chloropyridine (5 g, 44.0 mmol) hydrochloride salt was dried by azeotropic distillation with anhydrous toluene in a round bottomed flask. To this, anhydrous THF (100 mL) was added under nitrogen atmosphere and cooled to −78° C. After 15 min, LDA, 2M in THF/heptane/ethylbenzene (48.4 mL, 97 mmol) was added dropwise and the reaction stirred for 30 min. Oxetan-3-one (3.81 g, 52.8 mmol) was then added and reaction was stirred for 5 min at −78° C. and then cold bath was removed and reaction was allowed to warm to room temperature gradually (~1 h). The reaction was quenched by addition of aqueous ammonium chloride and organics extracted with ethyl acetate (3×50 mL). The combined organic extracts were dried and concentrated under reduced pressure to afford 3-(4-chloropyridin-3-yl)oxetan-3-ol (3.8 g, 20.47 mmol, 46% yield) as a yellow oil.

$^1$H NMR (400 MHz, DMSO-$d_6$) δ 8.6 (s, 1H), 8.51 (d, J=5.6 Hz, 1H), 7.56 (d, J=5.2 Hz, 1H), 6.46 (s, 1H), 5.14 (m, 2H), 4.73 (m, 2H).

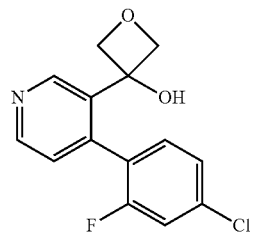 [SMILES: OC1(c2cnccc2-c2ccc(Cl)cc2F)COC1]

Part B. 3-(4-(4-chloro-2-fluorophenyl)pyridin-3-yl)oxetan-3-ol

Prepared as described in Example 5, Part B using 3-(4-chloropyridin-3-yl)oxetan-3-ol to afford 3-(4-(4-chloro-2-fluorophenyl)pyridin-3-yl)oxetan-3-ol (750 mg, 2.68 mmol, 50% yield) as an off-white solid. LCMS (ESI) m/e 280.0 [(M+H)$^+$, calcd for $C_{14}H_{12}ClFNO_2$ 280.0]; LC/MS retention time (Method E): $t_R$=1.90 min.

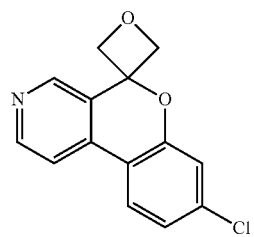 [SMILES: Clc1ccc2c(c1)OC1(COC1)c1cnccc1-2]

Part C. 8-chlorospiro[chromeno[3,4-e]pyridine-5,3'-oxetane]

Prepared as described in Example 5, Part D using 3-(4-(4-chloro-2-fluorophenyl)pyridin-3-yl)oxetan-3-ol to afford 8-chlorospiro[chromeno[3,4-c]pyridine-5,3'-oxetane] (40 mg, 0.154 mmol, 22% yield) as a light brown solid. LCMS (ESI) m/e 260.0 [(M+H)$^+$, calcd for $C_{14}H_1ClNO_2$ 260.0]; LC/MS retention time (Method E): $t_R$=1.92 min.

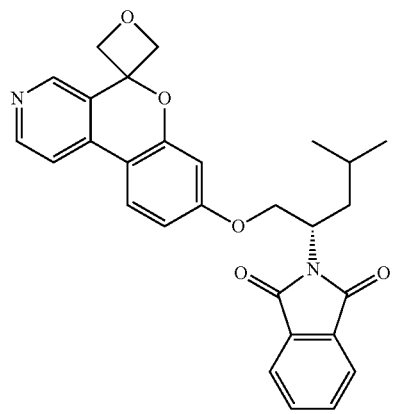 [SMILES: CC(C)C[C@@H](COc1ccc2c(c1)OC1(COC1)c1cnccc1-2)N1C(=O)c2ccccc2C1=O]

Part D. (S)-2-(4-methyl-1-(spiro[chromeno[3,4-e]pyridine-5,3'-oxetan]-8-yloxy)pentan-2-yl)isoindoline-1,3-dione Prepared as described in Example 5, Part E using 8-chlorospiro[chromeno[3,4-c]pyridine-5,3'-oxetane] to afford 2-(4-methyl-1-(spiro[chromeno[3,4-c]pyridine-5,3'-oxetan]-8-yloxy)pentan-2-yl)isoindoline-1,3-dione (35 mg, 0.074 mmol, 64% yield) as a light brown solid. LCMS (ESI) m/e 471.2 [(M+H)$^+$, calcd for C$_{28}$H$_{27}$N$_2$O$_5$ 471.2]; LC/MS retention time (Method E): t$_R$=2.14 min.

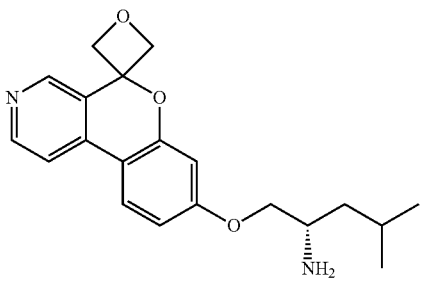 [SMILES: CC(C)C[C@H](N)COc1ccc2c(c1)OC1(COC1)c1cnccc1-2]

Part E. (S)-4-methyl-1-(spirokhromeno[3,4-c]pyridine-5,3'-oxetan]-8-yloxy)pentan-2-amine Prepared as described Example 5, Part F using (S)-2-(4-methyl-1-(spiro[chromeno[3,4-c]pyridine-5,3'-oxetan]-8-yloxy)pentan-2-yl)isoindoline-1,3-dione to afford (S)-4-methyl-1-(spiro[chromeno[3,4-c]pyridine-5,3'-oxetan]-8-yloxy)pentan-2-amine (13 mg, 0.038 mmol, 51% yield) as a pale brown solid. $^1$H NMR (400 MHz, MeOD) δ 8.87 (s, 1H), 8.56 (d, J=5.2 Hz, 1H), 7.85 (d, J=8.4 Hz, 1H), 7.76 (d, J=4.8 Hz, 1H), 6.82-6.78 (m, 2H), 5.04 (d, J=8 Hz, 2H), 4.93 (d, J=8 Hz, 2H), 4.05 (m, 1H), 3.87 (m, 1H), 3.32 (m, 1H), 1.83 (m, 1H), 1.43 (m, 2H), 1.0 (m, 6H); LCMS (ESI) m/e 341.2 [(M+H)$^+$, calcd for C$_{20}$H$_{25}$N$_2$O$_3$ 341.2]; LC/MS retention time (Method E): t$_R$=1.71 min; HPLC retention time (method A): t$_R$=6.93 min; HPLC retention time (method B): t$_R$=8.53 min.

Example 20

(8-(±)-2-amino-4-methylpentyl)oxy)-5-(chloromethyl)-5H-chromeno[3,4-d]pyridin-5-yl)methanol

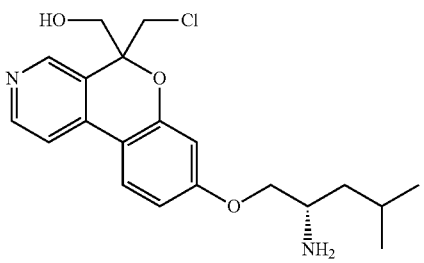 [SMILES: CC(C)C[C@H](N)COc1ccc2c(c1)OC(CO)(CCl)c1cnccc1-2]

To a solution of ((S)-tert-butyl (4-methyl-1-(spiro[chromeno[3,4-c]pyridine-5,3'-oxetan]-8-yloxy)pentan-2-yl)carbamate (10 mg, 0.023 mmol) (prepared as described in Example 19, Part D) in dichloromethane (1 mL) cooled to 0° C. was added 1M HCl in diethyl ether (234, 0.023 mmol) dropwise and the solution stirred for 30 min. The reaction was then warmed to room temperature and stirred for 2 h. After completion of reaction, the volatiles were removed under reduced and purified by preparative HPLC to afford product (8-(((S)-2-amino-4-methylpentyl)oxy)-5-(chloromethyl)-5H-chromeno[3,4-c]pyridin-5-yl)methanol (2.08 mg, 5.52 µmol, 24% yield) as a yellow solid. $^1$H NMR (400 MHz, MeOD) δ 8.82 (m, 1H), 8.69 (m, 1H), 8.35 (m, 1H), 8.09 (m, 1H), 6.94 (m, 1H), 6.82 (s, 1H), 4.36-4.20 (m, 6H), 3.73 (m, 1H), 1.82-1.68 (m, 3H), 1.04 (m, 6H); LCMS (ESI) m/e 377.2 [(M+H)$^+$, calcd for C$_{20}$H$_{26}$ClN$_2$O$_3$ 377.2]; LC/MS retention time (Method E): t$_R$=1.71 min; HPLC retention time (method A): t$_R$=8.12 min; HPLC retention time (method B): t$_R$=9.87 min.

Example 21

(2S)-1-(9-bromo-5-methyl-5H-chromeno[3,4-c]pyridin-8-yloxy)-4-methylpentan-2-amine

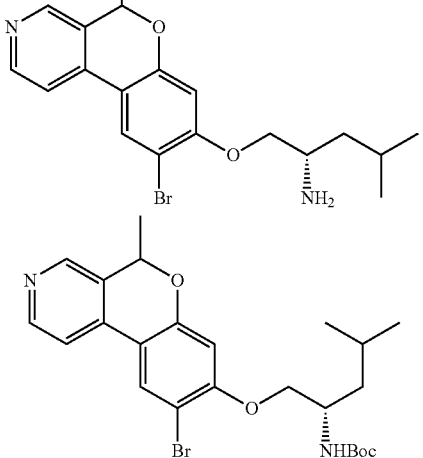

Part A. tert-butyl (2S)-1-(9-bromo-5-methyl-5H-chromeno[3,4-d]pyridin-8-yloxy)-4-methylpentan-2-ylcarbamate Prepared as described in Example 14, Part B using tert-butyl (2S)-4-methyl-1-(5-methyl-5H-chromeno[3,4-c]pyridin-8-yloxy)pentan-2-ylcarbamate (prepared as described in Example 6) to afford tert-butyl (2S)-1-(9-bromo-5-methyl-5H-chromeno[3,4-c]pyridin-8-yloxy)-4-methylpentan-2-yl-carbamate (120 mg, 0.24 mmol, quantitative) LCMS (ESI) m/e 491.2 [(M+H)$^+$, calcd for C$_{24}$H$_{32}$BrN$_2$O$_4$ 491.1] LC/MS retention time (method C): t$_R$=2.44 min.

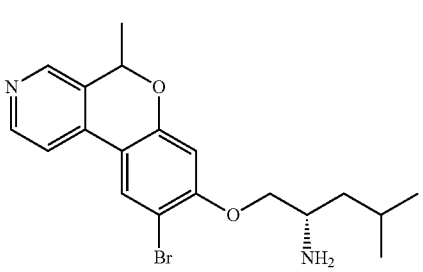 [SMILES: CC(C)C[C@H](N)COc1cc2c(cc1Br)-c1ccncc1C(C)O2]

Part B. (2S)-1-(9-bromo-5-methyl-5H-chromeno[3,4-c]pyridin-8-yloxy)-4-methylpentan-2-amine Prepared as described in Example 8, Part D using tert-butyl 425)-14(9-bromo-5-methyl-5H-chromeno[3,4-c]pyridin-8- yl)oxy)-4-methylpentan-2-yl)carbamate (20 mg, 0.041 mmol) to afford (2S)-1-((9-bromo-5-methyl-5H-chromeno[3,4-c]pyridin-8-yl)oxy)-4-methylpentan-2-amine (7 mg, 0.018 mmol, 44% yield) as a yellow solid. $^1$H NMR (400 MHz, MeOD) δ 8.69 (bs, 2H), 8.39 (s, 1H), 8.31 (bs, 1H), 6.92 (s, 1H), 5.63 (d, J=5.6 Hz, 1H), 4.42 (m, 1H), 4.28 (m, 1H), 3.77 (bs, 1H), 1.83-1.70 (m, 6H), 1.04 (m, 6H). LCMS (ESI) m/e 391.0 [(M+H)$^+$, calcd for $C_{19}H_{24}BrN_2O_2$ 391.1] LC/MS retention time (method C): $t_R$=1.64 min. HPLC retention time (method A): $t_R$=8.36 min and 8.44 min (Dia mixture); HPLC retention time (method B): $t_R$=5.23 min.

Example 22

8-((S)-2-amino-4-methylpentyloxy)-5-methyl-5H-chromeno[3,4-d]pyridine-9-carbonitrile

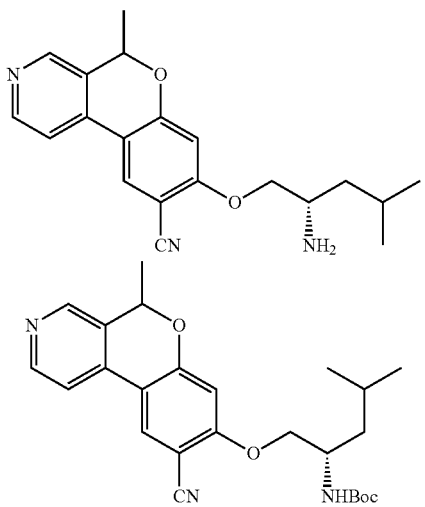

Part A. tert-butyl (2S)-1-(9-cyano-5-methyl-5H-chromeno[3,4-c]pyridin-8-yloxy)-4-methylpentan-2-ylcarbamate To a mixture of tert-butyl ((2S)-1-((9-bromo-5-methyl-5H-chromeno[3,4-c]pyridin-8-yl)oxy)-4-methylpentan-2-yl)carbamate (100 mg, 0.203 mmol) (prepared as described in Example 21, Part A) and L-proline (23.43 mg, 0.203 mmol) in DMF (2 mL) was added copper(I) cyanide (36.5 mg, 0.407 mmol). Argon gas was bubbled through the stirred suspension for 5 min. The reaction mixture was stirred under argon atmosphere at 120° C. for 12 h. The mixture was then cooled to room temperature and diluted with ethyl acetate (10 mL) and filtered through celite. The filtrate was washed with water (10 mL) and brine (10 mL). The combined organic extracts were dried over sodium sulfate and concentrated under reduced pressure to afford crude material which was purified via silica gel chromatography (pet ether: ethyl acetate mobile phase) to afford tert-butyl ((2S)-1-((9-cyano-5-methyl-5H-chromeno[3,4-c]pyridin-8-yl)oxy)-4-methylpentan-2-yl)carbamate (15 mg, 0.034 mmol, 17% yield). LCMS (ESI) m/e 438.2 [(M+H)$^+$, calcd for $C_{25}H_{32}N_3O_4$ 438.2] LC/MS retention time (method D): $t_R$=1.81 min.

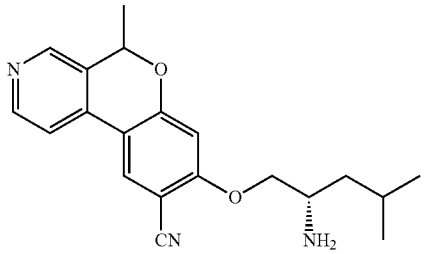 [SMILES: CC(C)C[C@H](N)COc1cc2c(cc1C#N)-c1ccncc1C(C)O2]

Part B. 8-((S)-2-amino-4-methylpentyloxy)-5-methyl-5H-chromeno[3,4-d]pyridine-9-carbonitrile To a solution of tert-butyl ((2S)-1-((9-cyano-5-methyl-5H-chromeno[3,4-c]pyridin-8-yl)oxy)-4-methylpentan-2-yl)carbamate (15 mg, 0.034 mmol) in dichloromethane (2 mL) cooled to 0° C. was added HCl, 4M in dioxane (1.0 mL, 4.00 mmol) slowly over a period of 1 min. The reaction mixture was stirred at 0° C. for 5 min and then warmed to room temperature and allowed to stir for 2 h. The solvents were removed under reduced pressure and the crude material was washed with 5% methanol in ethyl acetate to afford 8-(((S)-2-amino-4-methylpentyl)oxy)-5-methyl-5H-chromeno[3,4-c]pyridine-9-carbonitrile (9 mg, 0.025 mmol, 73% yield) as a yellow solid. $^1$H NMR (400 MHz, MeOD) δ 8.74 (bs, 2H), 8.58 (s, 1H), 8.34 (d, J=6 Hz, 1H), 7.01 (s, 1H), 5.74 (t, J=6.4 Hz, 1H), 4.48 (m, 1H), 4.33 (m, 1H), 3.78 (m, 1H), 1.82-1.68 (m, 6H), 1.06 (m, 6H). LCMS (ESI) m/e 338.2 [(M+H)$^+$, calcd for $C_{20}H_{24}N_3O_2$ 338.2] LC/MS retention time (method D): $t_R$=1.17 min. HPLC retention time (method A): $t_R$=7.97 min and 8.03 min (diastereomeric mixture); HPLC retention time (method B): $t_R$=8.77 min (peaks overlapped).

Example 23

(S)-8-(2-amino-4-methylpentyloxy)-5H-chromeno[3,4-c]pyridine-9-carbonitrile

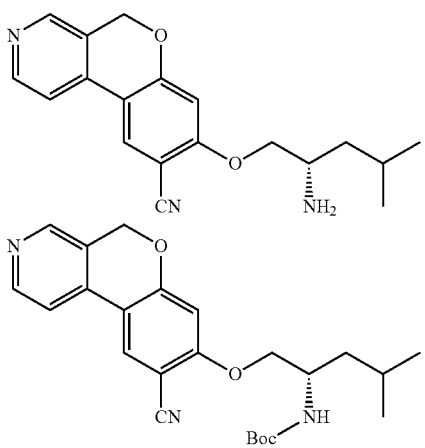

Part A. (S)-tert-butyl 1-(9-cyano-5H-chromeno[3,4-c]pyridin-8-yloxy)-4-methylpentan-2-ylcarbamate Prepared as described in Example 22, Part A using (S)-tert-butyl 1-(9-bromo-5H-chromeno[3,4-c]pyridin-8-yloxy)-4- methylpentan-2-ylcarbamate (0.029 g, 0.061 mmol) to afford (S)-tert-butyl (1-((9-cyano-5H-chromeno[3,4-c]pyridin-8-yl)oxy)-4-methylpentan-2-yl)carbamate (8 mg, 0.019 mmol, 11% yield) as a light brown solid. LCMS (ESI) m/e 424.2 [(M+H)]¹, calcd for $C_{24}H_{30}N_3O_4$ 424.2] LC/MS retention time (method E): $t_R$=2.11 min.

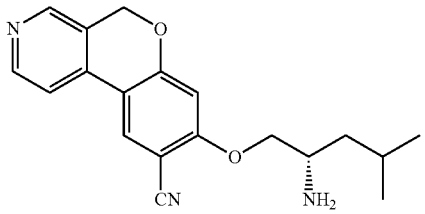

Part B. (S)-8-(2-amino-4-methylpentyl)oxy)-5H-chromeno[3,4-c]pyridine-9-carbonitrile Prepared as described in Example 8, Part D using tert-butyl (1-((9-cyano-5H-chromeno[3,4-c]pyridin-8-yl)oxy)-4-methylpentan-2-yl)carbamate (0.008 g, 0.019 mmol) to afford 8-((2-amino-4-methylpentyl)oxy)-5H-chromeno[3,4-c]pyridine-9-carbonitrile (3.19 mg, 9.86 μmol, 52% yield) as a yellow oil. ¹H NMR (400 MHz, MeOD) δ 8.66 (bs, 1H), 8.45 (s, 1H), 8.08 (bs, 1H), 6.95 (s, 1H), 5.43 (s, 2H), 4.48 (m, 1H), 4.24 (m, 1H), 3.86 (m, 1H), 3.69 (m, 1H), 1.92-1.74 (m, 3H), 1.05 (m, 6H); LCMS (ESI) m/e 324.2 [(M+H)⁺, calcd for $C_{19}H_{22}N_3O_2$ 324.2]; LC/MS retention time (Method E): $t_R$=1.79 min; HPLC retention time (method A): $t_R$=7.05 min; HPLC retention time (method B): $t_R$=7.87 min.

Example 24

(2S)-1-cyclopentyl-3-(5-methyl-5H-chromeno[3,4-c]pyridin-8-yloxy)propan-2-amine

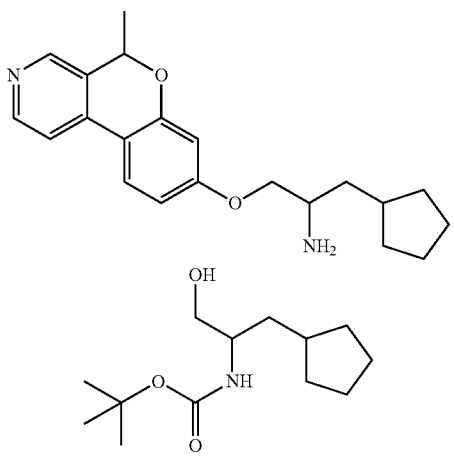

Part A. tert-butyl 1-cyclopentyl-3-hydroxypropan-2-ylcarbamate

To a solution of 2-((tert-butoxycarbonyl)amino)-3-cyclopentylpropanoic acid (730 mg, 2.84 mmol) in THF (7.5 mL) cooled to −10° C. was added N-methylmorpholine (0.312 mL, 2.84 mmol) followed by isobutyl chloroformate (0.373 mL, 2.84 mmol). The reaction mixture was then stirred for 5 min. The solid obtained was removed by filtration and washed with THF (5 mL). The filtrate was cooled to −10° C. and treated with NaBH₄ (161 mg, 4.26 mmol) in water (5 mL) dropwise. The reaction mixture was stirred at −10° C. for 10 min and allowed to warm to room temperature and stirred for another 30 min. The reaction mixture was then quenched with cold water (5 mL). The aqueous layer extracted with ethyl acetate (3×20 mL). The combined organic layers were washed with brine (20 mL), dried over sodium sulfate and concentrated under reduced pressure to afford a residue which was purified by column chromatography (pet ether: ethyl acetate) to afford tert-butyl 1-cyclopentyl-3-hydroxypropan-2-ylcarbamate (500 mg, 2.05 mmol, 72% yield). ¹H NMR (400 MHz, DMSO-$d_6$) δ 6.38 (m, 1H), 4.51 (m, 1H), 3.85-3.65 (m, 1H), 3.42 (m, 1H), 3.25 (m, 1H), 3.8 (m, 1H), 2.75 (m, 1H), 1.85-1.65 (m, 4H), 1.6-1.25 (m, 12H), 1.15 (m, 2H).

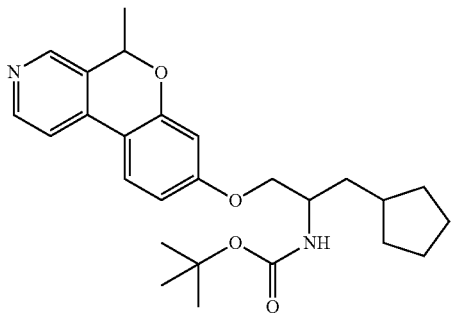 [SMILES: CC1Oc2cc(OCC(CC3CCCC3)NC(=O)OC(C)(C)C)ccc2-c2ccncc21]

Part B. tert-butyl (2S)-1-cyclopentyl-3-(5-methyl-5H-chromeno[3,4-e]pyridin-8-yloxy)propan-2-ylcarbamate Prepared as described in Example 8, Part C using 8-chloro-5-methyl-5H-chromeno[3,4-c]pyridine (100 mg, 0.432 mmol) to afford crude residue which was purified via silica gel chromatography (pet ether and ethyl acetate as a mobile phase) to yield tert-butyl (1-cyclopentyl-3-((5-methyl-5H-chromeno[3,4-c]pyridin-8-yl)oxy)propan-2-yl)carbamate (30 mg, 0.062 mmol, 14% yield) as an off-white solid. LCMS (ESI) m/e 439.3 [(M+H)⁺, calcd for $C_{26}H_{35}N_2O_4$ 439.3] LC/MS retention time (method C): $t_R$=2.44 min.

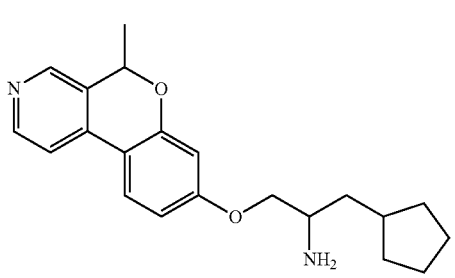 [SMILES: CC1Oc2cc(OCC(N)CC3CCCC3)ccc2-c2ccncc21]

Part C. (2S)-1-cyclopentyl-3-(5-methyl-5H-chromeno[3,4-c]pyridin-8-yloxy)propan-2-amine Prepared as described in Example 8, Part D using tert-butyl (1-cyclopentyl-3-((5-methyl-5H-chromeno[3,4-c]pyridin-8- yl)oxy)propan-2-yl)carbamate (30 mg, 0.068 mmol) to afford 1-cyclopentyl-3-((5-methyl-5H-chromeno[3,4-c]pyridin-8-yl)oxy)propan-2-amine (14 mg, 0.040 mmol, 59% yield) as a yellow oil. $^1$H NMR (400 MHz, MeOD) δ 8.45 (s, 1H), 8.35 (s, 1H), 7.95 (m, 1H), 7.8 (d, J=2.4 Hz, 1H), 6.75 (m, 1H), 6.6 (s, 1H), 5.42 (m, 1H), 4.05-4.15 (m, 1H), 3.9-3.85 (m, 1H), 3.3-3.1 (m, 1H), 2.0 (m, 1H), 1.95 (m, 2H), 1.9-1.4 (m, 9H), 1.3-1.02 (m, 2H); LCMS (ESI) m/e 339.2 [(M+H)$^+$, calcd for $C_{21}H_{27}N_2O_2$ 339.2]; LC/MS retention time (Method C): $t_R$=1.53 min; HPLC retention time (Method: Eclipse XDB C18 (4.6×150 mm, 3.5 um), Mobile phase: A=20 mM $NH_4OAc$ in water; Mobile phase B=acetonitrile; 0-12 min, 0% B→10% B; 12-15 min, 10% B→100% B; 15-17 min, 100% B; flow rate=1 mL/min; λ=254 nm and 220 nm; run time=17 min): $t_R$=8.22 min; HPLC retention time (method A): $t_R$=9.34 min.

Example 25

(S)-8-(2-amino-4-methylpentyloxy)-9-bromo-5H-chromeno[3,4-d]pyridin-5-one

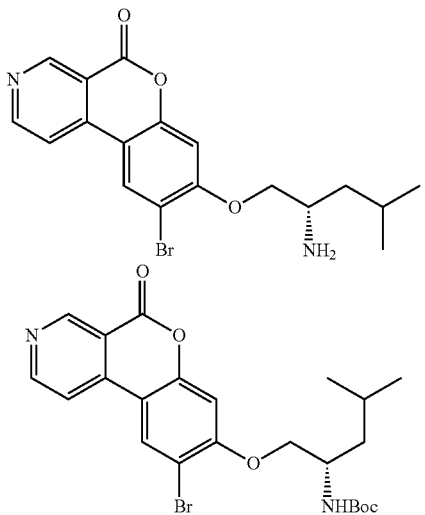

Part A. (S)-tert-butyl 1-(9-bromo-5-oxo-5H-chromeno[3,4-c]pyridin-8-yloxy)-4-methylpentan-2-ylcarbamate To a stirred solution of (S)-tert-butyl (4-methyl-1-((5-oxo-5H-chromeno[3,4-c]pyridin-8-yl)oxy)pentan-2-yl)carbamate (0.100 g, 0.242 mmol) (prepared as described in Example 11, Part E) in anhydrous acetonitrile (2 mL) was added NBS (0.043 g, 0.242 mmol) and the mixture heated to 80° C. for 12 h. After completion of reaction, water (10 mL) was added and extracted with ethyl acetate (2×20 mL). The combined organic extracts were dried over sodium sulfate and concentrated under reduced pressure to afford crude compound which was purified by preparative TLC to afford (S)-tert-butyl (1-((9-bromo-5-oxo-5H-chromeno[3,4-c]pyridin-8-yl)oxy)-4-methylpentan-2-yl)carbamate (80 mg, 0.163 mmol, 67% yield) as a pale yellow solid. LCMS (ESI) m/e 491.2 [(M+H)$^+$, calcd for $C_{23}H_{28}BrN_2O_5$ 491.1] LC/MS retention time (method F): $t_R$=1.12 min.

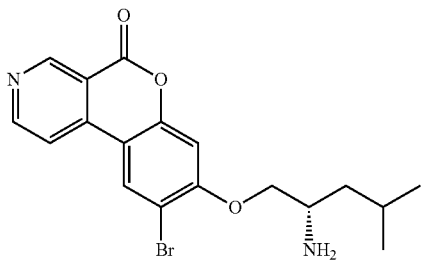 [SMILES: CC(C)C[C@H](N)COc1cc2oc(=O)c3cnccc3c2cc1Br]

Part B. (S)-8-(2-amino-4-methylpentyloxy)-9-bromo-5H-chromeno[3,4-d]pyridin-5-one Prepared as described in Example 8, Part D using (S)-tert-butyl (1-((9-bromo-5-oxo-5H-chromeno[3,4-c]pyridin-8-yl)oxy)-4-methylpentan-2-yl)carbamate to afford (S)-8-((2-amino-4-methylpentyl)oxy)-9-bromo-5H-chromeno[3,4-c]pyridin-5-one (6 mg, 0.015 mmol, 1% yield) as a white solid. $^1$H NMR (400 MHz, MeOD) δ 9.38 (s, 1H), 8.89 (d, J=5.6 Hz, 1H), 8.57 (s, 1H), 8.19 (d, J=5.6 Hz, 1H), 7.18 (s, 1H), 4.24 (m, 1H), 4.06 (m, 1H), 3.43 (m, 1H), 1.84 (m, 1H), 1.63-1.46 (m, 2H), 1.02 (m, 6H). LCMS (ESI) m/e 391.0 [(M+H)$^+$, calcd for $C_{18}H_{20}BrN_2O_3$ 391.1]; LC/MS retention time (Method C): $t_R$=1.53 min; HPLC retention time (method A): $t_R$=11.15 min; HPLC retention time (method B): $t_R$=12.19 min.

Example 26

4-fluoro-4-methyl-1-(5-methyl-5H-chromeno[3,4-c]pyridin-8-yloxy)pentan-2-amine

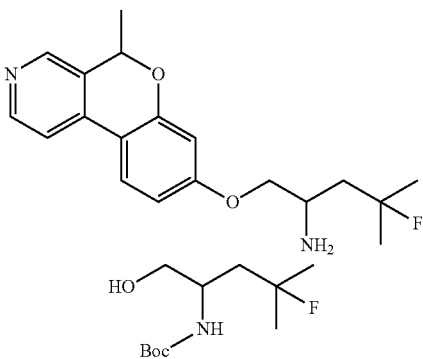

Part A. tert-butyl 4-fluoro-1-hydroxy-4-methylpentan-2-ylcarbamate

Prepared as described in Example 24, Part A using 2-(tert-butoxycarbonylamino)-4-fluoro-4-methylpentanoic acid (300 mg, 1.203 mmol) to afford tert-butyl 4-fluoro-1-hydroxy-4-methylpentan-2-ylcarbamate (170 mg, 0.73 mmol, 60% yield) as a pale yellow oil. $^1$H NMR (400 MHz, CDCl$_3$) δ 4.91 (bs, 1H), 3.85 (m, 1H), 3.65 (m, 2H), 2.46 (bs, 1H), 1.81 (m, 2H), 1.45 (m, 12H), 1.38 (m, 3H).

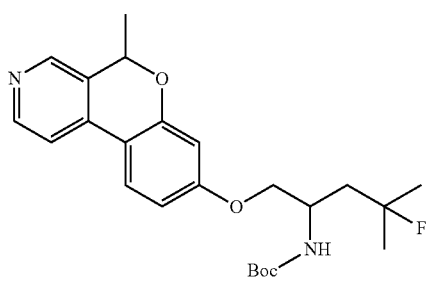 [SMILES: CC1Oc2cc(OCC(CC(C)(C)F)NC(=O)OC(C)(C)C)ccc2-c2ccncc21]

Part B. tert-butyl-4-fluoro-4-methyl-1-(5-methyl-5H-chromeno[3,4-c]pyridin-8-yloxy)pentan-2-ylcarbamate Prepared as described in Example 8, Part C using tert-butyl (4-fluoro-4-methyl-1-((5-methyl-5H-chromeno[3,4-c]pyridin-8-yl)oxy)pentan-2-yl)carbamate (100 mg, 0.232 mmol) to afford tert-butyl-4-fluoro-4-methyl-1-(5-methyl-5H-chromeno[3,4-c]pyridin-8-yloxy)pentan-2-ylcarbamate (100 mg, 0.204 mmol, 47% yield) as a light brown solid. LCMS (ESI) m/e 431.2 [(M+H)$^+$, calcd for $C_{19}H_{24}FN_2O_2$ 431.2] LC/MS retention time (method D): $t_R$=1.02 min.

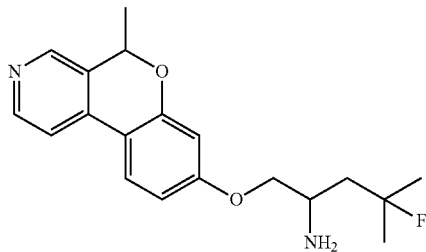 [SMILES: CC1Oc2cc(OCC(N)CC(C)(C)F)ccc2-c2ccncc21]

Part C. 4-fluoro-4-methyl-1-(5-methyl-5H-chromeno[3,4-c]pyridin-8-yloxy)pentan-2-amine Prepared as described in Example 8, Part D using 8-chloro-5-methyl-5H-chromeno[3,4-c]pyridine (0.100 g, 0.432 mmol) and tert-butyl (4-fluoro-1-hydroxy-4-methylpentan-2-yl)carbamate (0.168 g, 0.712 mmol) to afford 4-fluoro-4-methyl-1-(5-methyl-5H-chromeno[3,4-c]pyridin-8-yloxy)pentan-2-amine (80 mg, 0.23 mmol, 99% yield) as a yellow oil. $^1$H NMR (400 MHz, MeOD) δ 8.66 (d, J=6.4 Hz, 1H), 8.64 (s, 1H), 8.24 (d, J=6.4 Hz, 1H), 8.08 (d, J=8.8 Hz, 1H), 6.94 (dd, J=2.4 Hz, 8.8 Hz, 1H), 6.78 (d, J=2.8 Hz, 1H), 5.57 (q, J=6.4 Hz, 1H), 4.38 (dd, J=6.4 Hz, J=10.8 Hz, 1H), 4.22 (dd, J=6.4 Hz, 10.8 Hz, 1H), 3.99 (m, 1H), 2.16 (m, 2H), 1.75 (d, J=6.8 Hz, 3H), 1.55 (s, 3H), 1.50 (s, 3H); LCMS (ESI) m/e 331.2 [(M+H)$^1$, calcd for $C_{19}H_{24}FN_2O_2$ 331.2] LC/MS retention time (method D): $t_R$=0.97 min; HPLC retention time (method B): $t_R$=8.04 min.

Example 27

(2S)-1-((9-chloro-5-(trifluoromethyl)-5H-chromeno[3,4-e]pyridin-8-yl)oxy)-4-methylpentan-2-amine

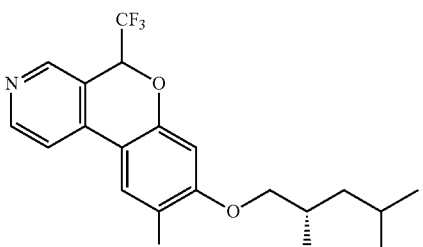

Part A. 1-(4-(4-chloro-2-fluorophenyl)pyridin-3-yl)-2,2,2-trifluoroethanol

A stirred solution of 4-(4-chloro-2-fluorophenyl)nicotinaldehyde (1.8 g, 7.64 mmol) (prepared as described in Example 5, Part B) and TMS-CF$_3$ (0.521 mL, 3.52 mmol) in dichloromethane (20 mL) was stirred at 0° C. for 20 min. TBAF (1.0 M in THF) (0.4 mL, 1.528 mmol) was added dropwise slowly and the solution stirred for 90 min. Water was added and the solution extracted with dichloromethane (2×25 mL). The combined organic layers were washed with brine, dried over sodium sulphate, concentrated and purified by Prep. TLC using 25% ethyl acetate in hexane to give 1-(4-(4-chloro-2-fluorophenyl)pyridin-3-yl)-2,2,2-trifluoroethanol (1 g, 2.64 mmol, 35% yield) as a yellow oil. LCMS (ESI) m/e 306.0 [(M+H)$^+$, calcd for $C_{13}H_9ClF_4NO$ 306.02]; LC/MS retention time (Method C): $t_R$=2.05 min.

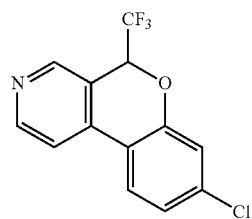 [SMILES: FC(F)(F)C1Oc2cc(Cl)ccc2-c2ccncc21]

Part B. 8-chloro-5-(trifluoromethyl)-5H-chromeno[3,4-e]pyridine

Prepared as described in Example 5, Part D using 1-(4-(4-chloro-2-fluorophenyl)pyridin-3-yl)-2,2,2-trifluoroethanol to afford 8-chloro-5-(trifluoromethyl)-5H-chromeno[3,4-c]pyridine (800 mg, 2.63 mmol, 80% yield) as a yellow solid. LCMS (ESI) m/e 286.0 [(M+H)$^+$, calcd for $C_{13}H_8ClF_3NO$ 286.01]; LC/MS retention time (Method C): $t_R$=2.11 min.

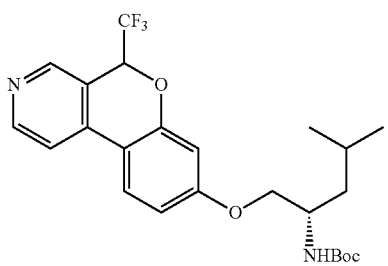 [SMILES: CC(C)C[C@@H](COc1ccc2c(c1)OC(C(F)(F)F)c1cnccc1-2)NC(=O)OC(C)(C)C]

Part C. tert-butyl ((2S)-4-methyl-1-((5-(trifluoromethyl)-5H-chromeno[3,4-c]pyridin-8-yl)oxy)pentan-2-yl)carbamate Prepared as described in Example 8, Part C using (S)-tert-butyl (1-hydroxy-4-methylpentan-2-yl)carbamate and 8-chloro-5-(trifluoromethyl)-5H-chromeno[3,4-c]pyridine to afford tert-butyl ((2S)-4-methyl-1-((5-(trifluoromethyl)-5H-chromeno[3,4-c]pyridin-8-yl)oxy)pentan-2-yl)carbamate (0.28 g, 0.516 mmol, 49% yield) as a yellow solid. LCMS (ESI) m/e 467.2 [(M+H)$^+$, calcd for $C_{24}H_{30}F_3N_2O_4$ 467.2]; LC/MS retention time (Method C): $t_R$=2.19 min.

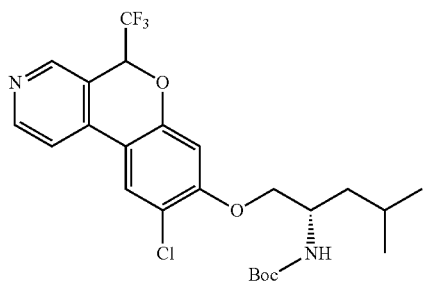 [SMILES: CC(C)C[C@@H](COc1cc2c(cc1Cl)-c1ccncc1C(C(F)(F)F)O2)NC(=O)OC(C)(C)C]

Part D. tert-butyl ((2S)-1-(9-chloro-5-(trifluoromethyl)-5H-chromeno[3,4-c]pyridin-8-yl)oxy)-4-methylpentan-2-yl)carbamate A stirred solution of tert-butyl ((2S)-4-methyl-1-(5-(trifluoromethyl)-5H-chromeno[3,4-c]pyridin-8-yl)oxy)pentan-2-yl)carbamate (50 mg, 0.107 mmol) and NCS (14.31 mg, 0.107 mmol) in acetonitrile (12 mL) was heated to 60° C. under nitrogen atmosphere for 12 h. The solvent was removed under reduced pressure. The residue was partitioned between water (15 mL) and DCM (15 mL). The organic layer was separated, dried over sodium sulphate and concentrated under reduced pressure to yield tert-butyl ((2S)-1-((9-chloro-5-(trifluoromethyl)-5H-chromeno[3,4-c]pyridin-8-yl)oxy)-4-methylpentan-2-yl)carbamate (51 mg, 0.092 mmol, 86% yield) as a yellow solid. LCMS (ESI) m/e 501.2 [(M+H)$^+$, calcd for $C_{24}H_{29}ClF_3N_2O_4$ 501.2]; LC/MS retention time (Method D): $t_R$=2.02 min.

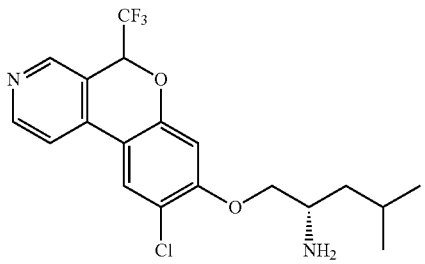 [SMILES: CC(C)C[C@H](N)COc1cc2c(cc1Cl)-c1ccncc1C(C(F)(F)F)O2]

Part E. (2S)-1-(9-chloro-5-(trifluoromethyl)-5H-chromeno[3,4-d]pyridin-8-yl)oxy)-4-methylpentan-2-amine To a stirred solution of tert-butyl ((2S)-1-((9-chloro-5-(trifluoromethyl)-5H-chromeno[3,4-c]pyridin-8-yl)oxy)-4-methylpentan-2-yl)carbamate (50 mg, 0.100 mmol) in DCM (10 mL) was added 1M HCl in diethyl ether (0.100 mmol) at room temperature and the solution stirred for 14 h. The solvent was removed under reduced pressure to afford a residue which was purified by preparative HPLC using 0.1% TFA in methanol. The purification afforded (2S)-1-((9-chloro-5-(trifluoromethyl)-5H-chromeno[3,4-c]pyridin-8-yl)oxy)-4-methylpentan-2-amine (10 mg, 0.023 mmol, 23% yield) as a pale yellow solid. $^1$H NMR (400 MHz, DMSO-$d_6$) δ 8.67 (d, J=5.2 Hz, 1H), 8.57 (s, 1H), 8.32 (s, 1H), 7.98 (d, J=5.2 Hz, 1H), 6.97 (s, 1H), 6.45 (m, 1H), 3.9 (m, 1H), 3.87 (m, 1H), 3.09 (m, 1H), 1.83 (m, 1H), 1.33 (m, 2H), 1.31-1.26 (m, 6H); LCMS (ESI) m/e 401.2 [(M+H), calcd for $C_{19}H_{21}ClF_3N_2O_2$ 401.1]; LC/MS retention time (Method C): $t_R$=1.69 min; HPLC retention time (method A): $t_R$=5.80 min, 5.87 min (diastereomeric mixture); HPLC retention time (method B): $t_R$=6.41 min, 6.45 min (diastereomeric mixture).

Example 27a and 27b (S)-1-(((R)-9-chloro-5-(trifluoromethyl)-5H-chromeno[3,4-c]pyridin-8-yl)oxy)-4-methylpentan-2-amine and (S)-1-(((S)-9-chloro-5-(trifluoromethyl)-5H-chromeno[3,4-c]pyridin-8-yl)oxy)-4-methylpentan-2-amine

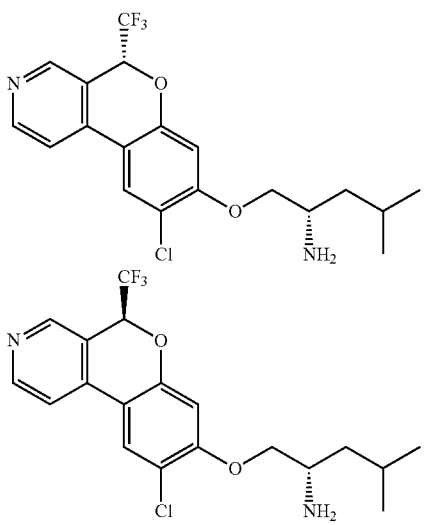

The diastereomers were resolved with the aid of preparative chiral HPLC using 0.5% diethyl amine in methanol to afford 2 separate diastereomers (absolute chemistry of CF3 unknown). Obtained diastereomer 1 (36 mg, 0.082 mmol, 16% yield) as a yellow gummy liquid. $^1$H NMR (400 MHz, CD$_3$OD) δ 8.62 (d, J=5.2 Hz, 1H), 8.52 (s, 1H), 8.02 (s, 1H), 7.84 (d, J=5.2 Hz, 1H), 6.88 (s, 1H), 6.10 (q, J=7.6 Hz, 1H), 4.08 (dd, J=4.4 Hz, J=9.2 Hz, 1H) 3.91 (dd, J=6.8 Hz, J=9.2 Hz, 1H), 3.32 (m, 1H), 1.83 (m, 1H), 1.45 (m, 2H), 0.99 (m, 6H); LCMS (ESI) m/e 401.2 [(M+H)$^+$, calcd for C$_{19}$H$_{21}$ClF$_3$N$_2$O$_2$ 401.1]; LC/MS retention time (Method I): $t_R$=1.87 min; HPLC retention time (method A): $t_R$=5.76 min: HPLC retention time (method B): $t_R$=6.28 min. Chiral SFC (0.5% DEA in methanol-Column Chiralpak AD H (250×4.6) mm-50; $t_R$=1.52 min. Obtained diastereomer 2 (38 mg, 0.089 mmol, 17% yield) as a yellow gum; $^1$H NMR (400 MHz, CD$_3$OD) δ 8.61 (d, J=5.2 Hz, 1H), 8.52 (s, 1H), 8.03 (s, 1H), 7.85 (d, J=5.2 Hz, 1H), 6.88 (s, 1H), 6.10 (q, J=7.6 Hz, 1H), 4.11 (dd, J=4 Hz, J=9.2 Hz, 1H) 3.89 (dd, J=6.8 Hz, J=9.2 Hz, 1H), 3.31 (m, 1H), 1.83 (m, 1H), 1.48 (m, 2H), 0.99 (m, 6H); LCMS (ESI) m/e 401.2 [(M+H)$^+$, calcd for C$_{19}$H$_{21}$ClF$_3$N$_2$O$_2$ 401.1]; LC/MS retention time (Method I): $t_R$=1.86 min; HPLC retention time (method A): $t_R$=5.68 min: HPLC retention time (method B): $t_R$=6.25 min. Chiral SFC (0.5% DEA in methanol-Column Chiralpak AD H (250×4.6)mm-50; $t_R$=3.93 min.

Example 28

(2S)-1-((9-bromo-5-(trifluoromethyl)-5H-chromeno [3,4-c]pyridin-8-yl)oxy)-4-methylpentan-2-amine

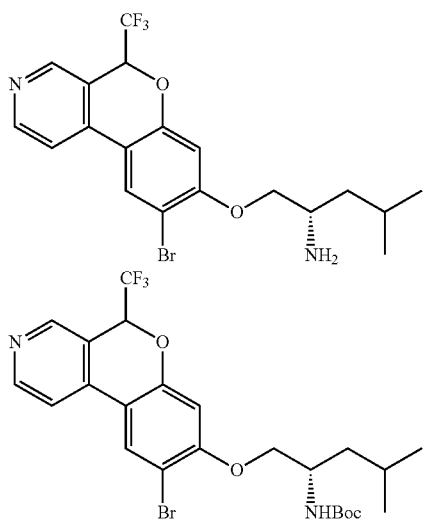

Part A. tert-butyl ((2S)-1-(9-bromo-5-(trifluoromethyl)-5H-chromeno[3,4-e]pyridin-8-yl)oxy)-4-methylpentan-2-yl)carbamate Prepared as described in Example 14, Part B using tert-butyl 425)-4-methyl-1-(5-(trifluoromethyl)-5H-chromeno [3,4-c]pyridin-8-yl)oxy)pentan-2-yl)carbamate (Example 27, Part C) to afford tert-butyl ((2S)-1-((9-bromo-5-(trifluoromethyl)-5H-chromeno[3,4-c]pyridin-8-yl)oxy)-4-methylpentan-2-yl)carbamate (0.42 g, 0.579 mmol, 75% yield) as a yellow solid. LCMS (ESI) m/e 545.2 [(M+H)$^+$, calcd for C$_{24}$H$_{29}$BrF$_3$N$_2$O$_4$ 545.1]; LC/MS retention time (Method F) $t_R$=1.1 min.

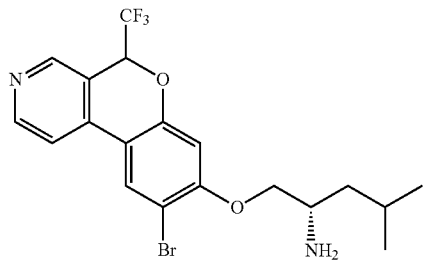 [SMILES: CC(C)C[C@H](N)COc1cc2c(cc1Br)-c1ccncc1C(C(F)(F)F)O2]

Part B. (2S)-1-(9-bromo-5-(trifluoromethyl)-5H-chromeno[3,4-e]pyridin-8-yl)oxy)-4-methylpentan-2-amine To a stirred solution of tert-butyl ((2S)-1-((9-bromo-5-(trifluoromethyl)-5H-chromeno[3,4-c]pyridin-8-yl)oxy)-4-methylpentan-2-yl)carbamate (50 mg, 0.092 mmol) in dichloromethane (10 mL) at room temperature was added TFA (0.035 mL, 0.458 mmol) and stirred overnight. The solvent was removed under reduced pressure to afford a residue which was purified by preparative HPLC using 0.1% TFA in MeOH. The purification afforded (2S)-1-((9-bromo-5-(trifluoromethyl)-5H-chromeno[3,4-c]pyridin-8-yl)oxy)-4-methylpentan-2-amine (15 mg, 0.033 mmol, 36% yield) as a yellow solid. $^1$H NMR (400 MHz, MeOD) δ 8.64 (m, 1H), 8.54 (m, 1H), 8.23 (m, 1H), 7.88 (s, 1H), 6.91 (s, 1H), 6.10 (m, 1H), 4.3 (m, 1H), 4.12 (m, 1H), 3.52 (m, 1H), 1.85 (m, 1H), 1.72-1.69 (m, 1H), 1.61-1.56 (m, 1H), 1.05 (m, 6H). LCMS (ESI) m/e 445.2 [(M+H)$^+$, calcd for C$_{19}$H$_{21}$BrF$_3$N$_2$O$_2$ 445.1]; LC/MS retention time (Method C): $t_R$=1.74 min; HPLC retention time (method A): $t_R$=5.66 min, 5.75 min (diastereomeric mixture); HPLC retention time (method B): $t_R$=6.27 min, 6.34 min (diastereomeric mixture).

Example 29

8-(((S)-2-amino-4-methylpentyl)oxy)-5-methyl-5H-chromeno[3,4-c]pyridin-2-amine

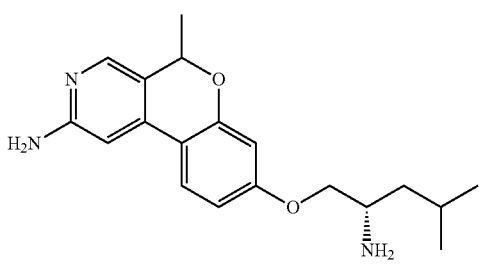

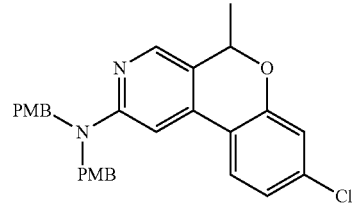

Part A. 8-chloro-N,N-bis(4-methoxybenzyl)-5-methyl-5H-chromeno[3,4-c]pyridin-2-amine To a stirred solution of N-(8-chloro-5-methyl-5H-chromeno[3,4-c]pyridin-2-yl)acetamide (250 mg, 0.866 mmol) in DMF (25 mL) was added NaH (62.3 mg, 2.60 mmol) at room temperature and stirred for 10 min. 4-Methoxybenzyl chloride (0.236 mL, 1.732 mmol) was added dropwise and stirred at room temperature overnight. The reaction was quenched with ice and extracted with ethyl acetate (25 mL). The organic layer was separated, washed with water (25 mL), brine (25 mL), dried over sodium sulphate and concentrated under reduced pressure to afford 8-chloro-N,N-bis(4-methoxybenzyl)-5-methyl-5H-chromeno[3,4-c]pyridin-2-amine (200 mg, 0.20 mmol, 24% yield) as a yellow oil. This was taken to the next step without purification. LCMS (ESI) m/e 487.2 [(M+H)$^+$, calcd for $C_{29}H_{28}ClN_2O_3$ 487.2]; LC/MS retention time (Method C): $t_R$=2.52 min.

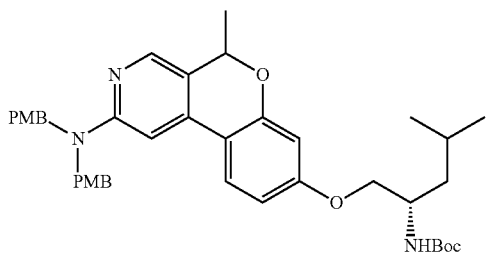

Part B. tert-butyl (2S)-1-(2-(bis(4-methoxybenzyl)amino)-5-methyl-5H-chromeno[3,4-c]pyridin-8-yloxy)-4-methylpentan-2-ylcarbamate Prepared as described in Example 8, Part C using 8-chloro-N,N-bis(4-methoxybenzyl)-5-methyl-5H-chromeno[3,4-c]pyridin-2-amine to afford tert-butyl (2S)-1-(2-(bis(4-methoxybenzyl)amino)-5-methyl-5H-chromeno[3,4-c]pyridin-8-yloxy)-4-methylpentan-2-ylcarbamate (110 mg, 0.070 mmol, 17% yield) as a brown oil. LCMS (ESI) m/e 668.6 [(M+H)$^+$, calcd for $C_{40}H_{50}N_3O_6$ 668.4]; LC/MS retention time (Method F): $t_R$=1.49 min.

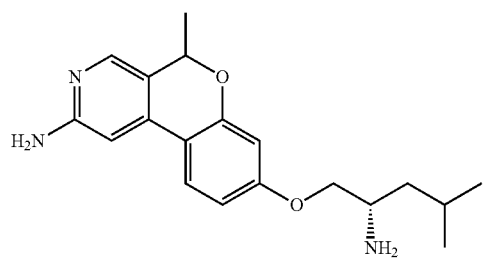 [SMILES: CC(C)C[C@H](N)COc1ccc2c(c1)OC(C)c1cnc(N)cc1-2]

Part C. 8-(((S)-2-amino-4-methylpentyl)oxy)-5-methyl-5H-chromeno[3,4-c]pyridin-2-amine To a stirred solution of tert-butyl ((2S)-1-((2-(bis(4-methoxybenzyl)amino)-5-methyl-5H-chromeno[3,4-c]pyridin-8-yl)oxy)-4-methylpentan-2-yl)carbamate (110 mg, 0.165 mmol) in dichloromethane (10 mL) was added TFA (0.254 mL, 3.29 mmol) and the reaction was stirred at room temperature overnight. The volatiles were evaporated and the crude material was purified by preparative HPLC (0.1% TFA in MeOH) to afford 8-4(S)-2-amino-4-methylpentyl)oxy)-5-methyl-5H-chromeno[3,4-c]pyridin-2-amine (25 mg, 0.069 mmol, 42% yield) as a yellow solid. $^1$H NMR (400 MHz, MeOD) δ 7.74 (m, 2H), 6.84 (s, 1H), 6.75 (dd, J=2.4 Hz, J=8.4 Hz, 1H), 6.63 (d, J=2.4 Hz, 1H), 5.18 (m, 1H), 4.32 (m, 1H), 4.15 (m, 1H), 3.65 (m, 1H), 1.83 (m, 1H), 1.65 (m, 5H), 1.04 (m, 6H); LCMS (ESI) m/e 328.2 [(M+H)$^+$, calcd for $C_{19}H_{26}N_3O_2$ 328.2]; LC/MS retention time (Method D): $t_R$=1.24 min; HPLC retention time (method A): $t_R$=8.42 min.

Example 30

N-(8-(±)-2-amino-4-methylpentyl)oxy)-5-methyl-5H-chromeno[3,4-c]pyridin-2-yl)acetamide

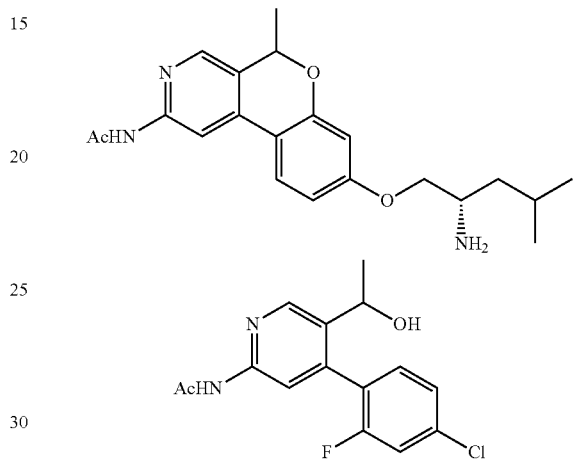

Part A. N-(4-(4-chloro-2-fluorophenyl)-5-(1-hydroxyethyl)pyridin-2-yl)acetamide

Prepared as described in Example 6, Part A using N-(4-(4-chloro-2-fluorophenyl)-5-formylpyridin-2-yl)acetamide (synthesis described in Example 18, Part E) to afford N-(4-(4-chloro-2-fluorophenyl)-5-(1-hydroxyethyl)pyridin-2-yl)acetamide (1.7 g, 4.99 mmol, 91% yield) as a off white solid. LCMS (ESI) m/e 309.2 [(M+H)$^+$, calcd for $C_{15}H_{15}ClFN_2O_2$ 309.1]; LC/MS retention time (Method C): $t_R$=1.54 min.

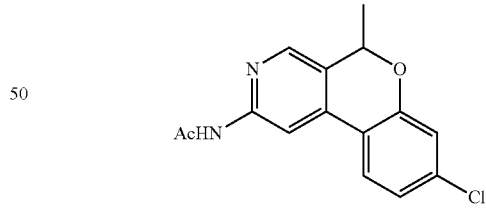

Part B. N-(8-chloro-5-methyl-5H-chromeno[3,4-e]pyridin-2-yl)acetamide

Prepared as described in Example 18, Part G using N-(4-(4-chloro-2-fluorophenyl)-5-(1-hydroxyethyl)pyridin-2-yl)acetamide to afford N-(8-chloro-5-methyl-5H-chromeno[3,4-c]pyridin-2-yl)acetamide (1.5 g, 3.58 mmol, 65% yield) as a yellow solid. LCMS (ESI) m/e 289.0 [(M+H)$^+$, calcd for $C_{15}H_{14}ClN_2O_2$ 289.1]; LC/MS retention time (Method D): $t_R$=1.65 min.

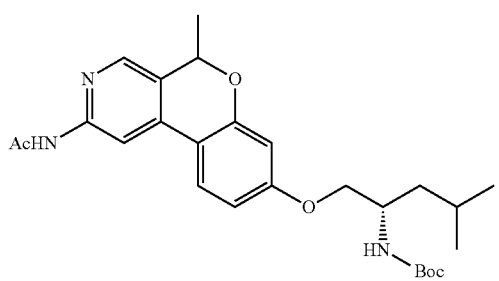 [SMILES: CC(=O)Nc1cc2c(cn1)C(C)Oc1cc(OC[C@H](CC(C)C)NC(=O)OC(C)(C)C)ccc1-2]

Part C. tert-butyl ((2S)-1-(2-acetamido-5-methyl-5H-chromeno[3,4-c]pyridin-8-yl)oxy)-4-methylpentan-2-yl)carbamate Prepared as described in Example 8, Part C using (S)-tert-butyl (1-hydroxy-4-methylpentan-2-yl)carbamate and N-(8-chloro-5-methyl-5H-chromeno[3,4-c]pyridin-2-yl)acetamide to afford tert-butyl ((2S)-1-((2-acetamido-5-methyl-5H-chromeno[3,4-c]pyridin-8-yl)oxy)-4-methylpentan-2-yl)carbamate (290 mg, 0.617 mmol, 33% yield) as a yellow oil. LCMS (ESI) m/e 470.3 [(M+H)$^+$, calcd for $C_{26}H_{36}N_3O_5$ 470.3]; LC/MS retention time (Method F): $t_R$=0.99 min.

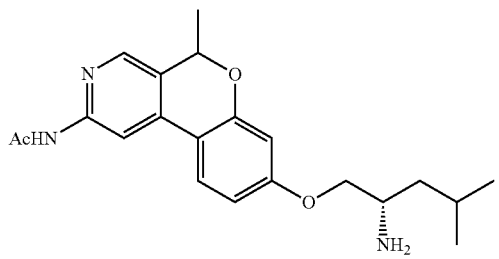 [SMILES: CC(=O)Nc1cc2c(cn1)C(C)Oc1cc(OC[C@@H](N)CC(C)C)ccc1-2]

Part D. N-(8-(±)-2-amino-4-methylpentyl)oxy)-5-methyl-5H-chromeno[3,4-c]pyridin-2-yl)acetamide Prepared as described in Example 29, Part C using tert-butyl ((2S)-1-((2-acetamido-5-methyl-5H-chromeno[3,4-c]pyridin-8-yl)oxy)-4-methylpentan-2-yl)carbamate to afford N-(8-4(S)-2-amino-4-methylpentyl)oxy)-5-methyl-5H-chromeno[3,4-c]pyridin-2-yl)acetamide (8 mg, 0.020 mmol, 15% yield) as a yellow solid. $^1$H NMR (400 MHz, MeOD) δ 8.35 (s, 1H), 8.12 (s, 1H), 7.78 (d, J=8.8 Hz, 1H), 6.78 (m, 1H), 6.64 (d, J=2.4 Hz, 1H), 5.43 (m, 1H), 4.24 (m, 1H), 3.95 (m, 1H), 3.55 (m, 1H), 2.22 (s, 3H), 1.81 (m, 1H), 1.55-1.65 (m, 3H), 1.35 (m, 2H), 1.15 (m, 6H); LCMS (ESI) m/e 370.2 [(M+H)$^+$, calcd for $C_{21}H_{28}N_3O_3$ 370.2]; LC/MS retention time (Method D): $t_R$=1.36 min; HPLC retention time (method A): $t_R$=9.09 min.

Example 31a and 31b (2S)-1-(9-iodo-5-methyl-5H-chromeno[3,4-d]pyridin-8-yloxy)-4-methylpentan-2-amine

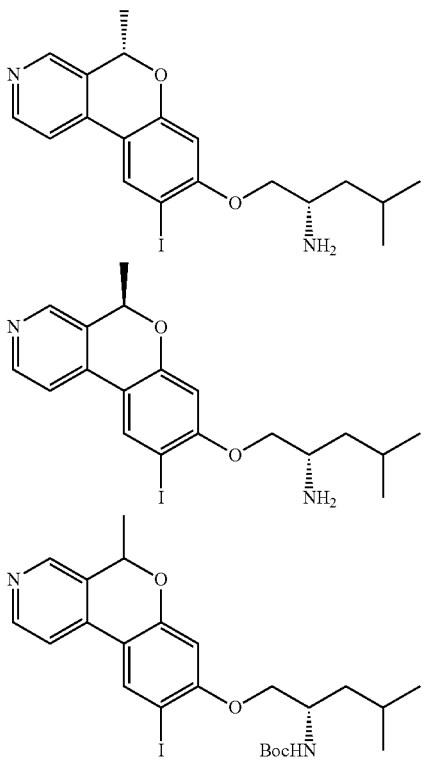

Part A. tert-butyl (2S)-1-(9-iodo-5-methyl-5H-chromeno[3,4-c]pyridin-8-yloxy)-4-methylpentan-2-ylcarbamate To a solution of tert-butyl ((2S)-4-methyl-1-((5-methyl-5H-chromeno[3,4-c]pyridin-8-yl)oxy)pentan-2-yl)carbamate (200 mg, 0.485 mmol) in acetonitrile (4 mL) was added NIS (654 mg, 2.91 mmol) and the mixture refluxed at 80° C. for 12 h. The volatiles were removed under reduced pressure. The residue was dissolved in water (10 mL) and the aqueous layer was extracted with ethyl acetate (3×10 mL). The combined organic layers were washed with brine (15 mL). The organic layer was dried over $Na_2SO_4$ and concentrated under reduced pressure. The crude product was purified by silica gel chromatography (pet ether: ethyl acetate) to afford tert-butyl ((2S)-1-((9-iodo-5-methyl-5H-chromeno[3,4-c]pyridin-8-yl)oxy)-4-methylpentan-2-yl)carbamate (150 mg, 0.237 mmol, 49% yield) as a dark brown oil. LCMS (ESI) m/e 539.0 [(M+H)$^+$, calcd for $C_{24}H_{321}N_2O_4$539.1]; LC/MS retention time (method D): $t_R$=1.84 min.

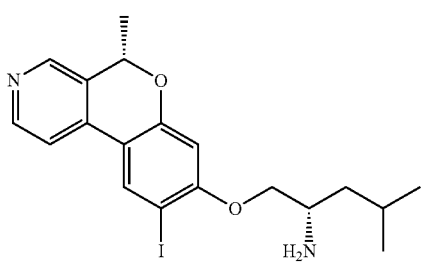

101

-continued

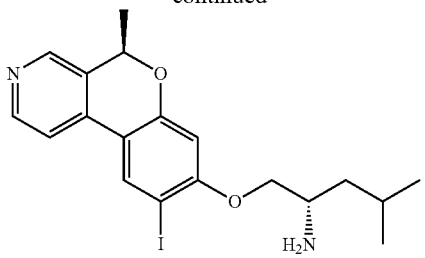

Part B. (2S)-1-(9-iodo-5-methyl-5H-chromeno[3,4-d]pyridin-8-yloxy)-4-methylpentan-2-amine Prepared as described in Example 8, Part D using tert-butyl ((2S)-1-((9-iodo-5-methyl-5H-chromeno[3,4-c]pyridin-8-yl)oxy)-4-methylpentan-2-yl)carbamate (150 mg, 0.279 mmol) to afford (2S)-1-(9-iodo-5-methyl-5H-chromeno[3,4-c]pyridin-8-yloxy)-4-methylpentan-2-amine (85 mg, 61% yield) as a yellow oil. LCMS (ESI) m/e 439.0 [(M+H)$^+$, calcd for $C_{19}H_{24}IN_2O_2$ 439.1]; LC/MS retention time (Method C): $t_R$=1.74 min. The racemate (28 mg, 0.06 mmol) was resolved into diastereomers by prep HPLC purification (TFA in water: MeCN) to afford two diastereomers (absolute stereochemistry of Me unknown). Obtained diastereomer 1 (7 mg, 0.015 mmol, 5% yield) as an off-white solid and diastereomer 2 (8 mg, 0.017 mmol, 6% yield) as a pale yellow sticky solid.

Diastereomer 1: $^1$H NMR (400 MHz, MeOD) δ 8.5 (d, J=5.6 Hz, 1H), 8.39 (s, 1H), 8.32 (s, 1H), 7.72 (d, J=5.2 Hz, 1H), 6.72 (s, 1H), 5.46 (d, J=6.8 Hz, 1H), 4.28 (m, 1H), 4.26 (m, 1H), 4.12 (m, 1H), 1.83 (m, 2H), 1.64 (m, 4H), 1.04 (m, 6H); LCMS (ESI) m/e 439.0 [(M+H)$^+$, calcd for $C_{19}H_{24}IN_2O_2$ 439.1] LC/MS retention time (Method E): $t_R$=1.88 min; HPLC retention time (method A): $t_R$=8.56 min; HPLC retention time (method B): $t_R$=10.04 min. Method: CHIRAL OD-H (250×4.6) mm 5 micron Mob. phase: 0.2% DEA in n-hexane: ethanol (80:20): $t_R$=8.89 min.

Diastereomer 2: $^1$H NMR (400 MHz, MeOD) δ 8.6 (d, J=5.2 Hz, 1H), 8.54 (s, 1H), 8.45 (s, 1H), 8.01 (d, J=5.6 Hz, 1H), 0.8 (d, J=8.8 Hz, 1H), 5.54 (m, 1H), 4.35 (m, 1H), 4.24 (m, 1H), 3.76 (m, 1H), 1.93 (m, 2H), 1.90 (m, 4H), 1.73 (m, 6H); LCMS (ESI) m/e 439.0 [(M+H)$^+$, calcd for $C_{19}H_{24}IN_2O_2$ 439.1] LC/MS retention time (Method E): $t_R$=1.89 min; HPLC retention time (method A): $t_R$=8.63 min; HPLC retention time (method B): $t_R$=10.03 min. Method: CHIRAL OD-H (250×4.6) mm 5 micron Mob. phase: 0.2% DEA in n-hexane: ethanol (80:20): $t_R$=15.69 min.

Example 32

(S)—N-(8-((2-amino-4-methylpentyl)oxy)-9-chloro-5H-chromeno[3,4-c]pyridin-2-yl)acetamide

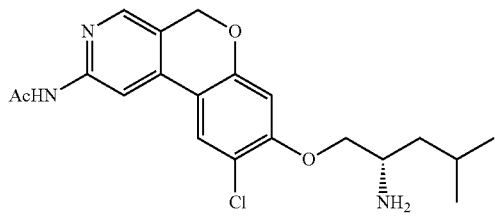

102

-continued

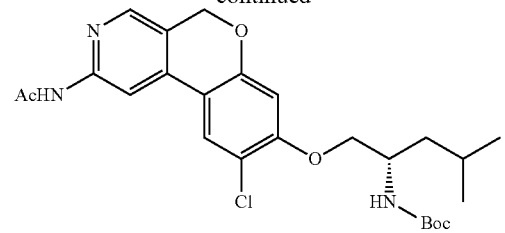

Part A. (S)-tert-butyl (1-((2-acetamido-9-chloro-5H-chromeno[3,4-c]pyridin-8-yl)oxy)-4-methylpentan-2-yl)carbamate The stirred solution of (S)-tert-butyl (1-((2-acetamido-5H-chromeno[3,4-c]pyridin-8-yl)oxy)-4-methylpentan-2-yl) carbamate (100 mg, 0.220 mmol) (prepared as described in Example 18, Part H) and NCS (29.3 mg, 0.220 mmol) in acetonitrile (15 mL) was heated to 80° C. for 12 h. The reaction mixture was cooled to room temperature and the solvent was removed under reduced pressure. The residue was partitioned between water (25 mL) and DCM (25 mL). The organic layer was washed with brine, dried over sodium sulphate and concentrated under reduced pressure to afford (S)-tert-butyl (1-((2-acetamido-9-chloro-5H-chromeno[3,4-c]pyridin-8-yl)oxy)-4-methylpentan-2-yl)carbamate (120 mg, 0.174 mmol, 79% yield) as an off-white solid. The product was used as is for the next step without purification. LCMS (ESI) m/e 490.2 [(M+H)$^+$, calcd for $C_{25}H_{33}ClN_3O_5$ 490.2]; LC/MS retention time (Method D): $t_R$=1.98 min.

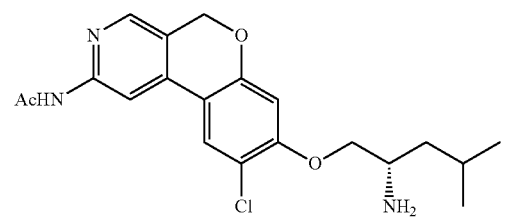 [SMILES: CC(=O)Nc1cc2c(cn1)COc1cc(OC[C@@H](N)CC(C)C)c(Cl)cc1-2]

Part B. (S)—N-(8-((2-amino-4-methylpentyl)oxy)-9-chloro-5H-chromeno[3,4-c]pyridin-2-yl)acetamide Prepared as described in Example 8, Part D using (S)-tert-butyl (1-((2-acetamido-9-chloro-5H-chromeno[3,4-c]pyridin-8-yl)oxy)-4-methylpentan-2-yl)carbamate to afford (S)—N-(8-((2-amino-4-methylpentyl)oxy)-9-chloro-5H-chromeno[3,4-c]pyridin-2-yl)acetamide (5 mg, 0.012 mmol, 11% yield) as a yellow solid. $^1$H NMR (400 MHz, MeOD) δ 8.19 (s, 1H), 8.08 (s, 1H), 7.95 (s, 1H), 6.88 (s, 1H), 5.22 (s, 2H), 4.42 (m, 1H), 4.24 (m, 1H), 3.75 (m, 1H), 2.29 (m, 3H), 1.79 (m, 2H), 1.72 (m, 1H), 1.18 (m, 6H); LCMS (ESI) m/e 390.2 [(M+H)$^+$, calcd for $C_{20}H_{25}ClN_3O_3$ 390.2]; LC/MS retention time (Method D): $t_R$=1.53 min; HPLC retention time (method A): $t_R$=9.17 min; HPLC retention time (method B): $t_R$=5.14 min.

Example 33

(S)-8-(2-amino-4-methylpentyloxy)-5H-chromeno[3,4-c]pyridin-2-amine

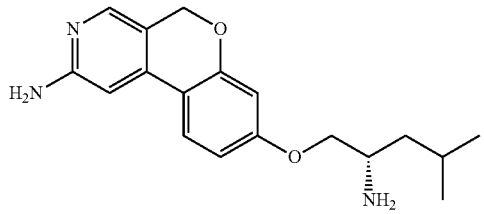 [SMILES: CC(C)C[C@H](N)COc1ccc2c(c1)OCc1cnc(N)cc1-2]

A stirred solution of (S)—N-(8-(((2-amino-4-methylpentyl)oxy)-5H-chromeno[3,4-c]pyridin-2-yl)acetamide (40 mg, 0.113 mmol) and NaOH (45.0 mg, 1.125 mmol) in a mixture of ethanol (10 mL) and water (4 mL) was heated to 90° C. for 18 h. The volatiles were removed under reduced pressure and the residue was partitioned between water (20 mL) and dichloromethane (15 mL).

The layers were separated and the aqueous layer was extracted with dichloromethane (15 mL). The combined organic layers were dried over sodium sulphate and concentrated under reduced to pressure to afford crude (S)-8-((2-amino-4-methylpentyl)oxy)-5H-chromeno[3,4-c]pyridin-2-amine (23 mg, 0.068 mmol, 60% crude yield) which was taken in MeOH (2 mL) and cooled to 0° C.

The resultant solution was treated with 1M HCl in diethyl ether (15 mL, 0.068 mmol) and the reaction was stirred at room temperature for 14 h. The reaction mixture was then cooled to 0° C. to afford a solid which was filtered, washed with diethyl ether (10 mL) and dried under vacuum to afford (S)-8-((2-amino-4-methylpentyl)oxy)-5H-chromeno[3,4-c]pyridin-2-amine dihydrochloride (11 mg, 0.025 mmol, 37% yield for two steps) as a brown solid. $^1$H NMR (400 MHz, MeOD) δ 7.88 (d, J=6.9 Hz, 1H), 7.78 (s, 1H), 7.17 (s, 1H), 6.89 (m, 1H), 6.75 (d, J=2.1 Hz, 1H), 5.07 (s, 2H), 4.84-4.34 (m, 1H), 4.17-4.13 (m, 1H), 3.71 (m, 1H), 1.82-1.75 (m, 1H), 1.73-1.66 (m, 2H), 1.04 (m, 6H). LCMS (ESI) m/e 314.2 [(M+H)$^+$, calcd for $C_{18}H_{24}N_3O_2$ 314.2]; LC/MS retention time (Method D): $t_R$=1.1 min; HPLC retention time (method A): $t_R$=5.16 min; HPLC retention time (method B): $t_R$=8.96 min.

Example 34

(S)-8-((2-amino-4-methylpentyl)oxy)-4-methyl-5H-chromeno[3,4-c]pyridin-5-one

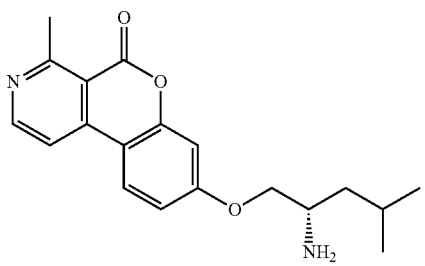

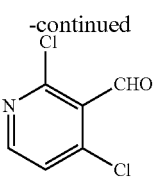

Part A. 2,4-dichloronicotinaldehyde

To a solution of 2,4-dichloropyridine (2 g, 13.51 mmol) in tetrahydrofuran (20 mL) at −78° C., was added LDA, 2M in THF/heptane/ethylbenzene (8.11 mL, 16.22 mmol) and the solution was stirred for 30 min. DMF (10.46 mL, 135 mmol) was added and the solution was stirred for 1 h and then warmed RT. The reaction mixture was quenched with saturated $NH_4Cl$ solution and diluted with ethyl acetate (50 mL). The organic layer was washed with saturated $NaHCO_3$ (2×10 mL), water (20 mL), dried over $Na_2SO_4$ and concentrated under reduced pressure to afford 2,4-dichloronicotinaldehyde (2 g, 11.36 mmol, 84% yield) as a yellow solid. $^1$H NMR (400 MHz, CDCl$_3$) δ 10.49 (s, 1H),), 8.44 (d, J=5.4 Hz, 1H), 7.43 (d, J=5.4 Hz, 1H).

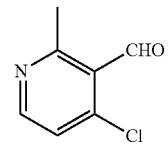

Part B. 4-chloro-2-methylnicotinaldehyde

A mixture of 2,4-dichloronicotinaldehyde (1.1 g, 6.25 mmol), 2,4,6-trimethyl-1,3,5,2,4,6-trioxatriborinane (0.942 g, 7.50 mmol), $Cs_2CO_3$ (6.11 g, 18.75 mmol) and $PdCl_2$ (dppf) (0.229 g, 0.312 mmol) in 1,4-dioxane (9 mL) and water (1 mL) was heated at 100° C. for 18 h. After cooling, the mixture was diluted with ethyl acetate (15 mL) and water (20 mL). The ethyl acetate layer was dried over $Na_2SO_4$, concentrated and purified by silica gel chromatography to afford 4-chloro-2-methylnicotinaldehyde (0.16 g, 1.028 mmol, 16% yield) as a yellow solid $^1$H NMR (400 MHz, CDCl$_3$) δ 10.69 (s, 1H), 8.52 (d, J=7.2 Hz, 1H), 7.32 (d, J=7.2 Hz, 1H), 2.83 (s, 3H).

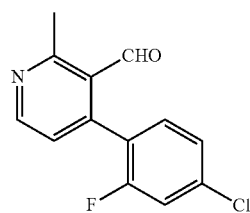 [SMILES: Cc1nccc(-c2ccc(Cl)cc2F)c1C=O]

Part C. 4-(4-chloro-2-fluorophenyl)-2-methylnicotinaldehyde

A mixture of 4-chloro-2-methylnicotinaldehyde (100 mg, 0.643 mmol), (4-chloro-2-fluorophenyl)boronic acid (123 mg, 0.707 mmol), $Cs_2CO_3$ (628 mg, 1.928 mmol) and $Pd(Ph_3P)_4$ (52.0 mg, 0.045 mmol) in toluene (5 mL) was heated at 90° C. for 16 h. After cooling, the reaction mixture was diluted with EtOAc (10 mL) and water (10 mL). The ethyl acetate layer was concentrated and purified by silica gel chromatography (2:1 Hexane-EtOAc) to afford 4-(4-chloro-2-fluorophenyl)-2-methylnicotinaldehyde (0.15 g, 0.601 mmol, 35% yield) as a yellow solid. LCMS (ESI) m/e 250.04 [(M+H)$^+$, calcd for $C_{13}H_{10}ClFNO$ 250.0]; LC/MS retention time (Method G): $t_R$=0.96 min.

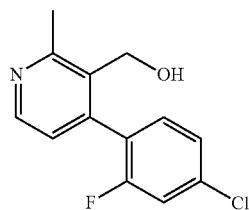 [SMILES: Cc1nccc(-c2ccc(Cl)cc2F)c1CO]

Part D. (4-(4-chloro-2-fluorophenyl)-2-methylpyridin-3-yl)methanol

To a solution of 4-(4-chloro-2-fluorophenyl)-2-methylnicotinaldehyde (60 mg, 0.240 mmol) in MeOH (2 mL) at 0° C., was added NaBH$_4$ (27.3 mg, 0.721 mmol) and the solution stirred for 3 h at RT. The mixture was concentrated and diluted with EtOAc (15 mL) and water (10 mL). The organic layers were dried over Na$_2$SO$_4$, filtered and concentrated under reduced pressure to afford (4-(4-chloro-2-fluorophenyl)-2-methylpyridin-3-yl)methanol (0.15 g, 0.596 mmol, 89% yield) as a brown solid. LCMS (ESI) m/e 252.03 [(M+H)$^+$, calcd for $C_{13}H_{12}ClFNO$ 252.1]; LC/MS retention time (Method G): $t_R$=0.80 min.

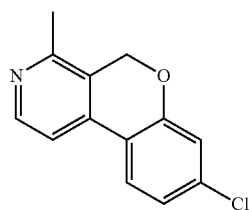 [SMILES: Cc1nccc2c1COc1cc(Cl)ccc1-2]

Part E.
8-chloro-4-methyl-5H-chromeno[3,4-c]pyridine

To a solution of (4-(4-chloro-2-fluorophenyl)-2-methylpyridin-3-yl)methanol (70 mg, 0.278 mmol) in tetrahydrofuran (3 mL) at 0° C. was added NaH (33.4 mg, 0.834 mmol) portionwise. The solution was allowed to warm to room temperature and stirred for 5 h. The reaction mixture was quenched with ice cold water and diluted with EtOAc (15 mL). The organic layer was dried over Na$_2$SO$_4$, filtered and concentrated under reduced pressure to afford 8-chloro-4-methyl-5H-chromeno[3,4-c]pyridine (0.11 g, 0.475 mmol, 73% yield) as a brown solid. LCMS (ESI) m/e 232.00 [(M+H)$^+$, calcd for $C_{13}H_{12}ClNO$ 232.01]; LC/MS retention time (Method G): $t_R$=1.00 min.

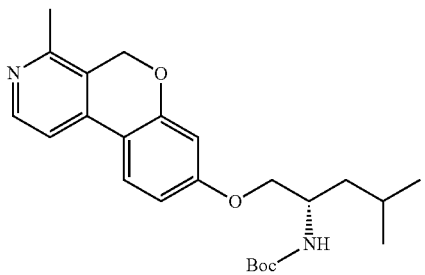 [SMILES: Cc1nccc2c1COc1cc(OC[C@H](CC(C)C)NC(=O)OC(C)(C)C)ccc1-2]

Part F. (S)-tert-butyl (4-methyl-1-((4-methyl-5H-chromeno[3,4-c]pyridin-8-yl)oxy)pentan-2-yl)carbamate A mixture of 8-chloro-4-methyl-5H-chromeno[3,4-c]pyridine (60 mg, 0.259 mmol), (S)-(−)-2-(tert-butoxycarbonylamino)-4-methyl-1-pentanol (113 mg, 0.518 mmol), 2-di-t-butylphosphino-2',4',6'-tri-1-propyl-1,1'-biphenyl (6.60 mg, 0.016 mmol), Cs$_2$CO$_3$ (127 mg, 0.388 mmol) and Pd(OAc)$_2$ (1.744 mg, 7.77 μmol) in toluene (5 mL) was heated at 80° C. for 16 h. After cooling to rt, the mixture was diluted with EtOAc (10 mL) and water (10 mL). The organic layer was dried over Na$_2$SO$_4$, filtered and concentrated under reduced pressure to afford (S)-tert-butyl (4-methyl-1-((4-methyl-5H-chromeno[3,4-c]pyridin-8-yl)oxy)pentan-2-yl)carbamate, (0.2 g, 0.485 mmol, 30% yield) as a yellow solid. LCMS (ESI) m/e 413.39 [(M+H)$^+$, calcd for $C_{24}H_{33}N_2O_4$ 413.24]; LC/MS retention time (Method F): $t_R$=0.97 min.

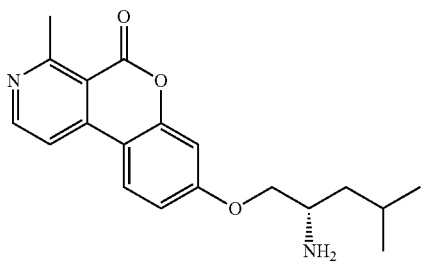

Part G. (S)-8-(2-amino-4-methylpentyl)oxy)-4-methyl-5H-chromeno[3,4-e]pyridin-5-one A solution of (S)-tert-butyl (4-methyl-1-((4-methyl-5H-chromeno[3,4-c]pyridin-8-yl)oxy)pentan-2-yl)carbamate (35 mg, 0.085 mmol) in DCM (3 mL) was cooled to 0° C. and then TFA (0.033 mL, 0.424 mmol) was added. The reaction mixture was stirred at room temperature for 2 h, then neutralized with saturated NaHCO$_3$ and extracted with EtOAc (3×5 mL). Organic layer was dried over Na$_2$SO$_4$, filtered and concentrated under reduced pressure to afford crude which was purified by column chromatography on silica gel to afford material which air oxidized during purification to afford (S)-8-(((2-amino-4-methylpentyl)oxy)-4-methyl-5H-chromeno[3,4-c]pyridin-5-one (3 mg, 9.19 umol, 10% yield) as yellow solid. $^1$H NMR (400 MHz, CD$_3$OD) δ 8.67 (d, J=5.6 Hz, 1H) 8.19-8.23 (m, 1H) 8.02-8.06 (d, J=5.6 Hz, 1H) 7.06-7.10 (m, 1H), 6.98 (s, 1H), 4.08-4.14 (m, 1H), 3.91-3.97 (m, 1H), 3.28-3.30 (m, 1H), 3.01 (s, 3H), 1.80-1.88 (m, 1H), 1.41-1.48 (m, 2H), 0.97-1.03 (m, 6H); LCMS (ESI) m/e 327.2 [(M+H)$^+$, calcd for $C_{19}H_{23}N_2O_3$ 327.2]; LC/MS retention time (Method G): $t_R$=0.82 min; HPLC retention time (method A): $t_R$=8.47 min; HPLC retention time (method B): $t_R$=8.90 min.

Example 35

(S)—N-(8-((2-amino-4-methylpentyl)oxy)-7-methyl-5H-chromeno[3,4-c]pyridin-2-yl)acetamide

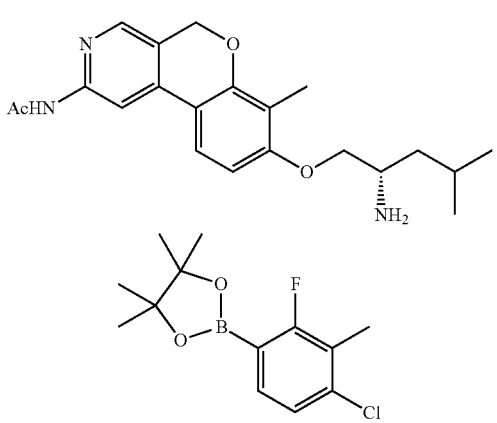

Part A. 2-(4-chloro-2-fluoro-3-methylphenyl)-4,4,5,5-tetramethyl-1,3,2-dioxaborolane To a stirred solution of 1-bromo-4-chloro-2-fluoro-3-methylbenzene (1.70 g, 7.61 mmol) in tetrahydrofuran (45 mL) cooled to −10° C. was added isopropylmagnesium chloride (2.9 M in THF) (3.0 mL, 8.75 mmol) dropwise. The reaction mixture was stirred at −10° C. for 1 h then allowed to warm to 0° C. and stirred for 1 h. The reaction mixture was cooled to −10° C. followed by the addition of 2-isopropoxy-4,4,5,5-tetramethyl-1,3,2-dioxaborolane (1.785 mL, 8.75 mmol) dropwise. The reaction was allowed to warm to room temperature and stirred for 14 h. The reaction mixture was quenched with 1 N aqueous sodium hydroxide solution and stirred for 10 min. The pH of the reaction was adjusted to 3 with concentrated HCl and the solution was extracted with ethyl acetate (2×30 mL). The combined organic layers were washed with water (50 mL), brine (50 mL), dried over sodium sulphate, and concentrated under reduced pressure to afford 2-(4-chloro-2-fluoro-3-methylphenyl)-4,4,5,5-tetramethyl-1,3,2-dioxaborolane (1.75 g, 6.47 mmol, 85% yield) which was taken to the next step without purification. $^1$H NMR (400 MHz, CDCl$_3$) δ 7.47 (m, 1H), 7.14 (d, J=8 Hz, 1H), 2.29 (d, J=2 Hz, 3H), 1.36 (s, 12H).

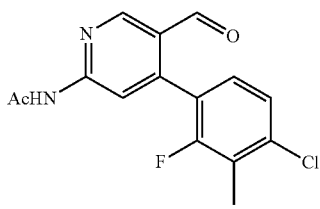 [SMILES: CC(=O)Nc1cc(-c2ccc(Cl)c(C)c2F)c(C=O)cn1]

Part B. N-(4-(4-chloro-2-fluoro-3-methylphenyl)-5-formylpyridin-2-yl)acetamide Prepared as described in Example 5, Part B using 2-(4-chloro-2-fluoro-3-methylphenyl)-4,4,5,5-tetramethyl-1,3,2-dioxaborolane to afford N-(4-(4-chloro-2-fluoro-3-methylphenyl)-5-formylpyridin-2-yl)acetamide (1.02 g, 3.04 mmol, 82% yield) as a white solid. LCMS (ESI) m/e 307.0 [(M+H)$^+$, calcd for C$_{15}$H$_{13}$ClFN$_2$O$_2$ 307.1]; LC/MS retention time (Method E): t$_R$=1.95 min.

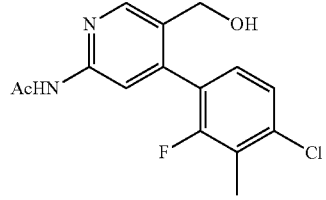 [SMILES: CC(=O)Nc1cc(-c2ccc(Cl)c(C)c2F)c(CO)cn1]

Part C. N-(4-(4-chloro-2-fluoro-3-methylphenyl)-5-(hydroxymethyl)pyridin-2-yl)acetamide Prepared as described in Example 5, Part C using N-(4-(4-chloro-2-fluoro-3-methylphenyl)-5-formylpyridin-2-yl)acetamide to afford N-(4-(4-chloro-2-fluoro-3-methylphenyl)-5-(hydroxymethyl)pyridin-2-yl)acetamide (1.1 g, 2.39 mmol, 73% yield) as an off-white solid. LCMS (ESI) m/e 309.0 [(M+H)$^+$, calcd for C$_{15}$H$_{15}$ClFN$_2$O$_2$ 309.1]; LC/MS retention time (Method E): t$_R$=1.85 min.

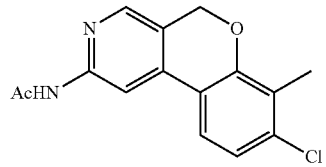 [SMILES: CC(=O)Nc1cc2c(cn1)COc1c-2ccc(Cl)c1C]

Part D. N-(8-chloro-7-methyl-5H-chromeno[3,4-c]pyridin-2-yl)acetamide

Prepared as described in Example 5, Part D using N-(4-(4-chloro-2-fluoro-3-methylphenyl)-5-(hydroxymethyl)pyridin-2-yl)acetamide to afford N-(8-chloro-7-methyl-5H-chromeno[3,4-c]pyridin-2-yl)acetamide (150 mg, 0.514 mmol, 18% yield) as a white solid. LCMS (ESI) m/e 289.0 [(M+H)$^+$, calcd for C$_{15}$H$_{14}$ClN$_2$O$_2$ 289.1]; LC/MS retention time (Method E): t$_R$=1.9 min.

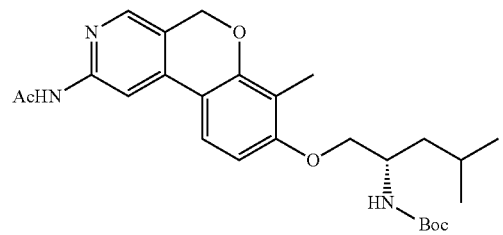 [SMILES: CC(=O)Nc1cc2c(cn1)COc1c-2ccc(OC[C@H](CC(C)C)NC(=O)OC(C)(C)C)c1C]

Part E. (S)-tert-butyl (1-((2-acetamido-7-methyl-5H-chromeno[3,4-c]pyridin-8-yl)oxy)-4-methylpentan-2-yl)carbamate Prepared as described in Example 8, Part C using (S)-tert-butyl (1-hydroxy-4-methylpentan-2-yl)carbamate and N-(8-chloro-7-methyl-5H-chromeno[3,4-c]pyridin-2-yl)acetamide to afford (S)-tert-butyl (1-((2-acetamido-7-methyl-5H- chromeno[3,4-c]pyridin-8-yl)oxy)-4-methylpentan-2-yl)carbamate (168 mg, 0.037 mmol, 11% yield) as a brown oil. LCMS (ESI) m/e 470.3 [(M+H)+, calcd for C26H36N3O5 470.3]; LC/MS retention time (Method F): tR=0.96 min.

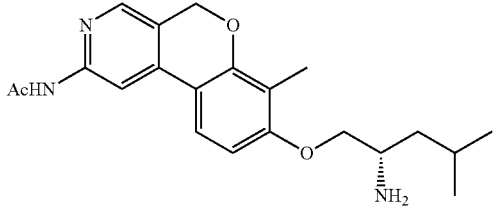 [SMILES: CC(=O)Nc1cc2c(cn1)COc1c-2ccc(OC[C@@H](N)CC(C)C)c1C]

Part F. (S)—N-(8-((2-amino-4-methylpentyl)oxy)-7-methyl-5H-chromeno[3,4-c]pyridin-2-yl)acetamide Prepared as described in Example 8, Part D using (S)-tert-butyl (1-((2-acetamido-7-methyl-5H-chromeno[3,4-c]pyridin-8-yl)oxy)-4-methylpentan-2-yl)carbamate to afford yield (S)—N-(8-(((2-amino-4-methylpentyl)oxy)-7-methyl-5H-chromeno[3,4-c]pyridin-2-yl)acetamide, TFA salt (9 mg, 0.022 mmol, 64% yield) as a yellow solid. ¹H NMR (400 MHz, MeOD) δ 8.18 (s, 1H), 8.11 (s, 1H), 7.76 (d, J=8.4 Hz, 1H), 6.87 (d, J=8.8 Hz, 1H), 5.19 (s, 2H), 4.33 (m, 1H), 4.20 (m, 1H), 3.75 (m, 1H), 2.27 (s, 3H), 2.23 (s, 3H), 1.8-1.67 (m, 3H), 1.07-1.04 (m, 6H). LCMS (ESI) m/e 370.2 [(M+H)+, calcd for C21H28N3O3 370.2]; LC/MS retention time (Method I): tR=1.75 min; HPLC retention time (method A): tR=9.34 min; HPLC retention time (method B): tR=10.3 min.

din-8-yl)oxy)-5,5,5-trifluoropentan-2-yl)carbamate (0.023 g, 0.021 mmol, 12% yield) as a yellow oil. LCMS (ESI) m/e 496.6 [(M+H)+, calcd for C24H29F3N3O5 496.2] LC/MS retention time (method F): tR=0.88 min.

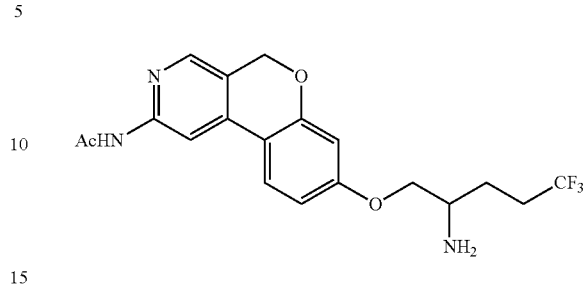

Part B. N-(8-((2-amino-5,5,5-trifluoropentyl)oxy)-5H-chromeno[3,4-d]pyridin-2-yl)acetamide Prepared as described in Example 8, Part D using tert-butyl (1-((2-acetamido-5H-chromeno[3,4-c]pyridin-8-yl)oxy)-5,5,5-trifluoropentan-2-yl)carbamate (0.023 g, 0.021 mmol) to afford N-(8-((2-amino-5,5,5-trifluoropentyl)oxy)-5H-chromeno[3,4-c]pyridin-2-yl)acetamide, 2 TFA (6.02 mg, 9.46 μmol, 44% yield) as a yellow semi solid. ¹H NMR (400 MHz, MeOD) δ 8.18 (s, 1H), 8.01 (s, 1H), 7.87 (d, J=8.8 Hz, 1H), 6.89 (m, 1H), 6.76 (d, J=2.8 Hz, 1H), 5.20 (s, 2H), 4.38 (m, 1H), 4.25 (m, 1H), 3.82 (m, 1H), 2.52 (m, 2H), 2.32 (s, 3H), 2.15 (m, 2H); LCMS (ESI) m/e 396.2 [(M+H)+, calcd for C19H21F3N3O3 396.1]; LC/MS retention time (method H): tR=1.53 min; HPLC retention time (method A): tR=8.13 min; HPLC retention time (method B): tR=8.64 min.

Example 36

N-(8-((2-amino-5,5,5-trifluoropentyl)oxy)-5H-chromeno[3,4-c]pyridin-2-yl)acetamide Example 37

(S)—N-(8-((2-amino-4-methylpentyl)oxy)-7-methoxy-5H-chromeno[3,4-c]pyridin-2-yl)acetamide

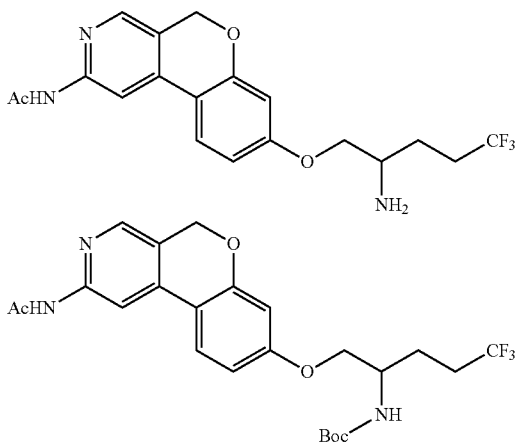

Part A. tert-butyl 1-(2-acetamido-5H-chromeno[3,4-d]pyridin-8-yloxy)-5,5,5-trifluoropentan-2-ylcarbamate Prepared as described in Example 18, Part H using N-(8-chloro-5H-chromeno[3,4-c]pyridin-2-yl)acetamide (0.1 g, 0.175 mmol) (prepared as described in Example 18, Part G) to afford tert-butyl (1-((2-acetamido-5H-chromeno[3,4-c]pyri-

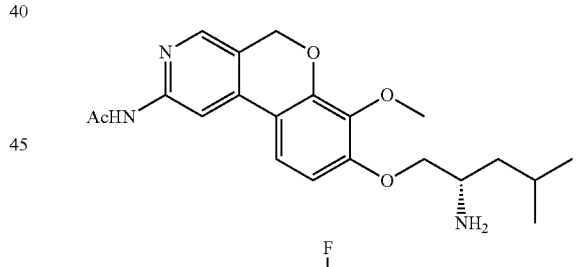

Part A. 3-bromo-6-chloro-2-fluorophenol

To a stirred solution of 1-bromo-4-chloro-2-fluorobenzene (5 g, 23.87 mmol) in tetrahydrofuran (40 mL) was cooled to −78° C. was added LDA, 2M in THF/heptane/ethylbenzene (14.92 mL, 29.8 mmol) dropwise and the reaction mixture was stirred at this temperature for 30 min. The solution was allowed to warm to −20° C. and stirred for 30 min. The reaction was cooled to −78° C. and trimethyl borate (3.47 mL, 31.0 mmol) dissolved in THF (5 mL) was added dropwise and the reaction mixture was warmed to −20° C. and stirred for 1 h. The reaction mixture was cooled to −78° C. and peracetic acid (16 mL, 84 mmol) was added dropwise and the mixture allowed to warm to rt and stirred for 12 h. The reaction mixture was cooled to 0° C. and quenched with 5% aqueous ammonium chloride and extracted with ethyl acetate (2×50 mL). The combined organic layers were washed with brine (50 mL). The organic layer was dried over sodium sulphate and concentrated under reduced pressure to yield 3-bromo-6-chloro-2-fluorophenol (4.99 g, 18.25 mmol, 76% yield) as yellow oil. LCMS (ESI) m/e 225.1 [(M+H)$^+$, calcd for $C_6H_4BrClFO$ 224.9]; LC/MS retention time (method G): $t_R$=0.87 min.

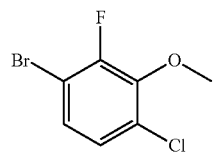

Part B.
1-bromo-4-chloro-2-fluoro-3-methoxybenzene

To a stirred solution of 3-bromo-6-chloro-2-fluorophenol (4.2 g, 18.63 mmol) in acetonitrile (35 mL) was added potassium carbonate (5.15 g, 37.3 mmol) followed by the addition of methyl iodide (2.330 mL, 37.3 mmol) dropwise at rt. The reaction mixture was heated to 85° C. for 3 h. The volatiles were evaporated; water (50 mL) was added and the solution extracted with ethyl acetate (2×80 mL). The combined organic layers were washed with brine (100 mL), dried over sodium sulphate, and concentrated under reduced pressure. The crude material was taken to the next step without further purification. $^1$H NMR (400 MHz, CDCl$_3$) δ 7.20 (m, 1H), 7.05 (m, 1H), 3.98 (s, 3H).

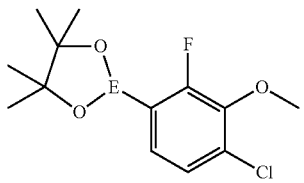

Part C. 2-(4-chloro-2-fluoro-3-methoxyphenyl)-4,4,5,5-tetramethyl-1,3,2-dioxaborolane To a stirred solution of 1-bromo-4-chloro-2-fluoro-3-methoxybenzene (2.6 g, 10.86 mmol) in tetrahydrofuran (30 mL) cooled to −10° C. was added isopropylmagnesium bromide (4.49 mL, 13.03 mmol) dropwise and the reaction mixture was stirred at this temperature for 1 h. The reaction mixture was then warmed to 0° C. and stirred for 1 h. The reaction mixture was cooled to −10° C. and 2-isopropoxy-4,4,5,5-tetramethyl-1,3,2-dioxaborolane (2.215 mL, 10.86 mmol) was added dropwise. The reaction mixture was warmed to room temperature and stirring continued for 16 h. The reaction was quenched with 5% aqueous sodium hydroxide and extracted with ethyl acetate (2×25 mL). The combined organic layers were washed with brine (25 mL), dried over sodium sulphate, and concentrated under reduced pressure to afford 2-(4-chloro-2-fluoro-3-methoxyphenyl)-4,4,5,5-tetramethyl-1,3,2-dioxaborolane (2.15 g, 7.50 mmol, 69% yield) as a brown oil. $^1$H NMR (400 MHz, CDCl$_3$) δ 7.35 (m, 1H), 7.13 (m, 1H), 3.96 (s, 3H), 1.36 (s, 12H).

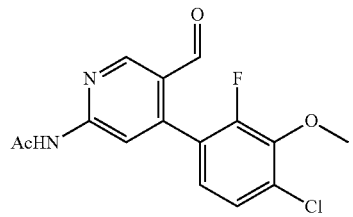 [SMILES: COc1c(Cl)ccc(-c2cc(NC(C)=O)ncc2C=O)c1F]

Part D. N-(4-(4-chloro-2-fluoro-3-methoxyphenyl)-5-formylpyridin-2-yl)acetamide

A stirred solution of N-(4-chloro-5-formylpyridin-2-yl)acetamide (1.947 g, 8.72 mmol) (prepared as described in Example 18, Part D), 2-(4-chloro-2-fluoro-3-methoxyphenyl)-4,4,5,5-tetramethyl-1,3,2-dioxaborolane (2.5 g, 8.72 mmol), cesium carbonate (5.69 g, 17.45 mmol) and Pd(PPh$_3$)$_4$ (0.504 g, 0.436 mmol) in a mixture of dioxane (30 mL) and water (5 mL) was purged with nitrogen for 5 minutes then heated to 85° C. for 14 h. The reaction mixture was cooled to rt and diluted with water (10 mL). The mixture was extracted with ethyl acetate (2×15 mL). The combined organic layers were washed with brine (20 mL), dried over sodium sulphate, and concentrated under reduced pressure. The residue was purified by silica gel chromatography using a gradient of ethyl acetate in hexanes to yield N-(4-(4-chloro-2-fluoro-3-methoxyphenyl)-5-formylpyridin-2-yl)acetamide (1.78 g, 2.95 mmol, 34% yield) as a white solid. LCMS (ESI) m/e 322.9 [(M+H)$^+$, calcd for $C_{15}H_{13}ClFN_2O_3$ 323.1]; LC/MS retention time (Method F): $t_R$=0.89 min.

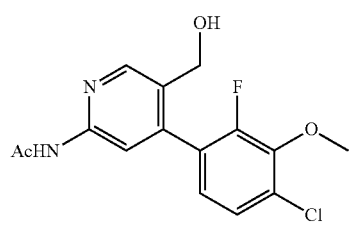 [SMILES: COc1c(Cl)ccc(-c2cc(NC(C)=O)ncc2CO)c1F]

Part E. N-(4-(4-chloro-2-fluoro-3-methoxyphenyl)-5-(hydroxymethyl)pyridin-2-yl)acetamide To a stirred solution of N-(4-(4-chloro-2-fluoro-3-methoxyphenyl)-5-formylpyridin-2-yl)acetamide (1.7 g, 2.370 mmol) in a mixture of THF (15 mL) and methanol (5 mL) was added sodium borohydride (0.090 g, 2.370 mmol) in two portions and the reaction mixture was stirred at room temperature for 30 min. The volatiles were removed, water (15 mL) was added and the solution extracted with ethyl acetate (2×20 mL). The combined organic layers were washed with brine (15 mL), dried over sodium sulphate, and concentrated under reduced pressure to afford N-(4-(4-chloro-2-fluoro-3-methoxyphenyl)-5-(hydroxymethyl)pyridin-2-yl)acetamide (1.6 g, 1.88 mmol, 38% yield) as a brown solid. The compound was carried into the next step without further purification. LCMS (ESI) m/e 324.9 [(M+H)$^+$, calcd for $C_{15}H_{15}ClFN_2O_3$ 325.1]; LC/MS retention time (Method F): $t_R$=0.97 min.

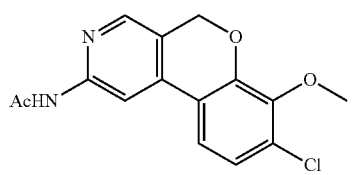 [SMILES: COc1c(Cl)ccc2c1OCc1cnc(NC(C)=O)cc1-2]

Part F. N-(8-chloro-7-methoxy-5H-chromeno[3,4-c]pyridin-2-yl)acetamide

Prepared as described in Example 5, Part D using N-(4-(4-chloro-2-fluoro-3-methoxyphenyl)-5-(hydroxymethyl)pyridin-2-yl)acetamide to afford N-(8-chloro-7-methoxy-5H-chromeno[3,4-c]pyridin-2-yl)acetamide (250 mg, 0.743 mmol, 34% yield) as a white solid. LCMS (ESI) m/e 305.0 [(M+H)$^+$, calcd for $C_{15}H_{14}ClN_2O_3$ 305.1]; LC/MS retention time (Method G): $t_R$=0.88 min.

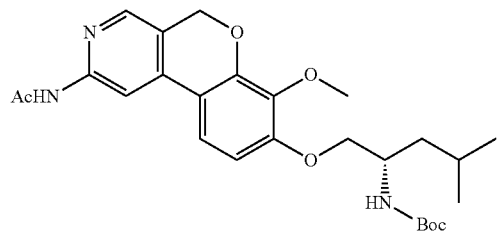 [SMILES: COc1c(OC[C@H](CC(C)C)NC(=O)OC(C)(C)C)ccc2c1OCc1cnc(NC(C)=O)cc1-2]

Part G. (S)-tert-butyl (1-((2-acetamido-7-methoxy-5H-chromeno[3,4-c]pyridin-8-yl)oxy)-4-methylpentan-2-yl)carbamate Prepared as described in Example 18, Part H using (S)-tert-butyl (1-hydroxy-4-methylpentan-2-yl)carbamate and N-(8-chloro-7-methoxy-5H-chromeno[3,4-c]pyridin-2-yl)acetamide to afford (S)-tert-butyl (1-((2-acetamido-7-methoxy-5H-chromeno[3,4-c]pyridin-8-yl)oxy)-4-methylpentan-2-yl)carbamate (112 mg, 0.089 mmol, 60% yield) as a brown oil. LCMS (ESI) m/e 486.2 [(M+H)$^+$, calcd for $C_{26}H_{36}N_3O_6$ 486.2]; LC/MS retention time (Method F): $t_R$=0.91 min.

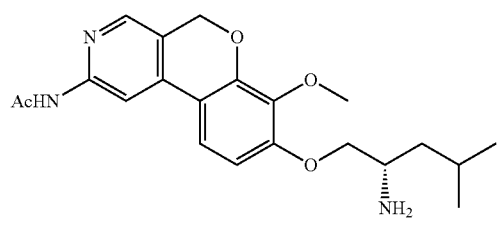 [SMILES: COc1c(OC[C@@H](N)CC(C)C)ccc2c1OCc1cnc(NC(C)=O)cc1-2]

Part H. (S)—N-(8-((2-amino-4-methylpentyl)oxy)-7-methoxy-5H-chromeno[3,4-c]pyridin-2-yl)acetamide To a stirred solution of (S)-tert-butyl (1-((2-acetamido-7-methoxy-5H-chromeno[3,4-c]pyridin-8-yl)oxy)-4-methylpentan-2-yl)carbamate (111 mg, 0.088 mmol) in dichloromethane (2 mL) was added TFA (0.027 mL, 0.352 mmol) dropwise and the reaction mixture was stirred at room temperature for 12 h. After completion of reaction, the volatiles were removed under reduced pressure to afford a residue which was purified by prep. HPLC (Sunfire C18 3.5 um, 19×150 mm column and 10 mM ammonium acetate in water) to yield (S)—N-(8-((2-amino-4-methylpentyl)oxy)-7-methoxy-5H-chromeno[3,4-c]pyridin-2-yl)acetamide (10 mg, 0.022 mmol, 25% yield) as white solid. $^1$H NMR (400 MHz, MeOD) δ 8.38 (s, 1H), 8.17 (s, 1H), 7.6 (d, J=8.8 Hz, 1H), 6.88 (d, J=8.8 Hz, 1H), 5.18 (s, 2H), 3.9 (s, 3H), 2.2 (s, 3H), 1.94 (m, 3H), 1.86-1.81 (m, 1H), 1.70-1.65 (m, 1H), 1.63-1.55 (m, 1H), 1.04 (m, 6H); LCMS (ESI) m/e 386.2 [(M+H)$^+$, calcd for $C_{21}H_{28}N_3O_4$ 386.2]; LC/MS retention time (Method E): $t_R$=1.99 min; HPLC retention time (method A): $t_R$=8.80 min; HPLC retention time (method B): $t_R$=9.73 min.

Example 38

(S)—N-(8-(2-amino-4-methylpentyloxy)-7-(difluoromethyl)-5H-chromeno[3,4-d]pyridin-2-yl)acetamide

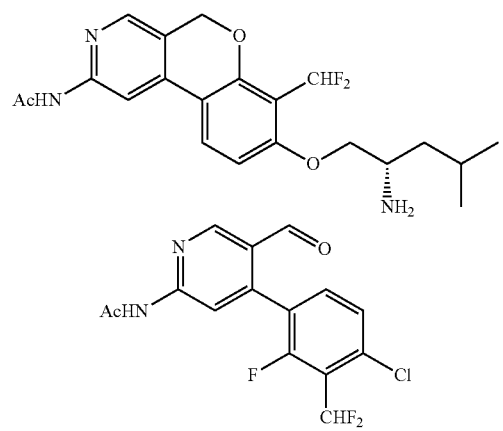

Part A, N-(4-(4-chloro-3-(difluoromethyl)-2-fluorophenyl)-5-formylpyridin-2-yl)acetamide Prepared as described in Example 37, Part D using N-(4-chloro-5-formylpyridin-2-yl)acetamide (prepared as described in Example 18, Part D), to afford N-(4-(4-chloro-3-(difluoromethyl)-2-fluorophenyl)-5-formylpyridin-2-yl)acetamide (40 mg, 0.1 mmol, 28% yield). LCMS (ESI) m/e 343.0 [(M+H)$^+$, calcd for $C_{15}H_{11}ClF_3N_2O_2$ 343.03]; LC/MS retention time (Method E): $t_R$=1.91 min.

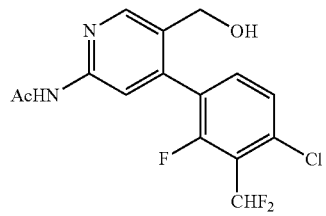 [SMILES: CC(=O)Nc1cc(-c2ccc(Cl)c(C(F)F)c2F)c(CO)cn1]

Part B. N-(4-(4-chloro-3-(difluoromethyl)-2-fluorophenyl)-5-(hydroxymethyl)pyridin-2-yl)acetamide Prepared as described in Example 5, Part C using N-(4-(4-chloro-3-(difluoromethyl)-2-fluorophenyl)-5-formylpyridin-2-yl)acetamide to afford N-(4-(4-chloro-3-(difluoromethyl)-2-fluorophenyl)-5-(hydroxymethyl)pyridin-2-yl)acetamide (1.1 g, 2.84 mmol, 76% yield) as a brown solid. LCMS (ESI) m/e 345.0 [(M+H)$^+$, calcd for C$_{15}$H$_{13}$ClF$_3$N$_2$O$_2$ 345.0]; LC/MS retention time (Method: H): t$_R$=1.92 min.

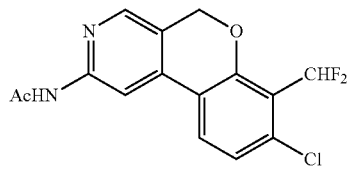 [SMILES: CC(=O)Nc1cc2c(cn1)COc1c-2ccc(Cl)c1C(F)F]

Part C. N-(8-chloro-7-(difluoromethyl)-5H-chromeno[3,4-c]pyridin-2-yl)acetamide

Prepared as described in Example 5, Part D using afford N-(4-(4-chloro-3-(difluoromethyl)-2-fluorophenyl)-5-(hydroxymethyl)pyridin-2-yl)acetamide to afford N-(8-chloro-7-(difluoromethyl)-5H-chromeno[3,4-c]pyridin-2-yl)acetamide (900 mg, 2.66 mmol, 94% yield) as a pale yellow solid. LCMS (ESI) m/e 325.0 [(M+H)$^+$, calcd for C$_{15}$H$_{12}$ClF$_2$N$_2$O$_2$ 325.0]; LC/MS retention time (Method: H): t$_R$=2.21 min.

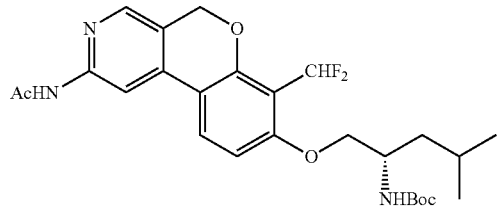 [SMILES: CC(=O)Nc1cc2c(cn1)COc1c-2ccc(OC[C@H](CC(C)C)NC(=O)OC(C)(C)C)c1C(F)F]

Part D. (S)-tert-butyl 1-(2-acetamido-7-(difluoromethyl)-5H-chromeno[3,4-c]pyridin-8-yloxy)-4-methylpentan-2-ylcarbamate Prepared as described in Example 18, Part H using N-(8-(((S)-2-amino-4-methylpentyl)oxy)-5-methyl-5H-chromeno[3,4-c]pyridin-4-yl)acetamide to afford (S)-tert-butyl (1-((2-acetamido-7-(difluoromethyl)-5H-chromeno[3,4-c]pyridin-8-yl)oxy)-4-methylpentan-2-yl)carbamate (130 mg, 0.152 mmol, 12%) yield as an off white solid. LCMS (ESI) m/e 506.2 [(M+H)$^+$, calcd for C$_{26}$H$_{34}$F$_2$N$_3$O$_5$ 506.2]; LC/MS retention time (Method E): t$_R$=2.09 min.

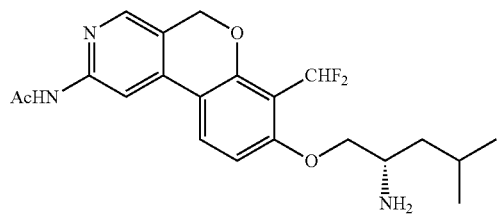 [SMILES: CC(=O)Nc1cc2c(cn1)COc1c-2ccc(OC[C@@H](N)CC(C)C)c1C(F)F]

Part E. (S)—N-(8-(2-amino-4-methylpentyloxy)-7-(difluoromethyl)-5H-chromeno[3,4-d]pyridin-2-yl)acetamide Prepared as described in Example 8, Part D using (S)-tert-butyl (1-((2-acetamido-7-(difluoromethyl)-5H-chromeno[3,4-c]pyridin-8-yl)oxy)-4-methylpentan-2-yl)carbamate (130 mg, 0.152 mmol) to afford (S)—N-(8-(((2-amino-4-methylpentyl)oxy)-7-(difluoromethyl)-5H-chromeno[3,4-c]pyridin-2-yl)acetamide (50 mg, 0.121 mmol, 80% yield) as a white solid. $^1$H NMR (400 MHz, MeOD) δ 8.39 (s, 1H), 8.17 (s, 1H), 7.96 (d, J=8.8 Hz, 1H), 7.19 (t, J=54 Hz, 1H), 6.91 (d, J=8.8 Hz, 1H), 5.19 (s, 2H), 4.15 (m, 1H), 3.92 (m, 1H), 3.27 (m, 1H), 2.22 (s, 3H), 1.81 (m, 1H), 1.44 (m, 2H), 0.99 (m, 6H). LCMS (ESI) m/e 406.2 [(M)$^+$, calcd for C$_{21}$H$_{25}$F$_2$N$_3$O$_3$ 406.2]; LC/MS retention time (Method J): t$_R$=1.87 min; HPLC retention time (method A): t$_R$=9.34 min; HPLC retention time (method B): t$_R$=9.95 min.

Example 39

(S)-4-methyl-1-((2-methyl-5H-chromeno[3,4-c]pyridin-8-yl)oxy)pentan-2-amine

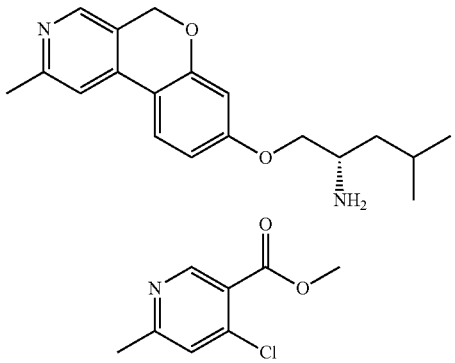

Part A. Methyl 4-chloro-6-methylnicotinate

A solution of methyl 4,6-dichloronicotinate (2.0 g, 9.71 mmol) in 1,4-dioxane (30 mL) and water (1.5 mL), trimethylboroxine (0.731 g, 5.82 mmol), PdCl$_2$(dppf)-CH$_2$Cl$_2$ (0.396 g, 0.485 mmol) and Cs$_2$CO$_3$ (9.49 g, 29.1 mmol) was degassed with argon for 15 min then heated to 110° C. for 16 h. After cooling, the solution was diluted with water (100 mL) and extracted with ethyl acetate (150 mL). The organic layer was dried over Na$_2$SO$_4$ and concentrated under reduced pressure. The residue was purified by silica gel chromatography (20% EtOAc in pet. ether) to afford methyl 4-chloro-6-methylnicotinate (0.1 g, 0.539 mmol, 22% yield) as a yellow oil. LCMS (ESI) m/e 186.0 [(M+H)$^+$, calcd for C$_8$H$_9$ClNO$_2$ 186.02]; LC/MS retention time (Method E): t$_R$=1.75 min. $^1$H NMR (400 MHz, CDCl$_3$) δ 8.94 (s, 1H), 7.27 (s, 1H), 3.95 (s, 3H), 2.58 (s, 3H).

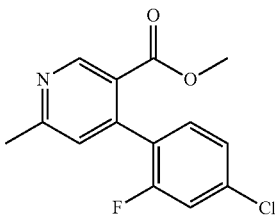 [SMILES: COC(=O)c1cnc(C)cc1-c1ccc(Cl)cc1F]

Part B. Methyl 4-(4-chloro-2-fluorophenyl)-6-methylnicotinate

A mixture of methyl 4-chloro-6-methylnicotinate (0.1 g, 0.539 mmol), (4-chloro-2-fluorophenyl) boronic acid (0.094 g, 0.539 mmol), Pd(PPh$_3$)$_4$ (0.031 g, 0.027 mmol) and Cs$_2$CO$_3$ (0.527 g, 1.616 mmol) in 1,4-dioxane (10 mL) was heated at 80° C. for 16 h. After cooling, the mixture was diluted with water (30 mL) and ethyl acetate (50 mL). The organic phase was collected, dried over Na$_2$SO$_4$ and concentrated under reduced pressure. The residue was purified by silica gel chromatography (20% EtOAc in pet. ether) to afford methyl 4-(4-chloro-2-fluorophenyl)-6-methylnicotinate (0.045 g, 0.161 mmol, 30% yield) as a yellow liquid. LCMS (ESI) m/e 280.0 [(M+H)$^+$, calcd for C$_{14}$H$_{12}$ClFNO$_2$ 280.04]; LC/MS retention time (Method H): t$_R$=2.51 min. $^1$H NMR (400 MHz, CDCl$_3$) δ 7.96 (s, 1H), 7.13-7.29 (m, 3H), 6.44 (s, 1H), 3.94 (s, 3H), 2.49 (s, 3H).

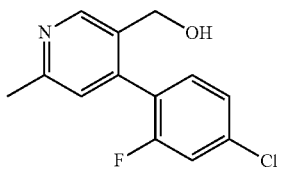 [SMILES: Cc1cc(-c2ccc(Cl)cc2F)c(CO)cn1]

Part C. (4-(4-chloro-2-fluorophenyl)-6-methylpyridin-3-yl)methanol

To a solution of methyl 4-(4-chloro-2-fluorophenyl)-6-methylnicotinate (0.32 g, 1.144 mmol) in tetrahydrofuran (10 mL) at −10° C., LAH (1.716 mL, 1.716 mmol) was added portionwise. The reaction mixture was stirred for 2 h at RT then diluted with saturated aqueous NH$_4$Cl (50 mL). The mixture was extracted with ethyl acetate (80 mL). The organic layer was separated, dried over Na$_2$SO$_4$ and concentrated to afford (4-(4-chloro-2-fluorophenyl)-6-methylpyridin-3-yl) methanol (0.25 g, 0.993 mmol, 87% yield) as off-white solid. LCMS (ESI) m/e 252.0 [(M+H)$^+$, calcd for C$_{13}$H$_{12}$ClFNO 252.0]; LC/MS retention time (Method H): t$_R$=1.60 min; $^1$H NMR (400 MHz, CDCl$_3$) δ 7.69 (s, 1H), 7.52 (s, 1H), 7.23 (s, 2H), 7.04-7.17 (m, 1H), 4.57 (d, J=11.60 Hz, 2H), 2.60 (s, 3H).

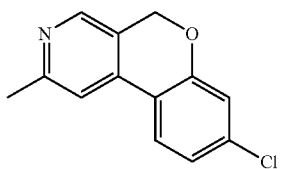 [SMILES: Cc1cc2c(cn1)COc1cc(Cl)ccc1-2]

Part D. 8-chloro-2-methyl-5H-chromeno[3,4-c]pyridine

To a stirred solution of (4-(4-chloro-2-fluorophenyl)-6-methylpyridin-3-yl)methanol (0.25 g, 0.993 mmol) in tetrahydrofuran (25 mL) at 0° C. was added NaH (0.06 g, 1.49 mmol) portionwise. The solution was then stirred for 16 h at RT. The reaction mixture was quenched with water (100 mL). The precipitate was collected by filtration and air dried to afford 8-chloro-2-methyl-5H-chromeno[3,4-c]pyridine (0.2 g, 0.863 mmol, 69% yield) as a white solid. LCMS (ESI) m/e 232.0 [(M+H)$^+$, calcd for C$_{13}$H$_{11}$ClNO 232.0]; LC/MS retention time (Method D): t$_R$=2.06 min; $^1$H NMR (400 MHz, CDCl$_3$) δ 8.31 (s, 1H), 7.65 (d, J=4.40 Hz, 1H), 7.37 (s, 1H), 7.07-7.03 (m, 2H), 5.14 (s, 2H), 2.61 (s, 3H).

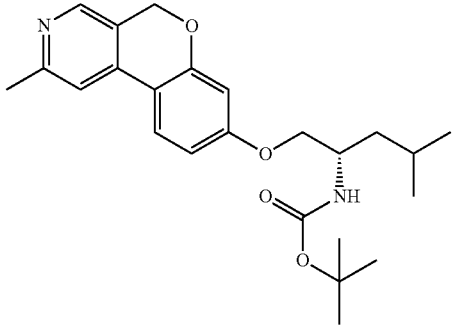 [SMILES: Cc1cc2c(cn1)COc1cc(OC[C@H](CC(C)C)NC(=O)OC(C)(C)C)ccc1-2]

Part E. (S)-Tert-butyl (4-methyl-1-((2-methyl-5H-chromeno[3,4-c]pyridin-8-yl)oxy)pentan-2-yl)carbamate A mixture of 8-chloro-2-methyl-5H-chromeno[3,4-c]pyridine (0.2 g, 0.863 mmol), (S)-tert-butyl (1-hydroxy-4-methylpentan-2-yl)carbamate (0.225 g, 1.036 mmol), palladium (II) acetate (5.81 mg, 0.026 mmol), Cs$_2$CO$_3$ (0.422 g, 1.295 mmol) and 2-di-tert-butylphosphino-2',4',6'-triisopropylbiphenyl (0.022 g, 0.052 mmol) in toluene (5 mL) was heated to 110° C. for 18 h. After cooling, the mixture was filtered through celite and concentrated under reduced pressure. The crude product was purified by silica gel chromatography (70% EtOAc in pet. ether) to afford (S)-tert-butyl (4-methyl-1-((2-methyl-5H-chromeno[3,4-c]pyridin-8-yl)oxy)pentan-2-yl)carbamate, as a semi-solid (0.12 g, 0.291 mmol, 34% yield). LCMS (ESI) m/e 413.4 [(M+H)$^+$, calcd for C$_{24}$H$_{33}$N$_2$O$_4$ 413.2]; LC/MS retention time (Method D): t$_R$=2.42 min.

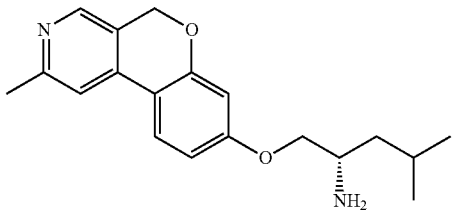 [SMILES: Cc1cc2c(cn1)COc1cc(OC[C@@H](N)CC(C)C)ccc1-2]

Part F. (S)-4-methyl-1-((2-methyl-5H-chromeno[3,4-c]pyridin-8-yl)oxy)pentan-2-amine To a stirred solution of (S)-tert-butyl (4-methyl-1-((2-methyl-5H-chromeno[3,4-c]pyridin-8-yl)oxy)pentan-2-yl)carbamate (0.05 g, 0.121 mmol) in MeOH (2 mL) was added 4N HCl in 1,4-dioxane (0.5 mL, 16.46 mmol). The reaction mixture was stirred for 4 h at RT. The reaction mixture was then concentrated and the residue was dissolved in ethyl acetate (10 mL). The organic layer was washed with saturated NaHCO$_3$ (2×10 mL) and water (20 mL), dried over Na$_2$SO$_4$, filtered and concentrated under reduced pressure to afford a residue which was purified by prep. HPLC (0.1% ammonium acetate in acetonitrile) to afford (S)-4-methyl-1((2-methyl-5H-chromeno[3,4-c]pyridin-8-yl)oxy)pentan-2-amine (0.15 g, 0.048 mmol, 32% yield) as a gummy-solid. $^1$H NMR (400 MHz, CD$_3$OD) δ 8.21 (s, 1H); 7.80 (d, J=8.80 Hz, 1H), 7.55 (s, 1H); 6.74 (d, J=10.80 Hz, 1H), 6.60 (d, J=2.40 Hz, 1H), 5.12 (s, 2H), 4.01-3.96 (m, 1H), 3.84-3.79 (m, 1H), 3.24-3.22 (m, 1H), 2.53 (s, 3H), 1.82-1.79 (m, 1H), 1.42-1.39 (m, 2H), 0.99-0.95 (m, 6H); LCMS (ESI) m/e 312.5 [(M)$^+$, calcd for C$_{19}$H$_{24}$N$_2$O$_2$ 312.2]; LC/MS retention time (Method E): t$_R$=1.63 min; HPLC retention time (method A): t$_R$=7.96 min; HPLC retention time (method B): t$_R$=9.01 min.

Example 40

(R)—N-(8-(2-amino-4-methylpentyloxy)-5H-chromeno[3,4-c]pyridin-2-yl)acetamide

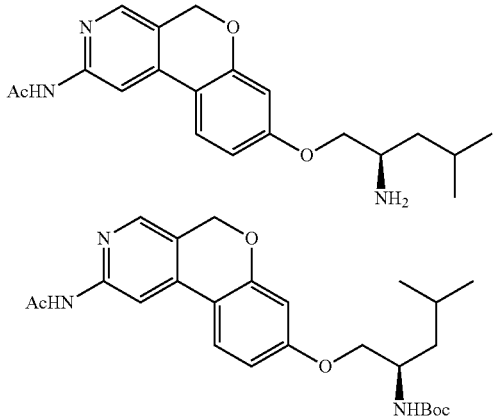

Part A. (R)-tert-butyl 1-(2-acetamido-5H-chromeno[3,4-c]pyridin-8-yloxy)-4-methylpentan-2-ylcarbamate Prepared as described in Example 18, Part H using of N-(8-chloro-5H-chromeno[3,4-c]pyridin-2-yl)acetamide (prepared as described in Example 18, Part G) to afford (R)-tert-butyl (1-((2-acetamido-5H-chromeno[3,4-c]pyridin-8-yl)oxy)-4-methylpentan-2-yl)carbamate (100 mg) as a yellow solid. LCMS (ESI) m/e 456.4 [(M+H)$^+$, calcd for C$_{25}$H$_{34}$N$_3$O$_5$ 456.2]; LC/MS retention time (method E): t$_R$=2.06 min.

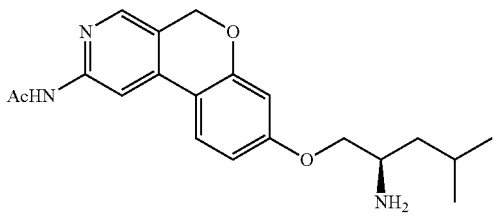 [SMILES: CC(=O)Nc1cc2c(cn1)COc1cc(OC[C@H](N)CC(C)C)ccc1-2]

Part B. (R)—N-(8-(2-amino-4-methylpentyloxy)-5H-chromeno[3,4-c]pyridin-2-yl)acetamide Prepared as described in Example 8, Part D using (R)-tert-butyl (1-((2-acetamido-5H-chromeno[3,4-c]pyridin-8-yl)oxy)-4-methylpentan-2-yl)carbamate to afford (R)—N-(8-((2-amino-4-methylpentyl)oxy)-5H-chromeno[3,4-c]pyridin-2-yl)acetamide (10.44 mg, 0.029 mmol, 47% yield). $^1$H NMR (400 MHz, MeOD) δ 8.25 (s, 1H), 8.15 (s, 1H), 7.83 (d, J=8.8 Hz, 1H), 6.84 (m, 1H), 6.72 (d, J=2.8 Hz, 1H), 5.16 (s, 2H), 4.34 (m, 1H), 4.15 (m, 1H), 3.75 (m, 1H), 2.26 (s, 3H), 1.89-1.65 (m, 3H), 1.15 (m, 6H); LCMS (ESI) m/e 356.2 [(M+H)$^+$, calcd for C$_{20}$H$_{26}$N$_3$O$_3$ 356.2]; LC/MS retention time (method E): t$_R$=1.63 min.

Example 41

(S)—N-(8-((2-amino-4-methylpentyl)oxy)-7-fluoro-5H-chromeno[3,4-c]pyridin-2-yl)acetamide

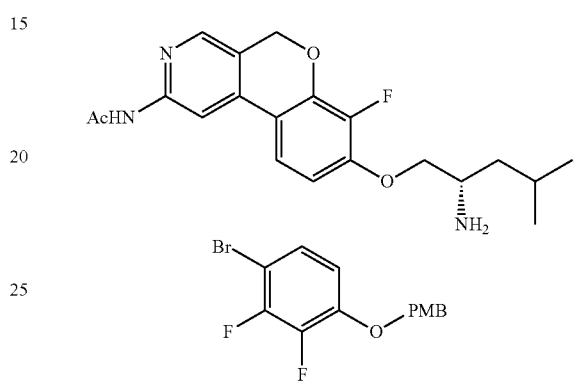

Part A. 1-bromo-2,3-difluoro-4-((4-methoxybenzyl)oxy)benzene

To a stirred solution of 4-bromo-2,3-difluorophenol (5 g, 23.92 mmol) in acetonitrile (50 mL) was added potassium carbonate (3.31 g, 23.92 mmol) at room temperature and the reaction mixture was stirred for 5 min followed by the addition of 1-(chloromethyl)-4-methoxybenzene (3.75 g, 23.92 mmol) dropwise then the reaction mixture was stirred at room temperature for 16 h. After the completion of reaction, the volatiles were removed under reduced pressure. Water (100 mL) was added and the solution extracted with ethyl acetate (2×120 mL). The combined organic layers were washed with brine (100 mL), dried over sodium sulphate, filtered and concentrated under reduced pressure to afford 1-bromo-2,3-difluoro-4-((4-methoxybenzyl)oxy)benzene (7.58 g, 23.03 mmol, 96% yield) as a pale brown solid. The product was carried on without further purification. LCMS (ESI) m/e 329.1 [(M)$^-$, calcd for C$_{14}$H$_{10}$BrF$_2$O$_2$ 329.0]; LC/MS retention time (Method G): t$_R$=1.20 min.

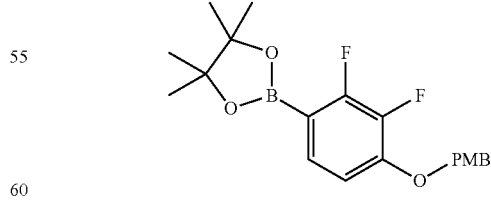

Part B. 2-(2,3-difluoro-4-((4-methoxybenzyl)oxy)phenyl)-4,4,5,5-tetramethyl-1,3,2-dioxaborolane Prepared as described in Example 37, Part C using 1-bromo-2,3-difluoro-4-((4-methoxybenzyl)oxy)benzene to afford 2-(2,3-difluoro-4-((4-methoxybenzyl)oxy)phenyl)-4,4,5,5-tetramethyl-1,3,2-dioxaborolane (3.52 g, 9.36 mmol, 77% yield) as a pale yellow solid. $^1$H NMR (400 MHz, CDCl$_3$) δ 7.35 (m, 3H), 6.90 (m, 2H), 6.76 (m, 1H), 5.09 (s, 2H), 3.80 (s, 3H), 1.34 (s, 12H).

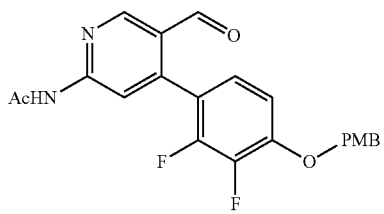

Part C. N-(4-(2,3-difluoro-4-((4-methoxybenzyl)oxy)phenyl)-5-formylpyridin-2-yl)acetamide Prepared as described in Example 5, Part B using 2-(2,3-difluoro-4-((4-methoxybenzyl)oxy)phenyl)-4,4,5,5-tetramethyl-1,3,2-dioxaborolane to afford N-(4-(2,3-difluoro-4-((4-methoxybenzyl)oxy)phenyl)-5-formylpyridin-2-yl)acetamide (1.85 g, 4.49 mmol, 48% yield) as a white solid. LCMS (ESI) m/e 413.2 [(M+H)$^+$, calcd for C$_{22}$H$_{19}$F$_2$N$_2$O$_4$ 413.1]; LC/MS retention time (Method E): t$_R$=1.99 min.

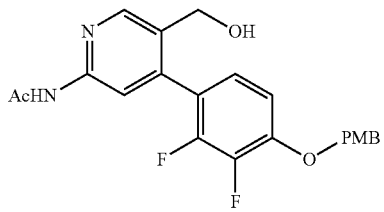

Part D. N-(4-(2,3-difluoro-4-(((4-methoxybenzyl)oxy)phenyl)-5-(hydroxymethyl)pyridin-2-yl)acetamide Prepared as described in Example 37, Part E using N-(4-(2,3-difluoro-4-((4-methoxybenzyl)oxy)phenyl)-5-formylpyridin-2-yl)acetamide to afford N-(4-(2,3-difluoro-4-((4-methoxybenzyl)oxy)phenyl)-5-(hydroxymethyl)pyridin-2-yl)acetamide (2.1 g, 3.29 mmol, 75% yield) as a pale brown solid. LCMS (ESI) m/e 415.2 [(M+H)$^+$, calcd for C$_{22}$H$_{21}$F$_2$N$_2$O$_4$ 415.1]; LC/MS retention time (Method G): t$_R$=0.9 min.

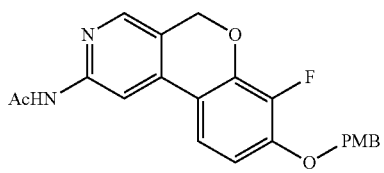

Part E. N-(7-fluoro-8-((4-methoxybenzyl)oxy)-5H-chromeno[3,4-d]pyridin-2-yl)acetamide Prepared as described in Example 5, Part D using N-(4-(2,3-difluoro-4-((4-methoxybenzyl)oxy)phenyl)-5-(hydroxymethyl)pyridin-2-yl)acetamide to afford N-(7-fluoro-8-((4-methoxybenzyl)oxy)-5H-chromeno[3,4-c]pyridin-2-yl)acetamide (750 mg, 1.613 mmol, 85% yield) as an off-white solid. LCMS (ESI) m/e 395.2 [(M+H)$^+$, calcd for C$_{22}$H$_{20}$FN$_2$O$_4$ 395.1]; LC/MS retention time (Method E): t$_R$=1.95 min.

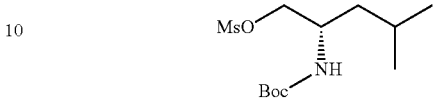

Part F. (S)-2-((tert-butoxycarbonyl)amino)-4-methylpentyl methanesulfonate

To a stirred solution of (S)-tert-butyl (1-hydroxy-4-methylpentan-2-yl)carbamate (1.6 g, 7.36 mmol) in dichloromethane (15 mL) was added triethyl amine (2.052 mL, 14.73 mmol) at 0° C. and the solution was stirred for 5 min. To this mixture at 0° C. was added methanesulfonyl chloride (0.574 mL, 7.36 mmol) dropwise and the reaction mixture was stirred at room temperature for 1 h. The reaction was quenched with water (15 mL) and extracted with DCM (2×15 mL). The combined organic layers were washed with brine (10 mL), dried over sodium sulphate, concentrated under reduced pressure to yield (S)-2-((tert-butoxycarbonyl)amino)-4-methylpentyl methanesulfonate (1.7 g, 5.75 mmol, 78% yield) as a yellow solid which was carried on without further purification. $^1$H NMR (400 MHz, CDCl$_3$) δ 4.55 (m, 1H), 4.25 (m, 1H), 4.16 (m, 1H), 3.92 (m, 1H), 3.05 (s, 3H), 1.66 (m, 2H), 1.56 (m, 10H), 0.92 (m, 6H).

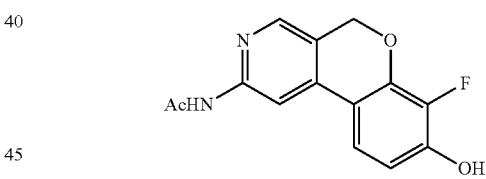

Part G. N-(7-fluoro-8-hydroxy-5H-chromeno[3,4-c]pyridin-2-yl)acetamide

To a stirred solution of N-(7-fluoro-8-((4-methoxybenzyl)oxy)-5H-chromeno[3,4-c]pyridin-2-yl)acetamide (150 mg, 0.380 mmol) in dichloromethane (5 mL) was added TFA (0.059 mL, 0.761 mmol) at room temperature and the reaction mixture was stirred at rt for 2 h. After the completion of reaction the volatiles were removed under reduced pressure. The residue was washed with diethyl ether (7 mL) and stirred for 5 min. The solid was collected by vacuum filtration and dried under vacuum to yield N-(7-fluoro-8-hydroxy-5H-chromeno[3,4-c]pyridin-2-yl)acetamide, TFA (70 mg, 0.170 mmol, 45% yield) as a white solid. LCMS (ESI) m/e 275.0 [(M+H)$^+$, calcd for C$_{14}$H$_{12}$FN$_2$O$_3$ 275.1]; LC/MS retention time (Method E): t$_R$=2.0 min.

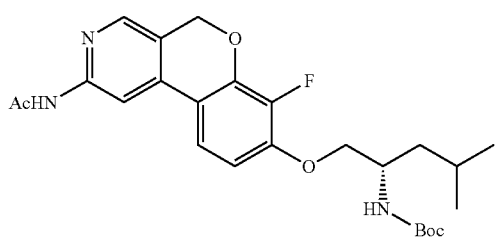 [SMILES: CC(=O)Nc1cc2c(cn1)COc1c-2ccc(OC[C@H](CC(C)C)NC(=O)OC(C)(C)C)c1F]

Part H. (S)-tert-butyl (1-((2-acetamido-7-fluoro-5H-chromeno[3,4-c]pyridin-8-yl)oxy)-4-methylpentan-2-yl)carbamate To a stirred solution of N-(7-fluoro-8-hydroxy-5H-chromeno[3,4-c]pyridin-2-yl)acetamide, TFA (70 mg, 0.170 mmol) and potassium carbonate (97 mg, 0.704 mmol) in DMF (4 mL) was added (S)-2-((tert-butoxycarbonyl)amino)-4-methylpentyl methanesulfonate (52.0 mg, 0.176 mmol) at room temperature and the reaction mixture was heated to 90° C. for 1 h. After completion of reaction, the volatiles were removed under reduced pressure to afford a brown residue. To this residue water (15 mL) was added and the solution extracted with ethyl acetate (2×20 mL). The combined organic layers were washed with water (30 mL), brine (20 mL), dried over sodium sulphate and concentrated under reduced pressure to afford (S)-tert-butyl (1-((2-acetamido-7-fluoro-5H-chromeno[3,4-c]pyridin-8-yl)oxy)-4-methylpentan-2-yl)carbamate (90 mg, 0.066 mmol, 37% yield) as a brown oil. The product was carried forward without further purification. LCMS (ESI) m/e 472.2 [(M−H)−, calcd for $C_{25}H_{31}FN_3O_5$ 472.2]; LC/MS retention time (Method E): $t_R$=1.99 min.

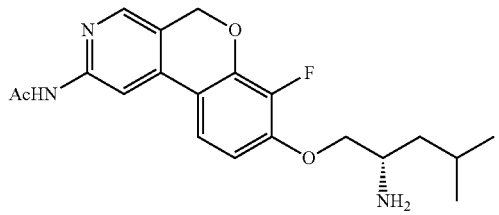

Part I. (S)—N-(8-((2-amino-4-methylpentyl)oxy)-7-fluoro-5H-chromeno[3,4-c]pyridin-2-yl)acetamide Prepared as described in Example 37, Part H using (S)-tert-butyl (1-((2-acetamido-7-fluoro-5H-chromeno[3,4-c]pyridin-8-yl)oxy)-4-methylpentan-2-yl)carbamate to afford (S)—N-(8-((2-amino-4-methylpentyl)oxy)-7-fluoro-5H-chromeno[3,4-c]pyridin-2-yl)acetamide, 0.5 TFA (16 mg, 0.037 mmol, 19% yield) as white solid. $^1$H NMR (400 MHz, MeOD) δ 8.42 (s, 1H), 8.19 (s, 1H), 7.65-7.62 (m, 1H), 6.97-6.93 (m, 1H), 5.2 (s, 2H), 4.30 (m, 1H), 4.27-4.10 (m, 1H), 3.59-3.51 (m, 1H), 2.23 (s, 3H), 1.79 (m, 1H), 1.66-1.56 (m, 2H), 1.21 (m, 6H); LCMS (ESI) m/e 372.2 [(M−H)−, calcd for $C_{20}H_{23}FN_3O_3$ 372.2]; LC/MS retention time (Method E): $t_R$=2.01 min; HPLC retention time (method A): $t_R$=9.04 min; HPLC retention time (method B): $t_R$=9.89 min.

Example 42

(S)—N-(8-(2-amino-4-methylpentyloxy)-5H-chromeno[3,4-d]pyridin-2-yl)cyclopropanecarboxamide

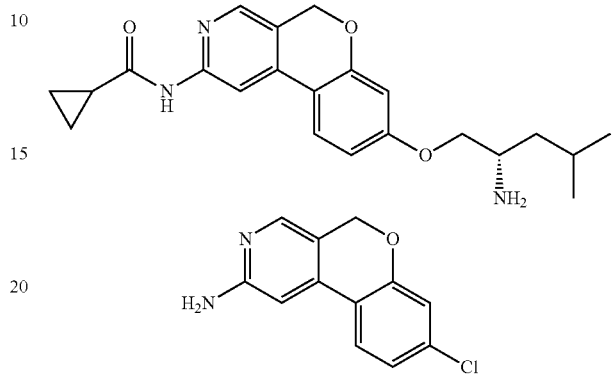

Part A. 8-chloro-5H-chromeno[3,4-c]pyridin-2-amine

N-(8-chloro-5H-chromeno[3,4-c]pyridin-2-yl)acetamide (0.05 g, 0.182 mmol) was taken up in 50% aqueous HCl (3 mL, 99 mmol) and refluxed for 3 h. The reaction mixture was cooled to room temperature and the volatiles were evaporated under reduced pressure. The residue was treated with water (3 mL) and extracted with dichloromethane (2×6 mL). The aqueous layer was collected and concentrated under reduced pressure to afford a 8-chloro-5H-chromeno[3,4-c]pyridin-2-amine, hydrochloride (50 mg, 0.185 mmol, quantitatively) as a yellow oil. LCMS (ESI) m/e 233.3 [(M+H)+, calcd for $C_{12}H_{10}ClN_2O$ 233.0]; LC/MS retention time (method G); $t_R$=0.89 min

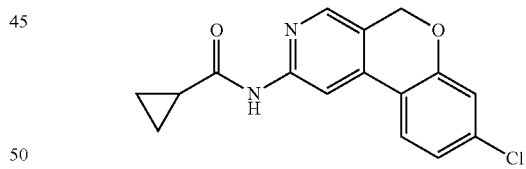

Part B. N-(8-chloro-5H-chromeno[3,4-c]pyridin-2-yl)cyclopropanecarboxamide

To a stirred solution of 8-chloro-5H-chromeno[3,4-c]pyridin-2-amine, HCl (0.05 g, 0.186 mmol) in chloroform (2 mL) was added pyridine (0.090 mL, 1.115 mmol) followed by addition of cyclopropanecarbonyl chloride (0.034 mL, 0.372 mmol) and DMAP (2.270 mg, 0.019 mmol) under nitrogen atmosphere. The reaction mixture was allowed to stir at room temperature for 12 h. The mixture was diluted with water (6 mL) then extracted with dichloromethane (2×10 mL). The combined organic layers were dried over sodium sulfate and concentrated under reduced pressure. The residue was puri fied by reverse phase HPLC (10 mM ammonium acetate in acetonitrile and water) to afford N-(8-chloro-5H-chromeno[3,4-c]pyridin-2-yl)cyclopropanecarboxamide (0.048 g, 0.156 mmol, 84% yield) as a white solid. LCMS (ESI) m/e 301.0 [(M+H)$^+$, calcd for $C_{16}H_{14}ClN_2O_2$ 301.1]; LC/MS retention time (method E): $t_R$=2.53 min.

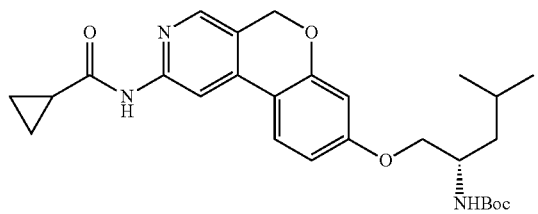 [SMILES: CC(C)C[C@@H](COc1ccc2c(c1)OCc1cnc(NC(=O)C3CC3)cc1-2)NC(=O)OC(C)(C)C]

Part C. (S)-tert-butyl 1-(2-(cyclopropanecarboxamido)-5H-chromeno[3,4-c]pyridin-8-yloxy)-4-methylpentan-2-ylcarbamate Prepared as described in Example 18, Part H using N-(8-chloro-5H-chromeno[3,4-c]pyridin-2-yl)cyclopropanecarboxamide (0.166 g, 0.442 mmol) to afford (S)-tert-butyl 1-(2-(cyclopropanecarboxamido)-5H-chromeno[3,4-c]pyridin-8-yloxy)-4-methylpentan-2-ylcarbamate (200 mg, 0.415 mmol, 55% yield). LCMS (ESI) m/e 482.2 [(M+H)$^+$, calcd for $C_{27}H_{36}N_3O_5$ 482.2]; LC/MS retention time (method F): $t_R$=0.92 min.

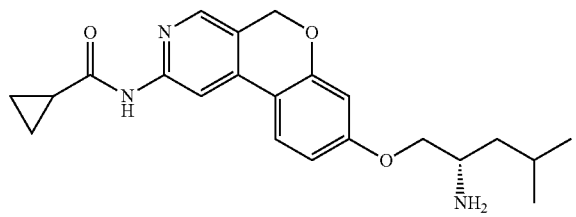 [SMILES: CC(C)C[C@H](N)COc1ccc2c(c1)OCc1cnc(NC(=O)C3CC3)cc1-2]

Part D. (S)—N-(8-(2-amino-4-methylpentyloxy)-5H-chromeno[3,4-d]pyridin-2-yl)cyclopropanecarboxamide Prepared as described in Example 8, Part D using (S)-tert-butyl (1-((2-(cyclopropanecarboxamido)-5H-chromeno[3,4-c]pyridin-8-yl)oxy)-4-methylpentan-2-yl)carbamate (0.2 g, 0.241 mmol) to afford (S)—N-(8-(2-amino-4-methylpentyloxy)-5H-chromeno[3,4-c]pyridin-2-yl)cyclopropanecarboxamide (14 mg, 0.036 mmol, 15% yield) as a white solid. LCMS (ESI) m/e 382.3 [(M+H)$^+$, calcd for $C_{22}H_{28}N_3O_3$ 382.2]; LC/MS retention time (Method J): $t_R$=1.96 min; HPLC retention time (method A): $t_R$=10.17 min; HPLC retention time (method B): $t_R$=5.69 min. $^1$H NMR (400 MHz, MeOD) δ 8.33 (s, 1H), 8.12 (s, 1H), 7.8 (m, 1H), 6.77 (m, 1H), 6.64 (s, 1H), 5.12 (s, 2H), 4.12 (m, 1H), 3.96 (m, 1H), 3.44 (m, 1H), 1.93 (m, 1H), 1.90 (m, 1H), 1.51 (m, 2H), 1.01 (m, 8H), 0.93 (m, 2H).

Example 43

(S)-methyl 8-(2-amino-4-methylpentyloxy)-5H-chromeno[3,4-c]pyridin-2-ylcarbamate

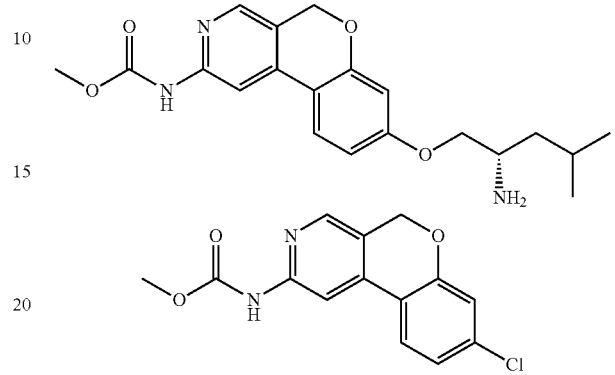

Part A. methyl 8-chloro-5H-chromeno[3,4-d]pyridin-2-ylcarbamate

Prepared as described in Example 42, Part B using 8-chloro-5H-chromeno[3,4-c]pyridin-2-amine (0.1 g, 0.301 mmol) (prepared as in Example 18, Part G) to afford crude which was purified by reverse phase HPLC (10 mM ammonium acetate in acetonitrile and water) to afford methyl (8-chloro-5H-chromeno[3,4-c]pyridin-2-yl)carbamate (0.011 g, 0.036 mmol, 12% yield) as a white solid. LCMS (ESI) m/e 291.0 [(M+H)$^+$, calcd for $C_{14}H_{12}ClN_2O_3$ 291] LC/MS retention time (method E): $t_R$=1.96 min; $^1$H NMR (400 MHz, DMSO-d$_6$) δ 10.3 (s, 1H), 8.23 (s, 1H), 8.22 (s, 1H), 7.83 (d, J=8.8 Hz, 1H), 7.21 (m, 1H), 7.17 (s, 1H), 5.20 (s, 2H), 3.72 (s, 3H).

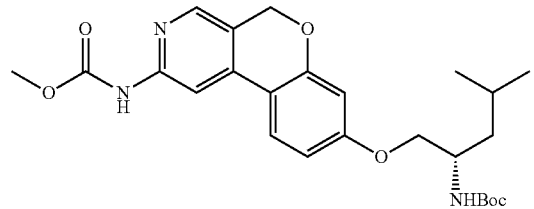 [SMILES: COC(=O)Nc1cc2c(cn1)COc1cc(OC[C@H](CC(C)C)NC(=O)OC(C)(C)C)ccc1-2]

Part B. methyl (S)-(8-((2-((tert-butoxycarbonyl)amino)-4-methylpentyl)oxy)-5H-chromeno[3,4-d]pyridin-2-yl)carbamate Prepared as described in Example 18, Part H using methyl (8-chloro-5H-chromeno[3,4-c]pyridin-2-yl)carbamate (0.16 g, 0.176 mmol) to afford crude material which was purified by using silica gel chromatography (2.5% methanol in chloroform) to afford methyl (S)-(8-(2-((tert-butoxycarbonyl)amino)-4-methylpentyl)oxy)-5H-chromeno[3,4-c]pyridin-2-yl)carbamate (0.15 g, 0.067 mmol, 38% yield) as a yellow oil. LCMS (ESI) m/e 472.2 [(M+H)+, calcd for C$_{25}$H$_{34}$N$_3$O$_6$ 472.2]; LC/MS retention time (method F): t$_R$=0.95 min.

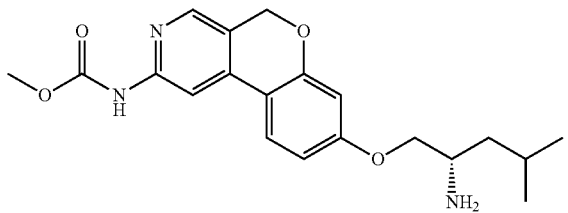 [SMILES: COC(=O)Nc1cc2c(cn1)COc1cc(OC[C@@H](N)CC(C)C)ccc1-2]

Part C. (S)-methyl 8-(2-amino-4-methylpentyloxy)-5H-chromeno[3,4-c]pyridin-2-ylcarbamate Prepared as described in Example 8, Part D using (S)-(8-(2-((tert-butoxycarbonyl)amino)-4-methylpentyl)oxy)-5H-chromeno[3,4-c]pyridin-2-yl)carbamate (0.15 g, 0.067 mmol) to afford crude material which was purified by reverse phase HPLC (10 mM ammonium acetate in acetonitrile and water) to afford (S)-methyl (8-((2-amino-4-methylpentyl)oxy)-5H-chromeno[3,4-c]pyridin-2-yl)carbamate (5 mg, 0.013 mmol, 19% yield) as a white solid. $^1$H NMR (400 MHz, MeOD) δ 8.14 (s, 1H), 8.06 (d, J=0.8 Hz, 1H), 7.78 (d, J=8.8 Hz, 1H), 6.77 (m, 1H), 6.62 (d, J=2.4 Hz, 1H), 5.11 (s, 2H), 4.04 (m, 1H), 3.86 (m, 1H), 3.82 (s, 3H), 3.32 (m, 1H), 1.86 (m, 1H), 1.42 (m, 2H), 0.99 (m, 6H); LCMS (ESI) m/e 372.2 [(M+H)+, calcd for C$_{20}$H$_{26}$N$_3$O$_4$ 372.2]; LC/MS retention time (method E): t$_R$=2.13 min; HPLC retention time (method A): t$_R$=9.39 min; HPLC retention time (method B): t$_R$=10.15 min.

Example 44

N-(8-(2-amino-2,4-dimethylpentyloxy)-5H-chromeno[3,4-c]pyridin-2-yl)acetamide

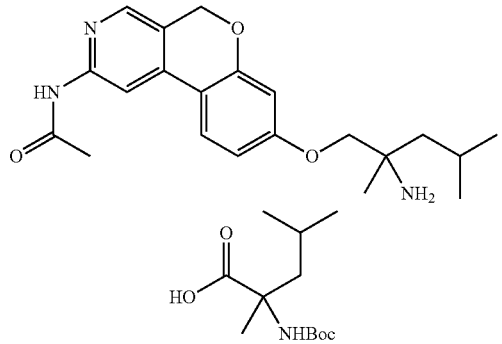

Part A.
2-(tert-butoxycarbonylamino)-2,4-dimethylpentanoic acid

To a stirred solution of 2-amino-2,4-dimethylpentanoic acid (1 g, 6.89 mmol) in tetrahydrofuran (15 mL) and water (15 mL) was added K$_2$CO$_3$ (3.81 g, 27.5 mmol) and the reaction mixture was stirred at room temperature for 10 min. To the resultant mixture (BOC)$_2$O (3.20 mL, 13.77 mmol) was added dropwise and the reaction mixture was allowed to stir at room temperature for 14 h. The reaction mixture was then concentrated under reduced pressure. The aqueous layer was washed with ethyl acetate (3×15 mL) and acidified with a saturated aqueous solution of citric acid (25 mL) then extracted with ethyl acetate (3×50 mL). The combined organic extracts were washed with water (2×15 mL), brine (20 mL), dried over sodium sulfate and concentrated under reduced pressure to afford 2-((tert-butoxycarbonyl)amino)-2,4-dimethylpentanoic acid (1.6 g, 6.89 mmol, quantitative yield) as a white solid. $^1$H NMR (400 MHz, CDCl$_3$) δ 5.36 (bs, 1H), 2.10 (m, 1H), 1.77 (m, 2H), 1.74-1.65 (m, 3H), 1.59 (s, 9H), 0.89 (m, 3H), 0.94 (m, 3H).

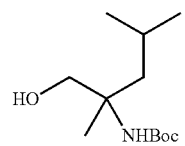

Part B. tert-butyl
1-hydroxy-2,4-dimethylpentan-2-ylcarbamate

To a stirred solution of 2-((tert-butoxycarbonyl)amino)-2,4-dimethylpentanoic acid (1.6 g, 6.52 mmol) in tetrahydrofuran (40 mL) cooled to −10° C. under nitrogen atmosphere was added N-methylmorpholine (0.860 mL, 7.83 mmol) followed by isobutyl chloroformate (1.028 mL, 7.83 mmol) dropwise and the reaction mixture was stirred for 30 min. The reaction mixture was then filtered and the filtrate was added dropwise to a suspension of NaBH$_4$ (0.494 g, 13.04 mmol) in water (20.0 mL). The reaction mixture was stirred for 10 min then diluted with ethyl acetate (30 mL). The organic layer was separated and washed with brine (2×20 mL), dried over (Na$_2$SO$_4$) and evaporated under reduced pressure. The residue was purified by silica gel chromatography (30% ethyl acetate and pet ether) to afford tert-butyl (1-hydroxy-2,4-dimethylpentan-2-yl)carbamate (1.1 g, 4.76 mmol, 73% yield) as an oil. $^1$H NMR (400 MHz, DMSO-d$_6$) δ 6.09 (s, 1H), 4.61 (t, J=7.6 Hz, 1H), 3.35 (m, 2H), 1.8-1.6 (m, 2H), 1.44-1.35 (m, 10H), 1.09 (s, 3H), 0.86 (m, 6H).

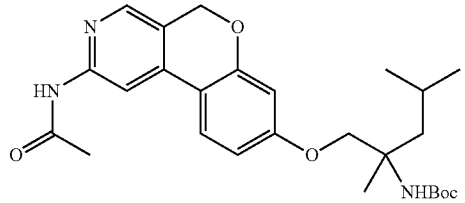 [SMILES: CC(=O)Nc1cc2c(cn1)COc1cc(OCC(C)(CC(C)C)NC(=O)OC(C)(C)C)ccc1-2]

Part C. tert-butyl 1-(2-acetamido-5H-chromeno[3,4-c]pyridin-8-yloxy)-2,4-dimethylpentan-2-ylcarbamate Prepared as described in Example 18, Part H using N-(8-chloro-5H-chromeno[3,4-c]pyridin-2-yl)acetamide (0.3 g, 1.092 mmol) (prepared as in Example 18, Part G) to afford crude material which was purified by reverse phase HPLC (10 mM ammonium acetate) to afford racemic tert-butyl (1-((2-acetamido-5H-chromeno[3,4-c]pyridin-8-yl)oxy)-2,4-dimethylpentan-2-yl)carbamate (60 mg, 0.116 mmol, 12% yield) as a yellow semi solid. $^1$H NMR (400 MHz, MeOD) δ 9.33 (s, 1H), 8.11 (s, 1H), 7.74 (d, J=8.8 Hz, 1H), 6.74 (m, 1H), 6.58 (d, J=2.4 Hz, 1H), 5.11 (s, 2H), 4.18 (d, J=9.2 Hz, 1H), 3.97 (d, J=9.2 Hz, 1H), 2.21 (s, 3H), 1.87 (m, 2H), 1.62 (m, 1H), 1.42 (s, 9H), 1.36 (s, 3H), 0.99 (m, 6H); LCMS (ESI) m/e 470 [(M+H)$^+$, calcd for $C_{26}H_{36}N_3O_5$ 470.25]; LC/MS retention time (Method K): $t_R$=2.48 min.

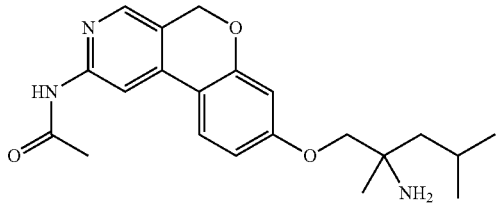 [SMILES: CC(=O)Nc1cc2c(cn1)COc1cc(OCC(C)(N)CC(C)C)ccc1-2]

Part D. N-(8-(2-amino-2,4-dimethylpentyloxy)-5H-chromeno[3,4-d]pyridin-2-yl)acetamide Prepared as described in Example 8, Part D using tert-butyl (1-((2-acetamido-5H-chromeno[3,4-c]pyridin-8-yl)oxy)-2,4-dimethylpentan-2-yl)carbamate (0.55 g, 0.433 mmol) to afford crude material which was purified by reverse phase HPLC (10 mM ammonium acetate in acetonitrile and water) to afford N-(8-(2-amino-2,4-dimethylpentyloxy)-5H-chromeno[3,4-c]pyridin-2-yl)acetamide. To make the HCl salt, the compound was dissolved in methanol (1 mL), cooled to 0° C. and treated with 4M HCl in dioxane (1.5 mL) and stirred for 10 min. The volatiles were concentrated under reduced pressure and the solution was lyophilized to afford racemic N-(8-(((2-amino-2,4-dimethylpentyl)oxy)-5H-chromeno[3,4-c]pyridin-2-yl)acetamide, HCl (0.013 g, 0.030 mmol, 7% yield) as a pale yellow solid. $^1$H NMR (400 MHz, MeOD) δ 8.21 (s, 1H), 7.94 (d, J=8.8 Hz, 1H), 7.86 (bs, 1H), 6.94 (m, 1H), 6.79 (s, 1H), 5.25 (s, 2H), 4.29 (d, J=10.4 Hz, 1H), 4.16 (d, J=10.4 Hz, 1H), 2.33 (s, 3H), 1.88 (m, 2H), 1.72 (m, 1H), 1.52 (s, 3H), 1.06 (m, 6H); LCMS (ESI) m/e 370.4 [(M+H)$^+$, calcd for $C_{21}H_{28}N_3O_3$ 370.2]; LC/MS retention time (Method J); HPLC retention time (method A): $t_R$=9.51 min; HPLC retention time (method B): $t_R$=9.98 min.

Methods

AAK1 Kinase Assay

The assays were performed in U-bottom 384-well plates. The final assay volume was 30 μl prepared from 15 μl additions of enzyme and substrates (fluoresceinated peptide (5-FAM)-Aha-KEEQSQITSQVTGQIGWR-NH2 and ATP) and test compounds in assay buffer (10 mM Tris-HCL pH 7.4, 10 mM MgCl$_2$, 0.01% Tween-20 and 1.0 mM DTT). The reactions were initiated by the combination of bacterially expressed, GST-Xa-hAAK1 with substrates and test compounds. The reactions were incubated at room temperature for 3 hours and terminated by adding 60 μl of 35 mM EDTA buffer to each sample. The reactions were analyzed on the Caliper LabChip 3000 (Caliper, Hopkinton, Mass.) by electrophoretic separation of the fluorescent substrate and phosphorylated product. Inhibition data were calculated by comparison to EDTA quenched control reactions for 100% inhibition and vehicle-only reactions for 0% inhibition. The final concentration of reagents in the assays are ATP, 22 μM; (5-FAM)-Aha-KEEQSQITSQVTGQIGWR-NH2, 1.5 μM; GST-Xa-hAAK1, 3.5 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis.

HEK281 Cell-Based Assay

HEK293F cells were cultured in media containing DMEM (Gibco, cat. #11965). 10% FBS (SAFC Biosciences, cat.#12103C), 1×GPS (glutamine, penicillin and streptomycin). On day one, cells were plated on a 10 cm dish so that they are ~80% confluent at time of transfection. Roughly 12 million cells were in a 10 cm dish at time of transfection. On day two, each dish was transfected with 48 ug DNA and 144 ul Lipofectamine 2000 (Invitrogen, cat.#11668-019). The DNA was comprised of a mixture (per 10 cm dish) containing 3 ug AAK1/HA/pIRES (full length human, NCBI accession no. NP 055726.2), 45 μg Flag/AP2MI/pcDNA (full length human), and 1.5 ml OPTI-MEM. The Lipofectamine 2000 is made up of a mixture (per 10 cm dish) containing 144 μl Lipofectamine 2000 and 1.5 ml OPTI-MEM. Each mixture was transferred to individual 15 ml tubes and incubated at RT for 5 minutes, and then the two mixes were combined and incubated at RT for 20 minutes. Growth media was then aspirated from each 10 cm plate and replaced with 10 ml of DMEM+10% FBS (no GPS). Finally, 3 ml DNA/Lipofectamine mix was added to each 10 cm dish and mix gently followed by incubate of plate overnight at 37° C. and 5% CO$_2$.

On day three, compounds were diluted in 100% DMSO at 1000× final concentration, followed by 3-fold serial dilutions for a total of 5 concentrations tested. Four compounds were tested per 10 cm dish. One ul of each compound dilution was then pipetted into a deep-well, 96-well plate, followed by addition of 500 μl DMEM+0.5% FBS into each well for a 2× final concentration of each compound. Cells were resuspended in a 10 cm dish by simple pipetting (HEK293 cells come off the plate that easy at this point) and then transferred to a 50 ml conical tube and pelleted by centrifugation at 1000 rpm for 5 min. Cell pellets were then resuspended in 2.75 ml DMEM+0.5% FBS per 10 cm dish and 100 μA of cell suspension transferred into each well of 96-well TC plate. Finally, 100 μA of 2× compound diluted in DMEM+0.5% FBS was then added into wells containing cell suspension for a 1× final concentration. Plates were then incubated at 37° C. and 5% CO$_2$ for 3 hours followed by transferring of cell suspensions from each well into 12-tube PCR strips. The PCR strips were spun in a tip rack at 1000 rpm for 5 minutes to pellet cells and media was then removed by pipetting without disturbing the cell pellet.

To prepare for Western Blot analysis, cell pellets were resuspend in 40 ul 1× LDS-PAGE sample buffer (Invitrogen, cat.#NP0008)+2× Halt phophatase and protease inhibitor cocktail (Thermo Scientific, cat.#1861284), followed by sonicating each with microtip sonicator set at 5 for 8-10 seconds. Five ul of 10× NuPage Sample Reducing Agent (with 50 mM DTT) was to each sample followed by heat denaturing at 70 C for 10 min on PCR machine. A total of 10 μl per sample was loaded into each lane of a 4-20% Tris-Glycine Criterion 26-well gel (Biorad, cat.#345-0034) for the phospho-mu2 blot and 10 μl per lane in a 4-12% Bis-Tris (+MES buffer) NuPAGE 26-well gel (Invitrogen, cat.#WG1403BX10) for the mu2 blot. For controls, 2 ng of phospho-mu2 or 20 ng mu2/Flag proteins were loaded in the last well of each gel. After SDS-PAGE, samples on each gel were transferred to PVDF membrane using an iBlot and membranes were blocked for one hour in TBST+5% milk, followed by wash 3× for 5-10 min with TBST. Criterion gels were probed with rabbit anti-phospho-mu2 (1:5000; a rabbit polyclonal antibody produced by New England Peptide and affinity purified at Lexicon) in TBST+5% BSA, whereas, NuPAGE gels were probed with mouse anti-Flag (1:500;

Sigma, cat.#F1804) in TBST+5% milk, and these primary antibodies were incubated overnight at 4° C. on a rocker.

On day four, Western blots were washed 3× for 5-10 minutes with TBST, probe with anti-rabbit-HRP (1:2000; Bio-Rad, cat.#170-6515) or anti-mouse-HRP (1:2000; Biorad, cat.#170-6516) in TBST+5% milk for 1 hour at RT, washed 3× for 10 minutes with TBST, and developed with ECL reagent (GE Healthcare, cat.#RPN2132) on a Versadoc. Finally, the camera was set up to take a picture every 30 seconds for 10 minutes and the best image saved for each blot with no saturated signal (when the signal is saturated, the bands will be highlighted red). A volume analysis on each band was performed to obtain density values. Percent inhibition was calculated for each sample by first normalizing to total Mu2 expression levels and then comparing to 0% and 100% controls. $IC_{50}$ values were then calculated using Excel fitting software.

AAK1 Knockout Mice

Mice homozygous (−/−) for the disruption of the AAK1 gene were prepared by two methods; gene trapping and homologous recombination.

Gene trapping is a method of random insertional mutagenesis that uses a fragment of DNA coding for a reporter or selectable marker gene as a mutagen. Gene trap vectors have been designed to integrate into introns or genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells from derived murine strain A129), were mutated by a process involving the insertion of at least a portion of a genetically engineered vector sequence into the gene of interest, the mutated embryonic stem cells were microinjected into blastocysts which were subsequently introduced into pseudopregnant female hosts and carried to term using established methods. See, e.g., "Mouse Mutagenesis", 1998, Zambrowicz et al., eds., Lexicon Press, The Woodlands, Tex. The resulting chimeric animals were subsequently bred to produce offspring capable of germline transmission of an allele containing the engineered mutation in the gene of interest.

AAK1-gene disrupted mice were also made by homologous recombination. In this case, the second coding exon of the murine AAK1 gene (see GenBank Accession Number NM_177762) was removed by methods known in the art. See, e.g., U.S. Pat. Nos. 5,487,992, 5,627,059, and 5,789,215.

Mice homozygous (−/−) for the disruption of the AAK1 gene were studied in conjunction with mice heterozygous (+/−) for the disruption of the AAK1 gene, and wild-type (+/+) litter mates. During this analysis, the mice were subject to a medical work-up using an integrated suite of medical diagnostic procedures designed to assess the function of the major organ systems in a mammalian subject. Homozygous (−/−) "knockout" mice were studied in conjunction with their heterozygous (+/−) and wild-type (+/+) litter mates. Disruption of the AAK1 gene was confirmed by Southern analysis. Expression of the murine homolog of AAK1 was detected by RT-PCR in murine brain; spinal cord; eye; thymus; spleen; lung; kidney; liver; skeletal muscle; bone; stomach, small intestine and colon; heart; adipose; asthmatic lung; LPS liver; blood; banded heart; aortic tree; prostate; and mammary gland (5 week virgin, mature virgin, 12 DPC, 3 day post-partum (lactating), 3 day post-weaning (early involution), and 7 day post-weaning (late involution)).

AAK1 homozygous (−/−) and their wild-type (+/+) littermates were tested using the formalin paw test in order to assess their acute and tonic nociceptive responses. For these tests, Automatic Nociception Analyzers (purchased from the Ozaki lab at University of California, San Diego) were used. A metal band was placed around the left hind paw of each mouse 30 minutes prior to testing. After the 30-minute acclimation period, 20 μl of 5% formalin is subcutaneously injected in the dorsal surface of the left hind paw. Mice were individually housed in cylindrical chambers for 45 minutes. Fresh 5% formalin solution was prepared by diluting formaldehyde (Formalde-fresh 20%, Fisher Scientific, Fair Lawn, N.J.) with distilled water. Investigatory compounds were administered 30 minutes prior to formalin injection.

A computer recorded flinches per minute, total flinches for phase I (acute phase=first 8 minutes), and total flinches for phase II (tonic phase=time between minutes 20-40) through an electromagnetic field. See Yaksh T L, Ozaki G, McCumber D, Rathbun M, Svensson C, Malkmus S, Yaksh M C. *An automated flinch detecting system for use in the formalin nociceptive bioassay. J Appl Physiol.*, 2001; 90:2386-402.

As shown in FIG. 1, phase 1 and phase 2 data were obtained using homozygous (−/−) mice females (n=16), wild-type females (n=15), homozygous (−/−) mice males (n=9), and wild-type males (n=18). In all groups and in both phases, the AAK1 homozygous (−/−) mice exhibited significantly less recorded paw flinching than their wild-type (+/+) littermates.

Studies of AAK1 knockout mice showed that disruption of the AAK1 gene affects pain response as measured using the formalin paw test described above. The same test was used to confirm that the administration of an AAK1 inhibitor can also affect pain response.

A compound of the disclosure was tested in this assay at different doses. Gabapentin and pregabalin were used as positive controls. Results are shown below in Table 2, wherein the effect of gabapentin at 200 mg/kg is considered a 100% response, the % response for the other compounds is relative to the 200 mg/kg dose of gabapentin, "sc" means subcutaneous administration.

TABLE 2

| Compound | Dose (mg/kg) | Response |
|---|---|---|
| Gabapentin | 50 sc | 60% |
| Gabapentin | 200 sc | 100% |
| Pregabalin | 50 sc | 90% |
| Compound 5: (R)-1-(5H-chromeno[3,4-c]pyridin-8-yloxy)-4-methylpentan-2-amine | 10 sc | 45% |
| Compound 5: (R)-1-(5H-chromeno[3,4-c]pyridin-8-yloxy)-4-methylpentan-2-amine | 30 sc | 88% |

What is claimed is:

1. A method of inhibiting adaptor associated kinase 1 (AAK1) activity, comprising contacting AAK1 with a compound of formula (I), (I)

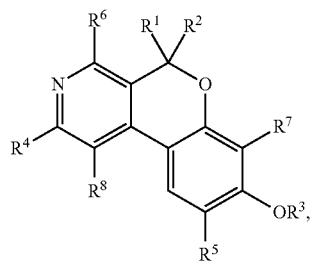

or a pharmaceutically acceptable salt thereof, wherein:
$R^1$ and $R^2$ are independently selected from hydrogen, $C_3$-$C_6$cycloalkyl, and $C_1$-$C_3$alkyl wherein the $C_1$-$C_3$alkyl is optionally substituted with one, two, or three groups independently selected from $C_1$-$C_3$alkoxy, $C_1$-$C_3$alkylamino, amino, cyano, $C_1$-$C_3$dialkylamino, halo, and hydroxy; or
$R^1$ and $R^2$ together are oxo; or
$R^1$ and $R^2$, together with the carbon atom to which they are attached, form an oxetane ring;
$R^3$ is $C_1$-$C_3$alkyl-Y or $C_2$-$C_8$alkyl, wherein the $C_2$-$C_8$alkyl is optionally substituted with one, two, three, or four groups independently selected from $C_1$-$C_3$alkoxy, $C_1$-$C_3$alkylamino, $C_1$-$C_3$alkoxy$C_2$-$C_3$alkylamino, amino, aryl, halo, $C_1$-$C_3$haloalkylamino, $C_1$-$C_3$haloalkylcarbonylamino, hydroxy, —$NR^xR^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxy$C_2$-$C_3$alkylamino, amino, aryl, aryl$C_1$-$C_3$alkyl, halo, $C_1$-$C_3$haloalkyl, $C_1$-$C_3$haloalkylamino and hydroxy;
$R^4$ is selected from hydrogen, $C_1$-$C_3$alkoxy, $C_1$-$C_3$alkoxycarbonylamino, $C_1$-$C_3$alkyl, $C_1$-$C_3$alkylamino, $C_1$-$C_3$alkylcarbonylamino, amino, arylamino, arylcarbonylamino, $C_3$-$C_6$cycloalkylamino, $C_3$-$C_6$cycloalkylcarbonylamino, $C_3$-$C_6$cycloalkyloxy, halo, $C_1$-$C_3$haloalkoxy, $C_2$-$C_3$haloalkylamino, $C_2$-$C_3$haloalkylcarbonylamino, and hydroxy;

$R^5$ is selected from hydrogen, $C_1$-$C_3$alkyl, cyano, $C_3$cycloalkyl, and halo;

$R^6$ is selected from hydrogen, $C_1$-$C_3$alkyl, $C_1$-$C_3$alkylcarbonylamino, amino, $R^7$ is selected from hydrogen, $C_1$-$C_3$alkoxy, $C_1$-$C_3$alkyl, cyano, —$CH_2OH$, —$CH_2OCH_3$, $CH(CH_3)OH$, $C(CH_3)_2OH$, halo, and $C_1$-$C_3$haloalkyl;

$R^8$ is selected from hydrogen, $C_1$-$C_3$alkoxy, cyano, and halo;

$R^x$ and $R^y$, together with the nitrogen atom to which they are attached, form a three- to six-membered ring; and Y is selected from

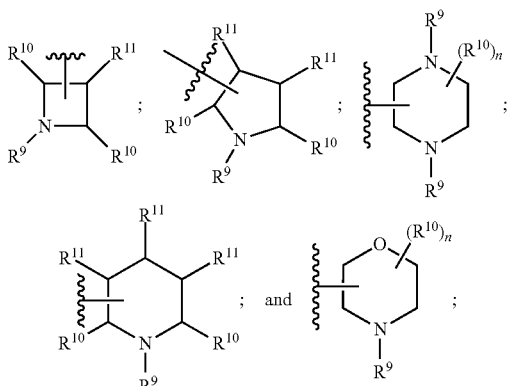

wherein $R^9$ is selected from hydrogen, $C_1$-$C_6$alkyl, $C_3$-$C_6$cycloalkyl, and $C_1$-$C_6$alkylcarbonyl;

n is 0, 1, 2, or 3;

each $R^{10}$ is independently selected from hydrogen, $C_1$-$C_6$alkyl, aryl, aryl$C_1$-$C_3$alkyl, $C_3$-$C_6$cycloalkyl, halo, and $C_1$-$C_3$haloalkyl; and each $R^{11}$ is independently selected from hydrogen, $C_1$-$C_3$alkoxy and hydroxy.

or a pharmaceutically acceptable salt thereof.

2. A method for treating neuropathic pain the method comprising administering to a patient in need thereof a therapeutically effective amount of a compound of formula (I)

(I)

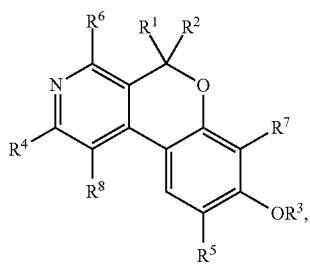

or a pharmaceutically acceptable salt thereof, wherein:
$R^1$ and $R^2$ are independently selected from hydrogen, $C_3$-$C_6$cycloalkyl, and $C_1$-$C_3$alkyl wherein the $C_1$-$C_3$alkyl is optionally substituted with one, two, or three groups independently selected from $C_1$-$C_3$alkoxy, $C_1$-$C_3$alkylamino, amino, cyano, $C_1$-$C_3$dialkylamino, halo, and hydroxy; or
$R^1$ and $R^2$ together are oxo; or
$R^1$ and $R^2$, together with the carbon atom to which they are attached, form an oxetane ring;
$R^3$ is $C_1$-$C_3$alkyl-Y or $C_2$-$C_8$alkyl, wherein the $C_2$-$C_8$alkyl is optionally substituted with one, two, three, or four groups independently selected from $C_1$-$C_3$alkoxy, $C_1$-$C_3$alkylamino, $C_1$-$C_3$alkoxy$C_2$-$C_3$alkylamino, amino, aryl, halo, $C_1$-$C_3$haloalkylamino, $C_1$-$C_3$haloalkylcarbonylamino, hydroxy, —$NR^xR^y$, and $C_3$-$C_8$cycloalkyl, wherein the cycloalkyl is further optionally substituted with one, two, or three groups independently selected from $C_1$-$C_3$alkoxy, $C_1$-$C_3$alkyl, $C_1$-$C_3$alkylamino, $C_1$-$C_3$alkoxy$C_2$-$C_3$alkylamino, amino, aryl, aryl$C_1$-$C_3$alkyl, halo, $C_1$-$C_3$haloalkyl, $C_1$-$C_3$haloalkylamino and hydroxy;
$R^4$ is selected from hydrogen, $C_1$-$C_3$alkoxy, $C_1$-$C_3$alkoxycarbonylamino, $C_1$-$C_3$alkyl, $C_1$-$C_3$alkylamino, $C_1$-$C_3$alkylcarbonylamino, amino, arylamino, arylcarbonylamino, $C_3$-$C_6$cycloalkylamino, $C_3$-$C_6$cycloalkylcarbonylamino, $C_3$-$C_6$cycloalkyloxy, halo, $C_1$-$C_3$haloalkoxy, $C_2$-$C_3$haloalkylamino, $C_2$-$C_3$haloalkylcarbonylamino, and hydroxy;
$R^5$ is selected from hydrogen, $C_1$-$C_3$alkyl, cyano, $C_3$cycloalkyl, and halo;
$R^6$ is selected from hydrogen, $C_1$-$C_3$alkyl, $C_1$-$C_3$alkylcarbonylamino, amino,
$R^7$ is selected from hydrogen, $C_1$-$C_3$alkoxy, $C_1$-$C_3$alkyl, cyano, —$CH_2OH$, —$CH_2OCH_3$, $CH(CH_3)OH$, $C(CH_3)_2OH$, halo, and $C_1$-$C_3$haloalkyl;
$R^8$ is selected from hydrogen, $C_1$-$C_3$alkoxy, cyano, and halo;
$R^x$ and $R^y$, together with the nitrogen atom to which they are attached, form a three- to six-membered ring; and
Y is selected from

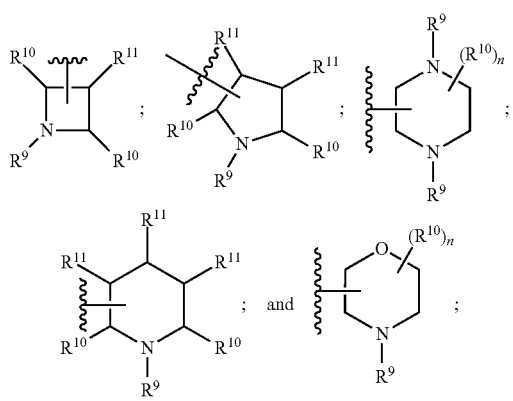

wherein $R^9$ is selected from hydrogen, $C_1$-$C_6$alkyl, $C_3$-$C_6$cycloalkyl, and $C_1$-$C_6$alkylcarbonyl;
n is 0, 1, 2, or 3;
each $R^{10}$ is independently selected from hydrogen, $C_1$-$C_6$alkyl, aryl, aryl$C_1$-$C_3$alkyl, $C_3$-$C_6$cycloalkyl, halo, and $C_1$-$C_3$haloalkyl; and
each $R^{11}$ is independently selected from hydrogen, $C_1$-$C_3$alkoxy and hydroxy.
or a pharmaceutically acceptable salt thereof.
3. The method of claim 2 wherein the neuropathic pain is fibromyalgia or peripheral neuropathy.

* * * * *

SEQUENCE LISTING

```
<160> NUMBER OF SEQ ID NOS: 1

<210> SEQ ID NO 1
<211> LENGTH: 18
<212> TYPE: PRT
<213> ORGANISM: Artificial
<220> FEATURE:
<223> OTHER INFORMATION: fluoresceinated peptide

<400> SEQUENCE: 1

Lys Glu Glu Gln Ser Gln Ile Thr Ser Gln Val Thr Gly Gln Ile Gly
1               5                   10                  15

Trp Arg
```